(12) United States Patent
Caplan et al.

(10) Patent No.: US 8,058,314 B2
(45) Date of Patent: Nov. 15, 2011

(54) CONDUCTANCE OF IMPROPERLY FOLDED PROTEINS THROUGH THE SECRETORY PATHWAY AND RELATED METHODS FOR TREATING DISEASE

(75) Inventors: Michael J. Caplan, Woodbridge, CT (US); Marie E. Egan, Madison, CT (US)

(73) Assignee: Yale University, New Haven, CT (US)

(*) Notice: Subject to any disclaimer, the term of this patent is extended or adjusted under 35 U.S.C. 154(b) by 58 days.

(21) Appl. No.: 11/749,525

(22) Filed: May 16, 2007

(65) Prior Publication Data
US 2008/0025921 A1    Jan. 31, 2008

Related U.S. Application Data

(63) Continuation of application No. 10/200,607, filed on Jul. 22, 2002, now abandoned, which is a continuation-in-part of application No. 09/976,963, filed on Oct. 12, 2001, now abandoned, which is a continuation-in-part of application No. 09/427,696, filed on Oct. 27, 1999, now Pat. No. 6,344,475.

(51) Int. Cl.
*A61K 31/12* (2006.01)
*A61K 31/35* (2006.01)

(52) U.S. Cl. .................. 514/683; 514/679; 514/456

(58) Field of Classification Search ............ 514/683, 514/679, 456
See application file for complete search history.

(56) References Cited

U.S. PATENT DOCUMENTS

| | | |
|---|---|---|
| 4,866,072 A | 9/1989 | Edwards et al. |
| 5,364,762 A | 11/1994 | Dornmair et al. |
| 5,384,128 A | 1/1995 | Meezan et al. |
| 5,401,777 A | 3/1995 | Ammon et al. |
| 5,434,086 A | 7/1995 | Collins et al. |
| 5,602,110 A | 2/1997 | Drumm et al. |
| 5,639,458 A | 6/1997 | Olsson et al. |
| 5,670,626 A | 9/1997 | Chang |
| 5,674,898 A | 10/1997 | Cheng et al. |
| 5,679,864 A | 10/1997 | Krackov et al. |
| 5,707,855 A | 1/1998 | Hancock et al. |
| 5,733,720 A | 3/1998 | Olivo |
| 5,734,023 A | 3/1998 | Nag et al. |
| 5,750,571 A | 5/1998 | Cheng et al. |
| 5,763,263 A | 6/1998 | Dehlinger |
| 5,834,421 A | 11/1998 | Cheng et al. |
| 5,846,998 A | 12/1998 | Schieven |
| 5,861,259 A | 1/1999 | Roberts et al. |
| 5,861,415 A | 1/1999 | Majeed et al. |
| 5,866,319 A | 2/1999 | Alizon et al. |
| 5,869,264 A | 2/1999 | Horisberger et al. |
| 5,877,210 A | 3/1999 | Schieven |
| 5,886,026 A | 3/1999 | Hunter et al. |
| 5,891,924 A | 4/1999 | Aggarwal |
| 5,912,176 A | 6/1999 | Wang |
| 5,939,536 A | 8/1999 | O'Riordan et al. |
| 5,942,493 A | 8/1999 | Kutscher et al. |
| 5,981,714 A | 11/1999 | Cheng et al. |
| 5,985,824 A | 11/1999 | Cheng et al. |
| 6,015,828 A | 1/2000 | Cuppoletti |
| 6,093,567 A | 7/2000 | Gregory et al. |
| 6,270,747 B1 * | 8/2001 | Nadel et al. ............... 424/9.2 |
| 6,323,191 B1 | 11/2001 | Harris et al. |
| 6,344,475 B1 | 2/2002 | Caplan et al. |
| 6,566,324 B2 * | 5/2003 | Nadel et al. ................ 514/1 |
| 6,664,272 B2 | 12/2003 | Snyder et al. |
| 6,673,843 B2 | 1/2004 | Arbiser |
| 2001/0004117 A1 | 6/2001 | Chikamatsu et al. |
| 2001/0036919 A1 | 11/2001 | Nadel et al. |
| 2002/0019382 A1 | 2/2002 | Snyder et al. |

FOREIGN PATENT DOCUMENTS

| | | |
|---|---|---|
| JP | 09/028392 | 2/1997 |
| WO | WO 93/13768 | 7/1993 |
| WO | WO 94/04139 | 3/1994 |
| WO | WO 95/05810 | 3/1995 |
| WO | WO 95/07933 | 3/1995 |
| WO | WO 95/12420 | 5/1995 |
| WO | WO 96/32139 | 10/1996 |
| WO | WO 98/37878 | 9/1998 |
| WO | WO 00/24391 | 5/2000 |
| WO | WO 00/70949 | 11/2000 |
| WO | WO 01/40188 | 6/2001 |
| WO | WO 02/02582 | 1/2002 |
| WO | WO 03/007975 | 1/2003 |
| WO | WO 03/035007 | 5/2003 |
| WO | WO 03/049717 | 6/2003 |

OTHER PUBLICATIONS

Intelihealth (Nov. 2008) by NHLBI, 3 pages.*
Phillips http://cysticfibrosis.respironics.com/treatment.asp (2010) 4 pages.*
Welsh et al. Scientific American (1995), 1-9.*
Hardie et al "Immunolocalization of Transforming Growth α Factor and Epidermal Growth Factor Receptor in Lungs of Patients with Cystic Fibrosis" Pediatric and Developmental Pathology 2, 415-423, 1999.
Rubin, Bruce K. "Mucus, Phlegm, and Sputum in Cystic Fibrosis" Respiratory Care, vol. 54, No. 6, 726-32, Jun. 2009.
Amara, et al., "Intracellular Protein Trafficking Defects in Human Disease", Trends in Cell Biology, 2: 145-149, 1992.
Ammon, et al., "Pharmacology of *Curcuma longa*" Planta Med. 57:1-7, 1991.
Araanjo, et al., "Potentiation by Turmeric and Curcumin of Gamma-Radiation-Induced Chromosome Aberrations in Chinese Hamster Ovary Cells", Teratog. Carcinog. Mutagen., 19(1):9-18, 1999.

(Continued)

*Primary Examiner* — Brandon Fetterolf
*Assistant Examiner* — Shirley V Gembeh
(74) *Attorney, Agent, or Firm* — Choate Hall & Stewart LLP

(57) ABSTRACT

This invention provides the methodology and agents for treating any disease or clinical condition which is at least partly the result of endoplasmic reticulum-associated retention of proteins. Thus, the methods and agents of the present invention provide for the release of normally retained proteins from the endoplasmic reticulum. The present invention is particularly useful for treating any disease or clinical condition which is at least partly the result of endoplasmic reticulum-associated retention or degradation of mis-assembled or mis-folded proteins.

10 Claims, 10 Drawing Sheets

OTHER PUBLICATIONS

Figure 1A:
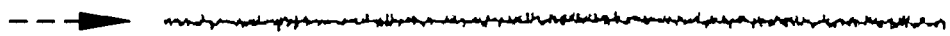
Figure 1A:
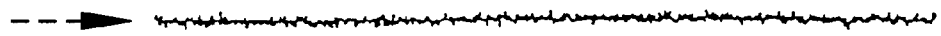
Figure 1A:
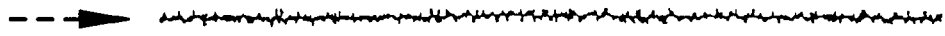

Aranjo, et al., "Biological Activities of *Curcuma longa L.*" Mem. Inst. Oswaldo Cruz. 96: 723-728, 2001.

Asai, et al., Occurrence of Orally Administered Curcuminoid as Glucuronide and Glucuronide/Sulfate Conjugates in Rat Plasma, Life Sciences, 67:2785-2793, 2000.

Bargon, et al., "Down-Regulation of Cystic Fibrosis Transmembrane Conductance Regulator Gene Expression by Agents that Modulate Intracellular Divalent Cations", Modular and Cellular Biology, 12(4): 1872-1878, 1992.

Barmatz, et al., "The Structure, Function, and Cellular Regulation of Ryanodine-Sensitive Ca2+ Release Channels", Int Rev Cytol. 183: 185-270, 1998.

Basavappa et al., "Cl- and K+ Transport in Human Biliary Cell Lines", Gastroenterology, 104(6): 1796-1805, 1993.

Beavo, et al., "Primary Sequence of Cyclic Nucleotide Phosphodiesterase Isozymes and the Design of Selective Inhibitors" Trends Pharmacol Sciences, 11:150, 1990.

Bell, et al., "T84 Cells: Anion Selectivity Demonstrates Expression of Cl" Conductance Affected in Cystic Fibrosis, Am. J. Physiol. 262: C555-0562, 1992.

Berridge, "The Biology and Medine of Calcium Signalling", Mol. Cell. Endocrin, 98: 119-124, 1994.

Berridge, M.J., "Inositol Trisphosphate and Calcium Signalling", Nature, 361: 315-325, 1993.

Beutler, et al., "Mutation Analysis in Hereditary Hemochromatosis", Blood Cells MoL Dis., 22: 187-194, 1996.

Bhavanishankar, et al., "Toxicity Studies on Turmeric -Long Term Toxicity Studies in Albino Rats and Monkeys", Journal of Food Science and Technology, India. 23(5):287-290, 1986.

Bhavanishankar, et al., Reproductive Response of Rats Fed Turmeric and its Alcoholic Extract, Journal of Food Science and Technology, India. 24(1): 45-49, 1987.

Bille, et al., "Subchronic Oral Toxicity of Turmeric Oleoresin in Pigs", Food Chem. Toxicol. 23(11): 967-973, 1985.

Bilmen, et al., "Inhibition of the SERCA Ca2+ Pumps by Curcumin. Curcumin Putatively Stabilizes the Interaction Between the Nucleotide-Binding and Phosphorylation Domains in the Absence of ATP", Eur. J. Biochem., 268:6318-6327, 2001.

Boucher, "What Can We Expect for Cystic Fibrosis", Drugs, 43(4): 431-439, 1992.

Brenan, et al., Automated Fluorometric Assay for T Cell Cytotoxicity,J. Immuno. Methods, 112: 121-131, 1988.

Brennan, et al., "Cystic Fibrosis", Cur Opin Infect Dis., 15(2): 175-182, 2002.

Brihaye, et al., "Chronic Rhinosinusitis in Cystic Fibrosis (Mucoviscidosis)", Acta Oto-Rhino Laryngologica Belg., 51: 323-337, 1997.

Canny et al., "The calcium pump inhibitors thapsigargin and curcumin alter delta F508 CFTR-chaperone interactions." (2003) FASEB J. 17(4-5).

Chao, et al., "Calcium-and CaMKII- Dependent Chloride Secretion Induced by the Microsomal Ca2+ATPase Inhibitor 2,5-Di-(Tert-Butyl)-1,4-Hydroquinone in Cystic Fibrosis Pancreatic Epithelial Cells", J. Clin. Invest. 96:1794-1801, 1995.

Cheek, T.R. "Calcium Regulation and Homeostasis", Curr. Opin. Cell. Biol. 3: 199-205, 1991.

Chen, et al., "Induction of HSP70 Gene Expression by Modulation of Ca+2 Ion and Cellular p53 Protein by Curcumin in Colorectal Carcinoma Cells", Molecular Carcinogenesis, 17: 224-234, 1996.

Cheng, et al., "Defective Intracellular Transport and Processing of CFTR is the Molecular Basis of Most Cystic Fibrosis", Cell, 63:827-834, 1990.

Cheng, et al., "Phase 1 Clinical Trial of Curcumm, A Chemopreventive Agent", in Patients with High-Risk of Pre-Malignant Lesions, Anticancer Research, 21: 2895-2900, 2001.

Chillaron, et al., "An Intracellular Trafficking Defect in Type 1 Cystinuria rBAT Mutants M46T and 467K", 1 Biol. Chem. 272(14): 9543-9549, 1997.

Choudhury, et al., "Intracellular Association Between UDP-Glucose: Glycoprotein Glucosyltransferase and an Incompletely Folded Variant of ai-Antitrypsin", The Journal of Biological Chemistry, 272(20): 13446-13451, 1997.

Christensen, et al., "Derivatives of Thapsigargin as Probes of its Binding Site on Endoplasmic Reticulum Ca2+ ATPase", Federation of European Biochemical Societies, 335(3): 345-348, 1993.

Clark, et al., "Effects of Thapsigargin, an Intracellular Calcium-Mobilizing Agent, on Synthesis and Secretion of Cartilage Collagen and Proteoglycan", Journal of Orthopaedic Research, 12:601-611, 1994.

Cohn, et al., "Characterization of the Cystic Fibrosis Transmembrane Conductance Regulator in a Colonocyte Cell Line",Proc. Nat. Acad. Sci. 89: 2340-2344, 1992.

Commandeur, et al., "Cytotoxicity and Cytoprotective Activities of Natural Compounds", The Case Curcumitin, Xenobiotica, 26(7): 667-680, 1996.

Cooper, et al., "Analysis of Curcuminoids by High-Performance Liquid Chromatography", Food Phytochemicals II: Teas, Spices, and Herbs, ACS Symposium Series, American Chemical Society, Washington, DC 231-236, 1994.

Courtois, et al., "A Tyrosine-Based Signal Targets H/K-ATPase to a Regulated Compartment and is Required for the Cessation of Gastric Acid Secretion", Cell, 90: 501-510, 1997.

Crawford, et al., "Immunocytochemical Localization of the Cystic Fibrosis Gene Product CFTR", Proc. Nat. Acad. Sci, 88: 9262-9266, 1991.

Dalemans, et al., "Altered Chloride Ion Channel Kinetics Associated with the F508 Cystic Fibrosis Mutation", Nature, 354:526-528, 1991.

Davis, et al., "Cystic Fibrosis", Am. J. Respir. Crit. Care Med. 154: 1229-1256, 1996.

Demars, et al., "Mutations that Impair a Posttranscriptional Step in Expression of I ILA-A and -B Antigens" PNAS, 82: 8183-8187, 1985.

Deodhar, et al., Preliminary Studies on Antirheumatic Activity of Curcumin (Diferuloyl Methane). Ind. J. Med. Res. 71: 632-634, 1980.

Deshpande, et al., "Subchronic Oral Toxicity of Turmeric and Ethanolic Turmeric Extract in Female Mice and Rats", Toxicology Letters (Shannon). 95(3): 183-193, 1998.

Egan et al., "Curcumin, a major constituent of turmeric, corrects cystic fibrosis defects." Science 304(5670):600-602, 2004.

Egan, et al., "Calcium-Pump Inihibitors Induce Functional Surface Expression of DeltaF508-CFTR Protein in Cystic Fibrosis Epithelial Cells", Nat Med., 8(5):485-492, 2002.

Egan, et al., "Differential Expression of ORCC and CFTR Induced by Low Temperature in CF Airway Epithelial Cells" Am. J. Physiol. 268: C243-C251, 1995.

Elmore, et al., "Comparative Tissue-Specific Toxicities of 20 Cancer Preventive Agents Using Cultured. Cells from 8 Different Normal Human Epithelia", In Vitr. Mol. Toxicol. 14(3): 191-207, 2001.

Fritzzel, et al., "Altered Regulation of Airway Epithelial Cell Chloride Channels in Cystic Fibrosis", Science, 233: 558-560, 1986.

Fuchs, et al., "Effect of Aerosolized Recombinant Human DNase on Exacerbations of Respiratory Symptoms and on Pulmonary Function in Patients with Cystic Fibrosis", The New England Journal of Medicine, 331(10): 637-642, 1994.

Galietta, et al., Activation of Ca2+ Dependent K + and Cl- Currents by UTP and ATP in CFPAC-1 Cells, Pflugers Arch. 426(6): 534-541, 1994.

Giri, et al., "Sister Chromatid Exchange and Chromosome Aberrations Induced by Curcumin and Tartrazine on Mammalian Cells in vivo", Cytobios, 62(249): 111-117, 1990.

Goh, et al., "Allergic Contact Dermatitis to *Curcuma-longa* Turmeric", Contact Dermatitis, 17(3): 186, 1987.

Goldstein, et al., "Receptor-Mediated Endocytosis: Concepts Emerging from the LDL Receptor System" Ann. Rev. Cell Biol. 1: 1-39, 1985.

Gottardi, et al., "An Ion-Transporting ATPase Encodes Multiple Apical Localization Signals", J. Cell. Biol. 121: 283-293, 1993.

Gregory, et al., "Expression and Characterization of the Cystic Fibrosis Transmembrane Conductance Regulator", Nature, 347:382-386, 1990.

Griffiths, et al., Cell, 52: 329-341, 1988.

Grubb, et al., "Inefficient Gene Transfer by Adenovirus Vector to Cystic Fibrosis Airway Epithelia of Mice and Humans", Nature, 371: 802-806, 1994.

Grubb, et al., Hyperabsorption of Na+ and Raised Ca +—Mediated Cl- Secretion in Nasal, Epithelia of CF Mice, Am. J. Physiol. 266: C1478-1483, 1994.

Grubb, et al., Isobutylmethylxanthine Fails to Stimulate Chloride Secretion in Cystic Fibrosis Airway Epithelia Am. J. Resp. Cell. Mol. Biol. 8: 454-460, 1993.

Grynkiewicz, et al., "A New Generation of Ca2+ Indicators with Greatly Improved Fluorescence Properties" J. Biol. Chem., 260: 3440-3450, 1985.

Gupta, et al., "Mechanisms of Curcumin Induced Gastric Ulcer in Rats", Indian J. Med. Res. 71:806-814, 1980.

Hammond, et al., "Role of N-Linked Oligosaccharide Recognition, Glucose Trimming, and Calnexin in Glycoprotein Folding and Quality Control", Proc. NatL Acad. Sci. USA, 91: 913-917, 1994.

Hamosh, et al., "CFTR Nonsense Mutations G542X and W1282X Associated with Severe Reduction of CFTR mRNA in Nasal Epithelial Cells", Hum. Mol. Gen. 1:542-544, 1992.

Hardie et al "Immunolocalization of Transforming Growth Factor and Epidermal Growth Factor Receptor in Lungs of Patients with Cystic Fibrosis" Pediatric and Developmental Pathology 2, 415-423, 1999.

Hata, et al., Allergic Contact Dermatitis from Curcumin (Turmeric), Contact Dermatitis, 36(2): 107-108, 1997.

Haws, et al., "AF508-CFTR Channels: Kinetics, Activation by Forskolin, and Potentiation by Xanthines", Am. J. Physiol, 270:C1544-C1555, 1996.

Hellinger, et al., Phase I/II Randomized, Open-Label Study of Oral Curcumin Safety, and Antiviral Effects on HIV-RT PCR in HIV+Individuals, 3rd Conference on Retroviruses and Opportunistic Infections, Jan. 28-Feb. 1, 1996, Washington, D.C. Abstract #140.

Higgins, et al., "ABC Transporters: From Microorganisms to Man", Ann. Rev. Cell. Biol. 8: 67-113, 1992.

Hobbs, et al., "The LDL Receptor Locus in Familial Hypercholesterolemia: Mutational Analysis of a Membrane Protein", Annu. Rev. Genet. 24:133-170, 1990.

Hofer, et al., Technique for in Situ Measurement of Calcium in Intracellular Inositol 1,4,5-Trisphosphate-Sensitive Stores Using the Fluorescent Indicator Mag-Fura-2, Proc. Natl. Acad. Sci. 90: 2598-2602, 1993.

Holder, et al., "The Metabolism and Excretion of Curcumin (1,7-bis-(4-Hydroxy-3-Methoxyphenyl)-1,6-Heptadiene-3,5-dione0 in the Rat", Xenobiotica, 8(12): 761-768, 1978.

Hong, et al., "Curcumin Inhibits Tyrosine Kinase Activity of p185"eu and Also Depletesp185neu1° Clinical Cancer Research, 5: 1884-1891, 1999.

Huber, et al., "Implications of the Three-Dimensional Structure of al -Antitrypsin for Structure and Function of Serpins", Biochemistry, 28: 8951-8966, 1989.

Hughes, et al., "Misfolded Major Histocompatibility Complex Class I Heavy Chains are Translocated into the Cytoplasm and Degraded by the Proteasome", PNAS, 94: 1896-1901,1997.

Hwang, et al., "Genistein Potentiates Wild-Type and F508-CFTR Channel Activity", Am. J. Physiol. 273:C988-C998, 1997.

Hyde, et al., "Structural Model of ATP-Binding Proteins Associated with Cystic Fibrosis, Multidrug Resistance and Bacterial Transport", Nature, 346: 362-365, 1990.

ICiec-Swierczynska, et al., "Occupational Allergic Contact Dermatitis Due to Curcumin Food Colour in a Pasta Factory Worker", Contact Dermatitis, 39(1): 30-31, 1998.

ICinoshita, et al., "Role of Phosphatidylinositol-Linked Proteins in Paroxysmal Nocturnal Hemoglobinuria Pathogenesis", Annu. Rev. Med. 47:1-10, 1996.

Inesi, et al., "Thapsigargin, a High Affinity and Global Inhibitor of Intracellular Ca2+Transport ATPases", Arch.Biochem. Biophys, 298: 313-317, 1992.

Inoue, et al., Thapsigargin, A High Affinity and Global Inhibitor of Intracellular Ca2+Transport ATPases, Am. J. Physiol. Cell Physiol, 272(6): 41-46, 1997.

International Preliminary Examination Report issued for PCT application PCT/US02/32801 dated Nov. 4, 2005.

International Search Report issued for corresponding PCT application PCT/US02/32801, dated Feb. 15, 2004.

International Search Report issued for PCT application PCT/US05/08184 dated May 15, 2008.

International Search Report issued for PCT application PCT/US99/25221 dated Nov. 30, 2000.

Ireson, Metabolism of the Cancer Chemopreventative Agent Curcumin in Human and RatIntestine, Cancer Epidemiology, Biomarkers & Prevention, 11:105-111, 2002.

Jain, et al., "Evaluation of Genotoxic Effects of Turmeric in Mice", Curr. Sci. 56(19): 1005-1006, 1987.

James, et al., Clinical Trial Finds no Antiviral Effect. Aids Treatment News, Issue No. 242, 1996.

Jayaprakasha, et al., "Improved HPLC Method for the Determination of Curcumin, Demethoxycurcumin, and Bisdemethoxycurcumin", Journal of Agricultural and Food Chemistry, 50: 3668-3672, 2002.

Johnson, et al., "Efficiency of Gene Transfer for Restoration of Normal Airway Epithelial Function in Cystic Fibrosis", Nature Gen. 2:21-25, 1992.

Johnson, et al., Curcumin, "WHO Food Additives Series", 35: 173-189, 1996.

Joint, et al., "Evaluation of Certain Food Additives and Contaminants", Section 3.13.2 Curcumin, Fifty-Seventh Report of the Joint FAO/WHO Expert Committee on Food Additives, Who Technical Report Series No. 909. 20-21, 2002.

Jorissen, et al., "Genotype-Phenotype Correlations for the Paranasal Sinuses in Cystic Fibrosis", Am J. Respir Crit Care Med, 159: 1412-1416, 1999.

Kerem, et al., "Indentification of the Cystic Fibrosis Gene: Genetic Analysis". Science, 245:1073-1080, 1989.

Khan, et al., "Interactions of Dihydroxybenzenes with the Ca2+—ATPase: Separate Binding Sites for Dihydroxybenzenes and Sesquiterpene Lactones".Biochem. 34: 14385-14393, 1995.

Knowles, et al., "In vivo Potential Difference: Techniques and Protocols for Assessing Efficacy of Gene Transfer in Cystic Fibrosis", Hum. Gene. Ther. 6: 445-455, 1995.

Knowles, et al., "Increased Bioelectric Potential Difference Across Respiratory Epithelia in Cystic Fibrosis", N. Engl. J. Med. 305: 1489-1495, 1981.

Kositchaiwat, et al., "*Curcuma longa* Linn in the Treatment of Gastric Ulcer Comparison to Liquid Antacid: A Controlled Clinical Trial", J. Med. Assoc. Thai. 76: 601-605,1993.

Kunzelmann, et al., "An Immortalized Cystic Fibrosis Tracheal Epithelial Cell Line Homozygous for the AF508 CFTR Mutation", Am. J. Respir. Cell MoL Biol. 8: 522-529, 1993.

Labriola, et al., "Retention of Glucose Units Added by the UDP-GLC: Glycoprotein Glucosyltransferase Delays Exit of Glycoproteins from the Endoplasmic Reticulum", J. Cell. Biol. 130(4): 771-779, 1995.

Lau, et al., "A Frameshift Mutation in a Patient with Tay-Sachs Disease Causes Premature Termination and Defective Intracellular Transport of the a-Subunit of f3-Hexosaminiase", the Journal of Biological Chemistry, 264(35):21376-21379, 1989.

Le, et al., "Association Between Calnexin and a Secretion-Incompetent Variant of Human ai Antitrypsin", The Journal of Biological Chemistry, 269(10):7514-7519, 1994.

Li, et al., "Regulation of Chloride Channels by Protein Kinase C in Normal and Cystic Fibrosis Airway Epithelia", Science , 244: 1353-1356, 1989.

Lin, et al., "Recent Studies on the Biofunctions and Biotransformations of Curcumin", Biofactors, 13: 153-158, 2000.

Loebermann, et al., Human ai -Proteinase Inhibitor, J. Mol. Bio. 177: 531-556, 1984.

Logan-Smith, et al., "Curcumin, A Molecule that Inhibits the Ca2+—ATPase of Sarcoplasmic Reticulum but Increases the Rate of Accumulation of Ca2+" 1 Biol. Chem. 276:46905-46911, 2001.

Logan-Smith, et al., "Evidence for a Global Inhibitor-Induced Conformation Change on the Ca2+—ATPase of Sarcoplasmic Reticulum from Paired Inhibitor Studies", Biochemistry, 41: 2869-2875, 2002.

Loo, et al., "Correction of Defective Protein Kinesis of Human P-Glycoprotein Mutants by Substrates and Modulators" Biol. Chem. 272: 709-712, 1997.

Loo, et al., "Superfolding of the Partially Unfolded Core-Glycosylated Intermediate of Human P-Glycoprotein into the Mature Enzyme is Promoted by Substrate-Induced Transmembrane Domain Interactions", J. Biol. Chem. 273: 14671-14674, 1998.

Luk, et al., "Production of Cyclopiazonic Acid by *Aspergillus flavus* Link", Applied and Environmental Microbiology, 33(1): 211-212, 1977.

Lytton, et al., "Thapsigargin Inhibits the Sarcoplasmic or Endoplasmic Reticulum Ca-ATPase Family of Calcium Pumps", The Journal of Biological Chemistry, 266(26):17067-17071, 1991.

Maitra, et al., "Increased Functional Cell Surface Expression of CFTR and F508-CFTR by the Anthracycline Doxorubicin", Am. J. Physiol Cell Physiol, 280: C1031-C1037, 2001.

Miquel, et al., "Effects of Turmeric on Blood and Liver Lipoperoxide Levels of Mice: Lack of Toxicity", Age (Chester), 18(4): 171-174, 1995.

Miquel, et al., "The Curcuma Antioxidants: Pharmacological Effects and Prospects for Future Clinical Use", A Review, Archives of Gerontology and Geriatrics, 34: 37-46, 2002.

Montero, et al., "Ca2+ Homeostasis in the Endoplasmic Reticulum: Coexistence of High and Low [Ca21 subcompartments in Intact HeLa Cells", J. Cell. Biol., 139: 601-611, 1997.

Moon, et al., "Calcium-stimulated-CL-secretion in Calu-3 human airway cells requires CFTR",American Journal of Physiology, 273:L1208-L1219 (1997).

Morello, et al., "Nephrogenic Diabetes Insipidus", Annu. Rev. Physiol. 63: 607-630, 2001.

Nathanson, et al., "Measurement of Chloride Concentration in Microvolume Samples of Sweat", Pediatr. Pulmonol. 17(5): 340-342, 1994.

National Toxicology Program (U.S. Department of Health and Human Services). 1993, NTP Technical Report on the Toxicology and Carcinogenesis Studies of Turmeric Oleoresin.

Nauseff, W., "Quality Control in the Endoplasmic Reticulum: Lessons from Hereditary Myeloperoxidase Deficiency", J. Lab Clin Med, 134(3): 215-221, 1999.

NCI, DCPC, Chemoprevention Branch and Agent Development Committee. 1996. Clinical Development Plan: Curcumin. Journal of Cellular Biochemistry. Supplement. 26: 72-85, 1996.

Neyses, et al., "Use of antisense oligonucleotides for selective inhibition of gene expression in adult cardiomyocytes", Funktionsanalyse Biologischer Systeme, 25:53-62 (1996) Abstract Only.

Nicholson, et al., "Differential Modulation of Tissue Function and Therapeutic Potential of Selective Inhibitors of Cyclic Nucleotide Phosphodiesterase Isoenzymes", Trends Pharmacol. Sciences, 12:19, 1991.

Nigam, et al., "A Set of Endoplasmic Reticulum Proteins Possessing Properties of Molecular Chaperones Includes Ca2+—Binding Proteins and Members of the Thioredoxin Superfamily", J. Biol. Chem. 269: 1744-1749, 1994.

Norton, et al., "Bacterial 13-Galactosidase as a Marker of Rous Sarcoma Virus Gene Expression and Replication", Molecular & Cellular Biology, 5: 281-290, 1985.

Oceandy, et al., "Gene Complementation of Airway Epithelium in the Cystic Fibrosis Mouse is Necessary and Sufficient to Correct the Pathogen Clearance and Inflammatory Abnormalities", Hum Mol Genet 11(9): 1059-1067, 2002.

Ostedgaard, et al., "Processing of CFTR Bearing the P574H Mutation Differs from Wild-Type and AF508-CFTR", J. Cell. Sci, 112: 2091-2098, 1999.

Pan, et al., "Biotransformation of Curcumin Through Reduction and Glucuronidation in Mice" Drug Metabolism and Disposition, 27: 486-494, 1999.

Parker et al., "Drosophila UDP-Glucose:Glycoprotein Glucosyltranserase: Sequence and Characterization of an Enzyme that Distinguishes Between Denatured and Native Protiens", The EMBO Journal, 14(7):1294-1303, 1995.

Pietrobon et al., "Structural and Functional Aspects of Calcium Homeostatis in Eukaryotic Cells", *Eur J. Biochem* 193:599-622, 1990.

Pilewski, et al., "Role of CFTR in Airway Disease", Physiological Reviews, 79: S215-S255,1999.

Pind, et al., "Participation of the Endoplasmic Reticulum Chaperone Calnexin (p88,IP90) in the Biogenesis of the Cystic Fibrosis Transmembrane Conductance Regulator", The Journal of Biological Chemistry , 269(17): 12784-12788, 1994.

Porgador, et al., "Natural Killer Cell Lines Kill Autologous 02-Microglobulin-DeficientMelanoma Cells: Implications for Cancer Immunotherapy", Proc. NatL Acad. Sci. USA,94:13140-13145, 1997.

Quinton, "Defective Epithelial Ion Transport Cystic Fibrosis", Clin. Chem., 35: 726-730,1989.

Quittner, et al., "Effects of Tobramycin Solution for Inhalation of Global Ratings of Quality ofLife in Patients with Cystic Fibrosis and Pseudomonas Aeruginosa Infection", PediatrPulmonol, 33(4):269-276, 2002.

Qureshi, et al., "Toxicity Studies on *Alpinia galanga* and *Curcuma longa*", Planta Med.58(2): 124-127, 1992.

Ravindranath, et al., "Absorption and Tissue Distribution of Curcumin in Rats", Toxicology,(Amst). 16(3): 259-265, 1980.

Ravindranath, et al., "Metabolism of Curcumin Studies with Tritium Labeled Curcumin", 22(4): 337-344, 1982.

Ricci°, et al., "Genetic Toxicology Testing of Natural Products being Developed as Cancer Chmopreventive Agents", Environmental and Molecular Mutagenesis, 37 (Supplement 32), 2001.

Rich, et al., "Expression of Cystic Fibrosis Transmembrane Conductance Regulator Corrects Defective Chloride Channel Regulation in Cystic Fibrosis Airway Epithelial Cells", Nature, 347: 358-363, 1990.

Riordon, et al., "Indentification of the Cystic Fibrosis Gene: Cloning and Characterization of Complementary DNA" Science, 245: 1066-1073, 1989.

Robinson, et al., "Ca2+ influx induced by the Ca2+—ATPase-inhibitors 2, 5-di-(t-butyl)-1, 4-benzohydroquinone and thapsigargin in bovine adrenal chromaffin cells", Biochemical J.,288:457-463 (1992).

Rodgers, et al., "Pharmacological Treatment of the Biochemical Defects in Cystic Fibrosis Airways", Eur Respir. J. 17: 1314-1321, 2001.

Rosenstein, et al., "Cystic Fibrosis", Lancet, 351: 277-282, 1998.

Rouard, et al., "Congenital Insulin Resistance Associated with a Conformational Alteration in a Conserved 13-Sheet in the Insulin Receptor Li Domain", The Journal of Biological Chemistry, 274(26): 18487-18491, 1999.

Rubenstein, et al., In vitro Pharmacologic Restoration of CFTR-Mediated Chloride Transport with Sodium 4-Phenylbutyrate in Cystic Fibrosis Epithelial Cells Containing F508-CFTR, J. Clin. Invest. 100: 2457-2465, 1997.

Rubin, Bruce K. "Mucus, Phlegm, and Sputum in Cystic Fibrosis" Respiratory Care, vol. 54, No. 6, Jun. 2009.

Ruby et al., "Anti-tumour and antioxidant activity of natural curcuminoids." Cancer Letters NY 94(1):79-83, 1995.

Sambaiah, et al., "Influence of Turmeric and Curcumin on Growth, Blood Constituents and Serum Enzymes in Rats", Journal of Food Science and Technology, 19(5): 187-190, 1982.

Satoskar, et al., "Evaluation of Anti-Inflammatory Property of Curcumin (Diferuloyl Methane) in Patients with Postoperative Inflammation", Int. J. Clin. Pharmacol. Ther. Toxicol. 24: 651-654, 1986.

Schmitz, et al., "In vivo iodination of a misfolded proinsulin reveals co-localized signals for Bipbinding and for degradation in the ER", EMBO Journal, 14:1091-1098 (1995).

Schoumacher, et al., A Cystic Fibrosis Pancreatic Adenocarcinoma Cell Line,Proc. Natl. Acad. Sci. 87: 4012-4016, 1990.

Seibert, et al., "Cystic fibrosis: Channel, catalytic, and folding properties of the CFTR protein",Journal of Bioenergetics and Biomembranes, 29:429-442 (1997)—Abstract Only.

Sethi, et al., Toxicity Studies of Curcumin, A Non-Steroid Anti-Inflammatory Agent in Rat and Monkey, U.P. Veterinary Journal, 4(3/4): 153-157, 1976.

Shankar, et al., "Toxicity Studies on Tumeric (*Curcuma longa*): Acute Toxicity Studies in Rats, Guineapigs & Monkeys", Indian J. Exp. Biol. 18(1): 73-75, 1980.

Sharma, et al., "Pharacodynamic and Pharmacokinetic Study of Oral Curcuma Extract in Patients with Colorectal Cancer", Clinical Cancer Research, 7: 1894-1900,2001.

Shepard, et al., Structure and Function of the CFTR Chloride Channel, Physiological Reviews, 79(1): S23-S45, 1999.
Shoba, et al., "Influence of Piperine on the Pharmacokinetics of Curcumin in Animals and Human Volunteers", Planta Med. 64(4): 353-356, 1998.
Simon, et al., "Gitelman's Variant of Bartter's Syndrome, Inherited Hypokalaemic Alkalosis, is Caused by Mutations in the Thiazide-Sensitive Na-Cl Cotransporter", Nat. Genet., 12: 24-30, 1996.
Soni, et al., "Effect of Oral Curcumin Adminstration on Serum Peroxides and Cholesterol Levels in Human Volunteers", Indian J. Physiol. Pharmacol. 36(4): 273-275, 1992.
Sousa, et al., "The Interaction of the UDP-GLC:Glycoprotein Glucosyltransferase with the Acceptor Glycoprotein", Cellular and Molecular Biology, 42(5): 609-616, 1996.
Srimal, R.C., "Turmeric: A Brief Review of Medicinal Properties", Fitoterapia, LXVIII(6): 483-493, 1997.
Steagall, et al., "Stimulation of Cystic Fibrosis Transmembrane Conductance Regulator Dependent Short-Circuit Currents Across AF508 Murein Intestines" Gastroenterology, 116(6): 1379-1388, 1999.
Stein, et al., What do Dysfunctional Serpins Tell Us About Molecular Mobility and Disease? Structural Biology, 2(2): 96-113, 1995.
Stucki, et al., "Successful Management of Severe Respirartory Failure Combining Heliox with Noninvasive High-Frequency Percussive Ventilation", Crit Care Med.30(3): 692-694, 2002.
Stutman, et al., "Antibiotic Prophylaxis in Infants and Young Children with Cystic Fibrosis: A Randomized Controlled Trial", J. Pediatr. 140(3):299-305, 2002.
Sumbilla, et al., "The Slippage of the Ca2+ Pump and its Control by Anions and Curcumin in Skeletal and Cardiac Sarcoplasmic Reticulum", J. Biol. Chem. 277:13900-13906, 2002.
Thomas, et al., "The Cystic Fibrosis Transmembrane Conductance Regulator", The Journal of Biological Chemistry, 267(9): 5727-5730, 1992.
Tonnesen, et al., "Studies on Curcumin and Curcuminoids IX: Investigation of the Photobiological Activity of Curcumin Using Bacterial Indicator Systems", Journal of Pharmaceutical Sciences, 76(5): 371-373, 1987.
Travis, et al., "Human Plasma Proteinase Inhibitors", Annual Review of Biochemistry, 52:655-709, 1983.
Trelman, et al., "A Tool Coming of Age: Thapsigargin as an Inhibitor of Sacro-Endoplasmic Reticulum Ca2+—ATPases", Tips, 19: 131-135, 1998.
Trombetta, et al., "Glucosylation of Glycoproteins by Mamrnalian, Plant, Fungal, and Trypanosomatid Protozoa Microsomal Membranes", Biochemistry, 28: 8108-8116, 1989.
Trombetta, et al., "Purification to Apparent Homogeneity and Partial Characterization of Rat Liver UDP-Glucose: Glycoprotein Glucosyltransferase", J. Biol. Chem. 267:9236-9240, 1992.
Tsien, et al., "Calcium Homeostasis in Intact Lymphocytes: Cytoplasmic Free Calcium Monitored with a New, Intracellularly Trapped Fluorescent Indicator", J. Cell. Biol. 94: 325-334, 1982.
Tsien, R.Y., "New Calcium Indicators and Buffers with High Selectivity Against Magnesium and Protons: Design, Synthesis, and Properties of Prototype Structures", Biochem. 19: 2396-2404, 1980.
Van Dau, et al., "The Effects of Traditional Drug, Turmeric (*Curcuma longa*) and Placebo onthe Healing of Duodenal Ulcer", Phytomedicine, 5:29-34, 1998.
Venkatesan et al, "Curcumin Protects Bleomycin-Induced Lung Injury in Rats" Life Sciences, 61(6):51-58, 1997.
Vijayalaxmi, "Genetic Effects of Turmeric and Curcumin in Mice and Rat", Mutat. Res. 79(2): 125-132, 1980.
Wahlstrom, et al., "A Study on the Fate of Curcumin in the Rat", Acta Pharmacol. Et Toxicol. 43: 86-92, 1978.
Wang, et al., "Mutation in the Gene Responsible for Cystic Fibrosis and Predisposition to Chronic Rhinosinusitis in the General Population", JAMA, 284(14): 1814-1819, 2000.
Ward, et al., "Degradation of CFTR by the Ubiquitin-Proteasome Pathway" Cell, 83:121-127, 1995.
Welsh, "An Apical-Membrane Chloride Channel in Human Tracheal Epithelium". Science, 232: 1648-1650, 1986.
Welsh, et al., "Molecular Mechanisms of CFTR Chloride Channel Dysfunction in Cystic Fibrosis" Cell, 73: 1251-1254, 1993.
Whitcome, et al., "Binding of Sesquiterpene Lactone Inhibitors to the Ca2+ ATPase",Biochem, J.: 310: 859-868, 1995.
Wild, et al., Characterization of [3H] Ryanodine Binding Sites in Mammalian Lung, Arch. Biochem Biophys, 379(1): 109-118, 2000.
Written Opinion issued for PCT application PCT/US05/08184 dated Apr. 4, 2008.
Xu, et al., "Potential for Pharmacology of Ryanodine Receptor/Calcium Release Channels", Ann NY Acad Sci, 853: 130-148, 1998.
Yamamoto, et al., "Deletion in Cysteine-Rich Region of LDL Receptor Impedes Transport to Cell Surface in WHHL Rabbit", Science, 232: 1230-1237, 1986.
Yang, et al., "The Common Variant of Cystic Fibrosis Transmembrane Conductance Regulator is Recognized by hsp70 and Degraded in a Pre-Golgi Nonlysosomal Compartment", Proc. Natl, Acad. Sci. USA. 90: 9480-9484, 1993.
Yap, et al., "Cytotoxic T Cells Specific for Influenza Virus-Infected Target Cells", Immunology, 32: 151-159, 1977.
Yoshida, et al., Carbohydrate Composition of Normal and Variant Human Alpha 1-Protease Inhibitors, Arch. Biochem. Biophys, 195: 591-595, 1979.
Yu, et al., "The Z Type Variation of Human ai-Antitrypsin Causes a Protein Folding Defect", Structural Biology, 2: 363-367, 1995.
Zeiher, et al., "A Mouse Model for the Delta F508 Allele of Cystic Fibrosis", J. Clin. Invest. 96(4): 2051-2064, 1995.
Zeitlin, et al., A Cystic Fibrosis Bronchial Epithelial Cell Line: Immortalization by Adeno-12-SV40 Infection Am. J. Resp Cell. Mol. Biol. 4: 313-319, 1991.
Zhang, et al., "Quality Control in the Secretory Pathway: The Role of Calreticulin, Calnexinand BiP in the Retention of Glycoproteins with C-Terminal Truncations", Molecular Biology ofthe Cell, 8:1943-1954 (1997).

* cited by examiner

Excised at -50m V 2 minutes after excision, 1mM ATP in the bath, -80m V 2 minutes later, +80m V Excised at -50m V 2 minutes after excision, 1mM ATP in the bath, -80m V 2 minutes later, +80m V

CONDUCTANCE OF IMPROPERLY FOLDED PROTEINS THROUGH THE SECRETORY PATHWAY AND RELATED METHODS FOR TREATING DISEASE

CROSS-REFERENCE TO RELATED APPLICATION

This application is a continuation of U.S. Ser. No. 10/200,607, filed Jul. 22, 2002, which is a continuation-in-part of U.S. Ser. No. 09/976,963, filed Oct. 12, 2001, which is a continuation-in-part of U.S. Pat. No. 6,344,475, the contents of each of which are herein incorporated by reference.

ACKNOWLEDGMENT OF FEDERAL SUPPORT

The present invention arose in part from research funded by the following NIH grants: GM42136, DK17433, DK53428, DK50230, and HD32573, and the U.S. government accordingly has certain rights in this invention.

FIELD OF THE INVENTION

This invention provides the methodology and agents for treating any disease or clinical condition which is at least partly the result of endoplasmic reticulum-associated retention of proteins. Thus, the methods and agents of the present invention provide for the release of normally retained proteins from the endoplasmic reticulum. The present invention is particularly useful for treating any disease or clinical condition which is at least partly the result of endoplasmic reticulum-associated retention or degradation of mis-assembled or mis-folded proteins.

BACKGROUND

All publications and patent applications herein are incorporated by reference to the same extent as if each individual publication or patent application was specifically and individually indicated to be incorporated by reference.

A. Introduction

Protein folding and quality control machinery has been implicated in the molecular pathogenesis of several human diseases caused by defective intracellular transport of an aberrantly folded protein through the secretory pathway. Exemplary diseases include pulmonary emphysema resulting from severe plasma α-antitrypsin deficiency and Cystic Fibrosis resulting from mutations in the cystic fibrosis transmembrane conductance regulator (Amara et al., *Trends Cell. Biol.* 2:145-149; Le et al., *J. Biol. Chem.* 269:7514-7519; Pind et al., *J. Biol. Chem.* 269:12784-12788). This invention is directed to the treatment and cure of such diseases.

Although the treatment and cure of Cystic Fibrosis and Chronic Obstructive Pulmonary Disease have been chosen as representative diseases for the purpose of describing and explaining the present invention, the compositions and/or methods of the present invention are applicable to the treatment and cure of any disease which involves the defective intracellular transport of mis-folded proteins.

B. Cystic Fibrosis—An Overview of the Disease, Protein and Gene

The Disease of Cystic Fibrosis. Cystic Fibrosis (CF) is an inherited multi-system metabolic disorder of the eccrine and exocrine gland function, usually developing during early childhood and affecting mainly the pancreas, respiratory system and sweat glands. Glands which are affected by CF produce abnormally viscous mucus, usually resulting in chronic respiratory infections, impaired pancreatic and digestive function, and abnormally concentrated sweat. CF is also called Clarke-Hadfield syndrome, fibrocystic disease of the pancreas and mucoviscidosis.

CF is the most common fatal autosomal recessive disease in Caucasians affecting approximately 1 in 2000 or 2500 live births, with 1 person in 25 being a heterozygote (Boat et al., *Metabolic Basis of Inherited Disease* 2649-2680 (McGraw-Hill, 1989)). It is a complex disorder mainly affecting the ability of epithelial cells in the airways, sweat glands, pancreas and other organs and tissues to secrete chloride ions ($Cl^-$), leading to a severe reduction of the accompanying sodium and water in the mucus. Thus, the primary defect in CF is thought to be the relative impermeability of the epithelial cell to chloride ions ($Cl^-$). This defect results in the accumulation of excessively thick, dehydrated and tenacious mucus in the airways, with subsequent bacterial infections, mucus blockage and inflammation. For a detailed discussion of the clinical manifestations, diagnosis, complications and treatment of the disease, see R. C. Bone, *Cystic Fibrosis*, In J. C. Bennett et al., *Cecil Textbook of Medicine* 419-422 (W.B. Saunders Co., 1996).

The CF Protein and Gene. The gene for CF is located on the long arm of chromosome 7. For a description of the gene, the expression of the gene as a functional protein, and confirmation that mutations of the gene are responsible for CF, see Gregory et al., *Nature* 347:382-386 (1990); Rich et al., *Nature* 347:358-363 (1990); and Watson et al., *Recombinant DNA*, pp. 525-529 (Scientific American Books, 1992).

The protein encoded by the CF-associated gene is the cystic fibrosis transmembrane conductance regulator (CFTR). CFTR is a cyclic AMP-dependent chloride channel found in the plasma membrane of certain epithelial cells. CFTR contains approximately 1480 amino acids and is made up of two repeated elements, each comprising six transmembrane segments and a nucleotide binding domain. The two repeats are separated by a large, polar, so-called k-domain containing multiple potential phosphorylation sites. Based on its predicted domain structure, CFTR is a member of a class of related proteins which includes the multi-drug resistance or P-glycoprotein, bovine adenyl cyclase, the yeast STE6 protein as well as several bacterial amino acid transport proteins (Riordan et al, *Science* 245:1066-1073 (1989); Hyde et al., *Nature* 346:362-365 (1990)). Proteins in this group are characteristically involved in pumping molecules into or out of cells.

Gene Mutations Responsible for CF. The metabolic basis for CF results from a mutational defect in a specific chloride channel. Naturally-occurring, single amino acid mutations have been found in the first nucleotide binding fold of CFTR. Although over 800 different mutations have been identified in the CF associated gene, the most common is a deletion of three nucleotides which results in the loss of a phenylalanine residue at position 508 of CFTR (ΔF508) (Davis et al., *Am. J. Respir. Crit. Care Med.* 154:1229-1256 (1996); Sheppard and Welsh, *Physiol. Rev.* 79:Suppl: S23-S45 (1999)).

Additional examples of CFTR mutants include G551D, a mutation in the CFTR gene resulting in a substitution of aspartic acid for glycine at amino acid 551 of the CFTR (U.S. Pat. No. 5,602,110), and several naturally-occurring CFTR mutants carrying a defect in the first nucleotide binding fold (NFB1) (U.S. Pat. No. 5,434,086).

Mutations at position 508 contribute to approximately 90% of all CF cases, although the percentage varies by race and geographical location (Kerem et al., *Science* 245:1073-1080 (1989)). This mutation results in the failure of an epithelial cell chloride channel to respond to cAMP (Frizzel et al., Science 233:558-560 (1986); Welsh, Science 232:1648-1650 (1986); Li et al., Science 244:1353-1356 (1989); Quinton, Clin. Chem. 35:726-730 (1989)). Although CF-affected epithelial cells are unable to normally up-regulate apical membrane Cl– secretion in response to agents which increase cAMP, they do increase Cl– secretion in response to increases in intracellular $Ca^{2+}$.

There are at least three different chloride channels found in epithelial cells, including volume sensitive, calcium-dependent and cAMP-dependent. In normal individuals, chloride channels are located on the luminal membranes of epithelial cells. When these channels are open, chloride ions move into the airway lumen, producing an osmotic gradient that draws water into the lumen. In Cystic Fibrosis, the absence or dysfunction of at least one of these chloride channels, CFTR, results in the failure to secrete chloride in response to cAMP stimulation. Therefore, there is an inadequate amount of water on the luminal side of the epithelial membranes as well as excessive sodium reabsorption. In airway cells this causes abnormal mucus secretion with inadequate water content, ultimately leading to pulmonary infection and epithelial damage. Abnormal electrolytes in the sweat of CF patients probably results from the impermeability of the sweat duct epithelium to chloride.

Physiologically, the (ΔF508) mutant CFTR is mis-folded and unable to assume its appropriate tertiary conformation (Thomas et al., J. Biol. Chem. 267:5727-5730 (1992)), is retained in the endoplasmic reticulum (ER) as a result of the mutation-induced mis-folding, and eventually is targeted for degradation (Cheng et al., Cell 63:827-834 (1990); Ward et al., Cell 83: 122-127 (1995)). Other examples of processing mutants leading to CFTR chloride channel dysfunction, with the frequency of the mutation in parentheses, include: DI507 (0.5), S549I (very rare), S549R (0.3), A559T (very rare) and N1303K (1.8) (Welsh et al., Cell 73:1251-1254 (1993)). P574H and A455E are additional CF-associated mutants which are also mis-processed (Ostedgaard et al., J. Cell. Sci. 112(Pt13):2091-2098 (1999)). Only 5% to 10% of the mis-folded CFTR protein of these two mutants reaches the apical membrane.

Because more than 98% of CF patients die from either respiratory failure or pulmonary complications before reaching maximum physiological maturity, the therapeutic goals have historically been to prevent and treat the complications of obstruction and infection in the airways, enhance mucous clearance, and improve nutrition. The identification of the ΔF508 defect (and other mutations in CFTR) has facilitated the rapid development of proposed treatments for CF, including the therapeutic introduction of the wild-type CFTR gene via gene therapy, as well as more traditional drug therapies.

C. Current and Potential Treatments for Cystic Fibrosis

Treatment of Cystic Fibrosis Using Traditional Drugs. Traditional treatments for CF include chest physiotherapy (e.g., percussion and postural drainage), various broncodilators, nutritional supplements (e.g., pancreatic enzymes and vitamins), exercise and rehabilitation, and long-term oxygen therapy for chronic hypoxemia. Aerosolized amiloride has been administered to improve the quality of the secretions, thereby improving the air flow in CF patients (U.S. Pat. Nos. 4,501,729 and 4,866,072). Although these methods have increased the overall survival and physical comfort of CF patients, the traditional drugs and treatment methodologies do not cure the afflicted individuals and CF-afflicted persons often are not expected to live beyond their mid-twenties or early thirties. (R. C. Bone, supra).

DNase Treatment. One identified new drug treatment for CF has been the use of DNase, such as human DNase X, which ameliorates one of the side effects caused by the defect in CFTR (New England Journal of Medicine 331:637-642 (1994)). Although the water content of bronchial secretions is probably the critical determinant of secretion viscosity, it is believed that DNA from lysed cells may add to this index.

Increased Permeability of Epithelial Cells to Cl⁻. U.S. Pat. No. 5,384,128 discloses a method of treating CF which comprises administration of an epithelial cell chloride permeability enhancing composition which is a nontoxic, nonionic surfactant having (1) a critical micelle concentration of less than about 10 mM and a hydrophile-lipophile balance number of from about 10 to 20, and (2) a suitable hydrophobic organic group joined by a linkage to a suitable hydrophobic polyol. Examples of such compositions include a saccharide joined with organic groupings, such as an alkyl, aryl, aralkyl, or fatty acid group; polyoxyethylenes joined with an organic grouping; or, alkyl polyoxyethylene sorbitans. The preferred method of treatment is by aerosol inhalation.

Treatment of Cystic Fibrosis Using Gene Therapy. Several methods of gene therapy have been developed and are being tested for providing the normal CFTR gene into CF patients. For example, transfecting the normal CFTR gene into the nasal epithelial cells of patients has been shown to improve functions of the transmembrane chloride channel. These results have raised the hope that delivery of retroviral vectors containing normal CFTR genes directly to the lung epithelium by means of aerosol will help alleviate CF. Despite promising results, implementation of gene therapy methodologies to "cure" CF by introducing the normal CFTR gene into CF patients still remain in the experimental stages. As a result, efficacious alternatives including drugs or alternative approaches such as siRNA therapy are needed to more effectively treat CF.

D. Chronic Obstructive Pulmonary Disease: An Overview of the Disease, Protein and Gene.

The Disease. The designation Chronic Obstructive Pulmonary Disease (COPD) is an imperfect, although widely used, term because it includes several specific disorders with different clinical manifestations, pathologic findings, therapy requirements, and prognoses. The term encompasses chronic bronchitis and emphysema. Common to most of these diseases is chronic involvement of peripheral (small) airways or, more rarely, localized obstruction of central (large) airways. For a comprehensive overview of COPD, see Matthay et al., Chronic Airways Diseases, In Cecil Textbook of Medicine (Bennet et al., eds.; W. B. Saunders Company) 20th Ed., 52:381-309 (1996)).

Since elastase released by activated neutrophils is rendered inactive by the inhibitor α-antitrypsin (AAT), diminished circulating levels of AAT can result in proteolytic destruction of lung elastin, a phenomenon implicated in the pathogenesis of COPD (Travis et al., Annu. Rev. Biochem. 52:655-709 (1983); Beith, Front. Matrix Biol. 6:14 (1978)).

The α-Antitrypsin (AAT) Protein and Gene. Human AAT is a 394-amino acid protein glycosylated at three specific asparagine residues (Carrell et al., In Proteinase Inhibitors (Barrett et al., eds.; Elsevier, Amsterdam) 403-420 (1986); Long et al., Biochemistry 23:4828-4837 (1984); Yoshida et al., Arch. Biochem. Biophys. 195:591-595 (1979)). AAT is a member of the serine proteinase inhibitor superfamily (Huber et al., Biochemistry 28:8951-8966 (1989)). It is folded into a highly ordered tertiary structure containing three β-sheets, nine α helices, and three internal salt bridges (Loebermann et al., J. Mol. Bio. 177:531-556 (1984)).

Gene Mutations Responsible for COPD. The human NAT structural gene is highly polymorphic and several alleles exhibit a distinct mutation predicted to preclude conformational maturation of the encoded polypeptide following biosynthesis (Brantly et al, *Am. J. Med.* 84:13-31 (1988); Stein et al., *Nat. Struct. Biol.* 2:96-113 (1995)). Genetic variants of human AAT unable to fold into the native structural conformation are poorly secreted from hepatocytes (Laurell et al., In *Protease Inhibitors in Plasma* (Putnam, ed.; Academic Press, New York) Vol. 1:229-264 (1975); Peters et al., In *Plasma Protein Secretion by the Liver* (Glaumann et al., eds.; Academic Press, New York) 1-5 (1983); Sifers et al., *Semin. Liver Dis.* 12:301-312 (1992); Sifers et al., In *The Liver: Biology and Pathology* (Arias et al., eds.; Raven Press Ltd., New York) 3rd Ed. 1357-1365 (1994)).

Choudhury et al. (*J. Biol. Chem.* 272(20):13446-13451 (1997)) report on a secretion-incompetent variant null of α-antitrypsin designated as Hong Kong.

SUMMARY OF THE INVENTION

E. Overview of the Invention.

The current invention is based on the unexpected discovery that inhibition of UGGT or other elements of the ER-chaperon retention machinery allows mis-folded or mis-assembled proteins, such as mis-folded mutant (ΔF508) CFTR protein and mutant α-antitrypsin (Hong Kong), to exit the ER instead of being targeted for degradation. By preventing the normal action of UGGT and/or other elements of the ER-chaperon retention machinery, the mis-folded proteins exit the ER and are targeted to the plasma membrane, where despite the mutation, they can function. This invention has practical applications in treating or curing any disorder or disease which directly or indirectly results from mis-folded ER proteins including, but not limited to, clinical conditions related to the misfolding and/or non-release of the transmembrane precursors of the glycosylphosphatidylinositol-linked proteins, low density lipoprotein receptor, the thyroid prohormone thyroglobulin (Tg), Class I histocompatibility proteins as occurs in tumors and in numerous viral infections, as well as CFTR and α-antitrypsin.

Our approach is the first to attempt to defeat ER retention of mis-folded proteins by interfering directly with ER quality control mechanisms. As described in detail herein, this invention encompasses various compositions and methods which reduce the activity of any ER chaperone including, but not limited to, UGGT and thereby permit exiting of mis-folded and mis-assembled proteins from the ER. Such compositions include compounds which covalently bond to modified UGGT and irreversibly inhibit its catalytic function. Exposure to oligonucleotides whose sequences are antisense to the UGGT coding sequence or to siRNA molecules targeted to the UGGT transcript will also reduce UGGT expression and activity. Optimal UGGT activity requires high concentrations of $Ca^{2+}$. Our research also demonstrates that depleting ER $Ca^{2+}$ stores through various treatments, such as with calcium pump inhibitors, allows the mis-folded but functional ΔF508 CFTR protein to "escape" from the ER and reach the cell surface, possibly by interfering with the activity of chaperones such as UGGT. Thus, our discovery also provides novel and clinically applicable treatment for reversing or preventing diseases or clinical conditions which result from the ER-associated retention or degradation of mis-assembled or mis-folded proteins.

The invention provides methods and reagents for treating any disease or clinical condition by administering an agent that permits the release of proteins from the ER. More particularly, this invention provides such methods wherein the disease or clinical condition is at least partly the result of endoplasmic reticulum-associated retention or degradation of mis-assembled or mis-folded proteins.

In one embodiment of the invention, methods are provided wherein the agent permits release of mis-assembled or mis-folded proteins from the endoplasmic reticulum. Preferably the mis-assembled or mis-folded proteins retain sufficient activity to relieve at least some of the symptoms of the disease or clinical condition.

In another embodiment of the invention, methods are provided wherein the proteins being released are glycoproteins.

The methods of the present invention are useful for treating diseases or clinical conditions such as Cystic Fibrosis, Chronic Obstructive Pulmonary Disease, Paroxysmal Nocturnal Hemoglobinuria, Familial Hypercholesterolemia, Tay-Sachs Disease, viral diseases, neoplastic diseases, Hereditary Myeloperoxidase Deficiency, Congenital Insulin Resistance, Rhinosinusitis, Hemochromatosis, Gitelman's Syndrome, Cystinuria, and certain forms of Nephrogenic Diabetes Insipidus.

In one embodiment of the invention, the methods involve using agents which act as calcium pump inhibitors.

In another embodiment of the invention, the methods involve using agents which decrease or inhibit the functional activity of UDP glucose:glycoprotein glycosyl transferase.

In still another embodiment of the invention, the methods involve using agents that decrease or inhibit activity of the endoplasmic reticulum $Ca^{++}$ ATPase.

In yet another embodiment of the invention, the methods involve using agents that lower the concentration of $Ca^{++}$ in the endoplasmic reticulum.

In another embodiment of the invention, the methods involve using agents that cause release of $Ca^{++}$ from the endoplasmic reticulum.

In yet another embodiment of the invention, the methods involve using agents that increase or stimulate $IP_3$ receptor activity.

In yet another embodiment of the invention, the methods involve using agents that increase or stimulate ryanodine receptor activity.

In still another embodiment of the invention, the methods involve using agents that decrease or inhibit calnexin functional activity.

Examples of agents which are useful in the methods of the present invention include, but are not limited to, thapsigargin or a derivative thereof, cyclopiazonic acid or a derivative thereof, DBHQ or a derivative thereof, curcumin, curcumin related compounds, or an analog or derivative of curcumin, or halothane or a derivative thereof.

Additional examples of agents that are useful in the methods of the present invention include, but are not limited to, oligonucleotides which are antisense to UDP glucose:glycoprotein glycosyl transferase, calnexin, ER $Ca^{++}$ ATPase, or any chaperone involved in the retention of a misfolded or misassembled protein in the ER, which retention is associated with a disease or clinical condition.

Additional examples of agents that are useful in the methods of the present invention include, but are not limited to, siRNAs that are targeted to ER $Ca^{++}$ ATPase, UDP glucose:glycoprotein glycosyl transferase, calnexin, or any chaperone involved in the retention of a misfolded or misassembled protein within the ER, which retention is associated with a disease or clinical condition.

The present invention also provides methods wherein the agents are administered to the pulmonary system, such as by using an aerosol.

The present invention provides methods of releasing a mis-assembled or mis-folded glycoprotein from the endoplasmic reticulum of a cell by administering an agent that decreases or inhibits the functional activity of UDP glucose: glycoprotein glycosyl transferase.

The present invention also provides methods of releasing a mis-assembled or mis-folded protein from the endoplasmic reticulum of a cell by administering an agent that decreases or inhibits activity of the endoplasmic reticulum $Ca^{++}$ ATPase.

The present invention also provides methods of releasing a mis-assembled or mis-folded protein from the endoplasmic reticulum of a cell by administering an agent that lowers the concentration of $Ca^{++}$ in the endoplasmic reticulum.

The present invention also provides methods of releasing a mis-assembled or mis-folded protein from the endoplasmic reticulum of a cell by administering an agent that decreases or inhibits calnexin functional activity.

The present invention also provides methods of increasing the permeability of the apical surfaces of airway epithelial cells to a chloride ion by administering an agent that decreases or inhibits the intracellular retention of mis-assembled or mis-folded proteins.

The present invention further provides methods of increasing the permeability of the apical surfaces of airway epithelial cells to a chloride ion by administering an agent that decreases or inhibits the activity of UDP glucose:glycoprotein glycosyl transferase.

The present invention also provides methods of increasing the permeability of the apical surfaces of airway epithelial cells to a chloride ion by administering an agent that decreases or inhibits activity of the endoplasmic reticulum $Ca^{++}$ ATPase.

The present invention further provides methods of increasing the permeability of the apical surfaces of airway epithelial cells to a chloride ion by administering an agent that lowers the concentration of $Ca^{++}$ in the endoplasmic reticulum.

The present invention also provides methods of increasing the permeability of the apical surfaces of airway epithelial cells to a chloride ion by administering an agent that decreases or inhibits calnexin functional activity.

The present invention further provides methods of treating cystic fibrosis or alleviating the symptoms of cystic fibrosis by administering an agent that decreases or inhibits the activity of UDP glucose:glycoprotein glycosyl transferase.

The present invention also provides methods of treating cystic fibrosis or alleviating the symptoms of cystic fibrosis by administering an agent that decreases or inhibits activity of the endoplasmic reticulum $Ca^{++}$ ATPase.

The present invention further provides methods of treating cystic fibrosis or alleviating the symptoms of cystic fibrosis by administering an agent that lowers the concentration of $Ca^{++}$ in the endoplasmic reticulum.

The present invention further provides methods of treating cystic fibrosis or alleviating the symptoms of cystic fibrosis by administering an agent that decreases or inhibits calnexin functional activity.

The present invention provides methods of screening candidate compounds to identify an agent that inhibits endoplasmic reticulum-associated retention or degradation of a mis-assembled or mis-folded protein, wherein the method includes the steps of:
   a) treating a cell exhibiting intracellular retention of a mis-assembled or mis-folded protein in the endoplasmic reticulum with the candidate compound; and
   b) determining whether the mis-assembled or mis-folded protein is released from the endoplasmic reticulum, thereby identifying the candidate compound as an agent that causes the release of a malformed or mis-folded protein from the endoplasmic reticulum. In certain embodiments of the invention the mis-assembled or mis-folded protein is a glycoprotein.

The present invention also provides methods of screening candidate compounds to identify an agent that inhibits the functional activity of UDP glucose:glycoprotein glycosyl transferase, wherein the method includes the steps of:
   a) treating a cell exhibiting intracellular retention of a mis-assembled or mis-folded protein in the endoplasmic reticulum with the candidate compound; and
   b) determining whether the mis-assembled or mis-folded protein is released from the endoplasmic reticulum, thereby identifying the candidate compound as an agent that causes the release of a mis-assembled or mis-folded protein from the endoplasmic reticulum.

The invention also provides aerosol formulations of thapsigargin, DBHQ, cyclopiazonic acid, or curcumin and also provides aerosol formulations of related compounds, analogs, or derivatives of the foregoing compounds.

In addition, the present invention provides compositions which include two or more of the following agents: 1) an agent that decreases or inhibits the activity of UDP glucose: glycoprotein glycosyl transferase, 2) an agent that decreases or inhibits activity of the endoplasmic reticulum $Ca^{++}$ ATPase, 3) an agent that increases or stimulates $IP_3$ receptor activity, 4) an agent that increases or stimulates ryanodine receptor activity, 5) an agent that decreases or inhibits calnexin functional activity, and 6) an agent that decreases or inhibits activity of a chaperone involved in retention of a misfolded or misassembled protein within the ER, which retention is associated with a disease or clinical condition.

DESCRIPTION OF THE DRAWING

FIG. 1. CFTR chloride channel activity in excised patches from CF-affected airway epithelial cells in control conditions or after treatment with thapsigargin. Cells were pretreated with IBMX (100 μM) and forskolin (10 μM) prior to patch excision. Initially patches were held at −50 mV, and then stepped through a voltage protocol from ±10 mV to ±90 mV. 1 mM ATP was present in the bath to prevent channel rundown.

A. Representative single channel current traces from a membrane patch excised from untreated IB3-1 cells. No low conductance chloride channel activity was seen. Arrows indicate closed state.

B. Representative single channel currents from a membrane patch excised from an 1B3-1 cell after treatment with thapsigargin. Low conductance chloride channel activity can be seen as the downward deflections in the current traces. Arrows indicate closed state.

FIG. 2. Characteristics of CFTR channels in CF-affected airway epithelial cells after thapsigargin treatment.

A. The current versus voltage relationship of the low conductance channels depicted in FIG. 1B is plotted. The average single channel conductance was 11.8 pS.

B. All points histogram at +80 mV. The area under the first peak represents time spent in the closed state, while the area under the second peak represents time spent in the open state. The calculated open state probability is 0.12.

FIG. 3. The effects of elevation of cytosolic cAMP on short circuit current. Monolayers of CFPAC or T84 cells were exposed to a cAMP-stimulation cocktail of 10 M forskolin and 100 M IBMX. The bars indicate the % increase in $I_{sc}$ that is furosemide sensitive detected after treatment with the cAMP stimulation cocktail. The asterisks mark a significant difference between untreated CFPAC cells (n=12) and either the thapsigargin treated CFPAC cells (p=0.02, *) (n=12) or the T84 cells (p=0.004. **) (n 12). Error Bars=SEM.

FIG. 4. Confocal immunofluorescent localization of the mutant ΔF508 CFTR protein in untreated and thapsigargin-treated CFPAC cells. Untreated CF-PAC cells or CF-PAC cells which had been treated with thapsigargin were subjected to confocal immunofluorescence labeling using an antibody directed against the CFTR protein.

When viewed en face (A) or in XZ cross-section (C), the untreated cells revealed a staining pattern consistent with an exclusively intracellular localization of the CFTR protein. No cell surface labeling could be detected. In contrast, thapsigargin-treated cells viewed en face (B) in XZ cross-section (D) reveal bright staining of microvili at the apical plasma membrane. The intracellular signal is markedly diminished in the treated cells. Thus, thapsigargin treatment induces the relocalization of the ΔF508 mutant CFTR protein from an intracellular compartment to its site of appropriate functional residence at the apical cell surface. The width of the monolayer is 11µ.

FIG. 5. Distribution of the ΔF508 CFTR protein in CFBE290− CF airway epithelial cells exposed to nebulized thapsigargin. CFBE290− airway epithelial cells were grown to confluence on permeable filter supports. Cells were exposed to thapsigargin dissolved in the media bathing their apical surfaces (A,B), to nebulized thapsigargin (E,F) or were not thapsigargin-treated (C,D) and processed for immunofluorescence. Panels A, C and E depict the immunofluorescent staining of the ΔF508 CFTR protein; panels B, D and F depict the basolateral localization of the Na,K-ATPase-subunit. The ΔF508 CFTR protein can not be detected in untreated cells, but is present to the same extent at the apical surfaces of cells treated with nebulized or dissolved thapsigargin. The width of the monolayer is 9 u.

Figure 6:
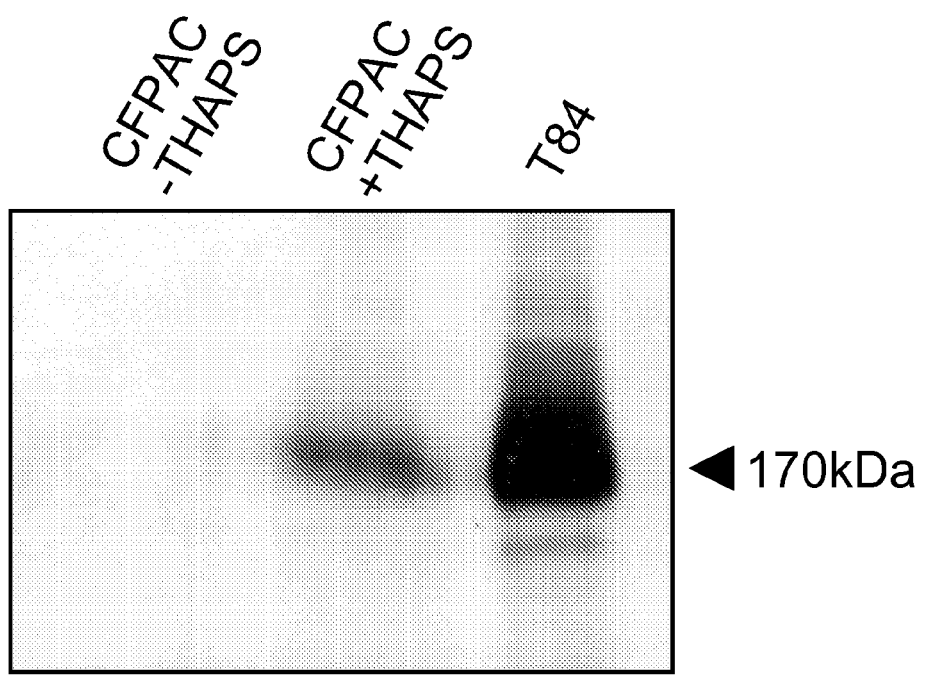

FIG. 6. Western blot showing presence of mature CFTR in thapsigargin treated but not untreated CFPAC cells.

Figure 7:
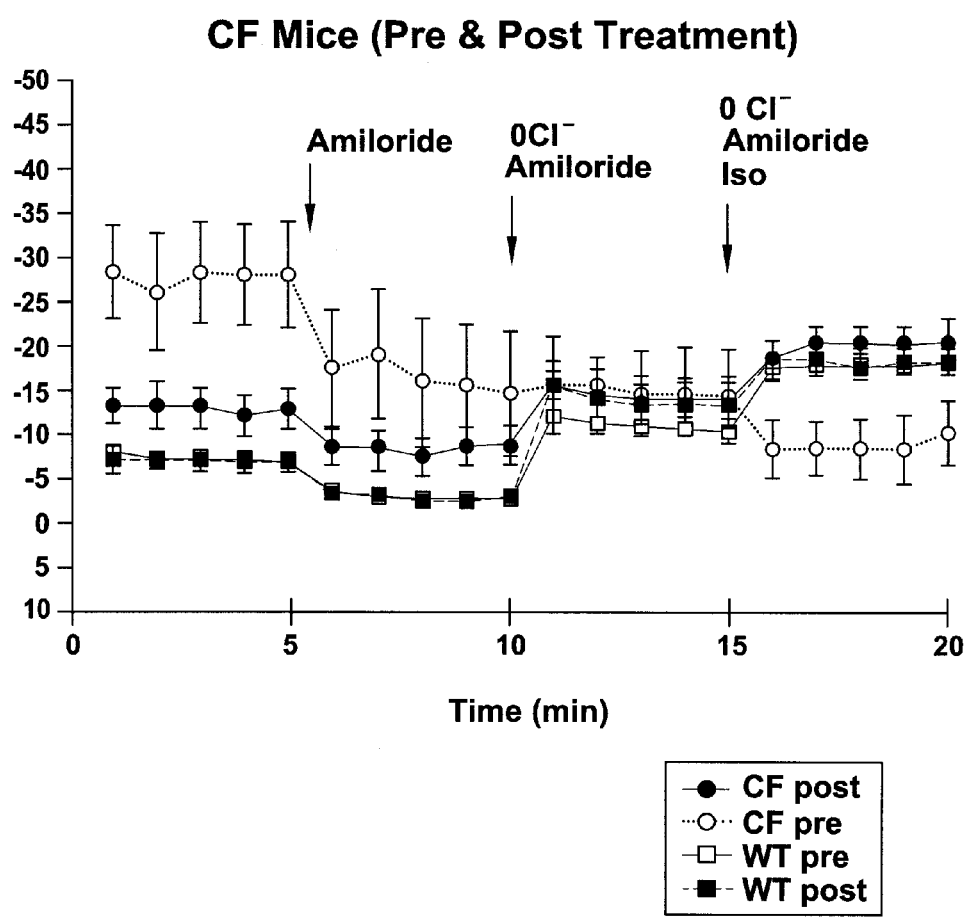

FIG. 7. Tracing of transnasal electrical potential (NPD) difference in normal and CF mutant mice homozygous for the ΔF508 mutation. The tracing represents the time course of the NPD protocol and the response of NPD readings to perfusion with control Ringer solution, Ringer solution with amiloride, low chloride with amiloride, and the addition of isoproterenol to the low chloride solution. For the wild type group CF group, n=4-6 animals. Legend: open squares=untreated wild type mice; filled squares=thapsigargin-treated wild type mice; open circles=untreated CF mutant mice; filled circles=thapsigargin-treated CF mutant mice.

Figure 8A:
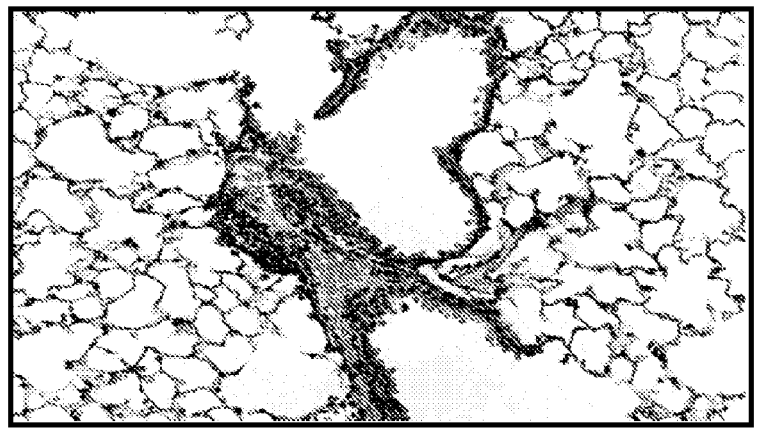
Figure 8B:
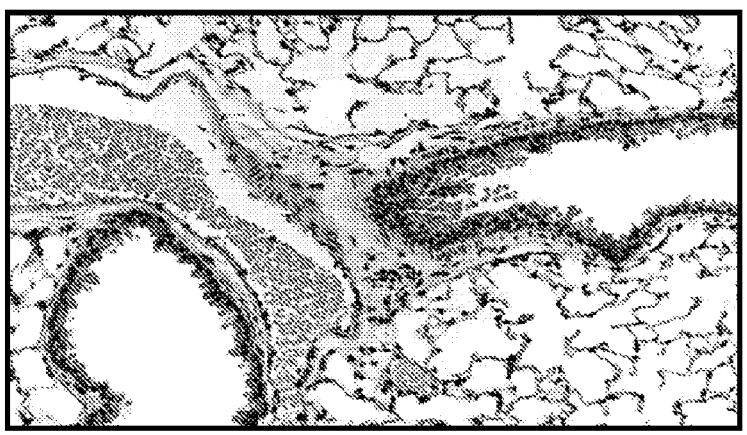
Figure 8C:
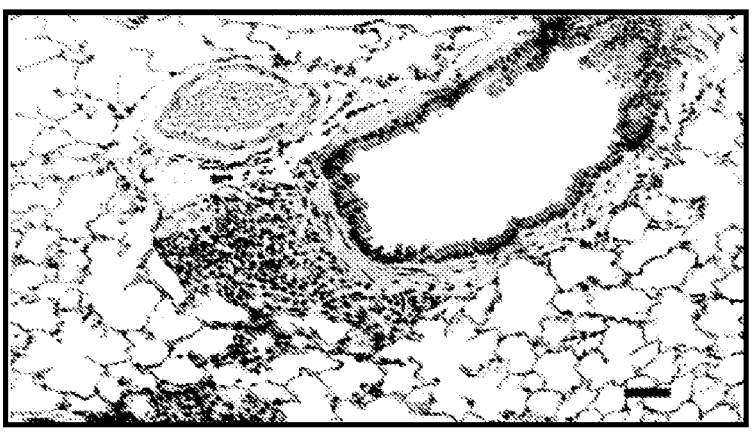

FIG. 8: Histologic appearance of lung tissue from control and thapsigargin-treated wild type mice. Sections of lung tissue from untreated (A) and thapsigargin-treated (B and C) mice were stained with hematoxylin and eosin. The scale bar in panel C=280µ.

FIG. 9. Immunolocalization of the mutant Delta F508 CFTR protein in untreated and curcumin-treated Delta F508 CFTR-expressing CHO cells. CHO cells expressing Delta F508 CFTR by transfection were grown to confluence on glass coverslips. Cells were exposed to curcumin dissolved in the media (C,D), or were not curcumin-treated (A,B) and processed for immunofluorescence using a monoclonal antibody directed against the CFTR C-terminus. The images are en face views. The Delta F508 CFTR protein can not be detected at the plasma membrane in untreated cells, localizing instead to the ER. The plasma membranes of curcumin-treated cells are brightly labeled by the antiCFTR antibody.

Figure 10:
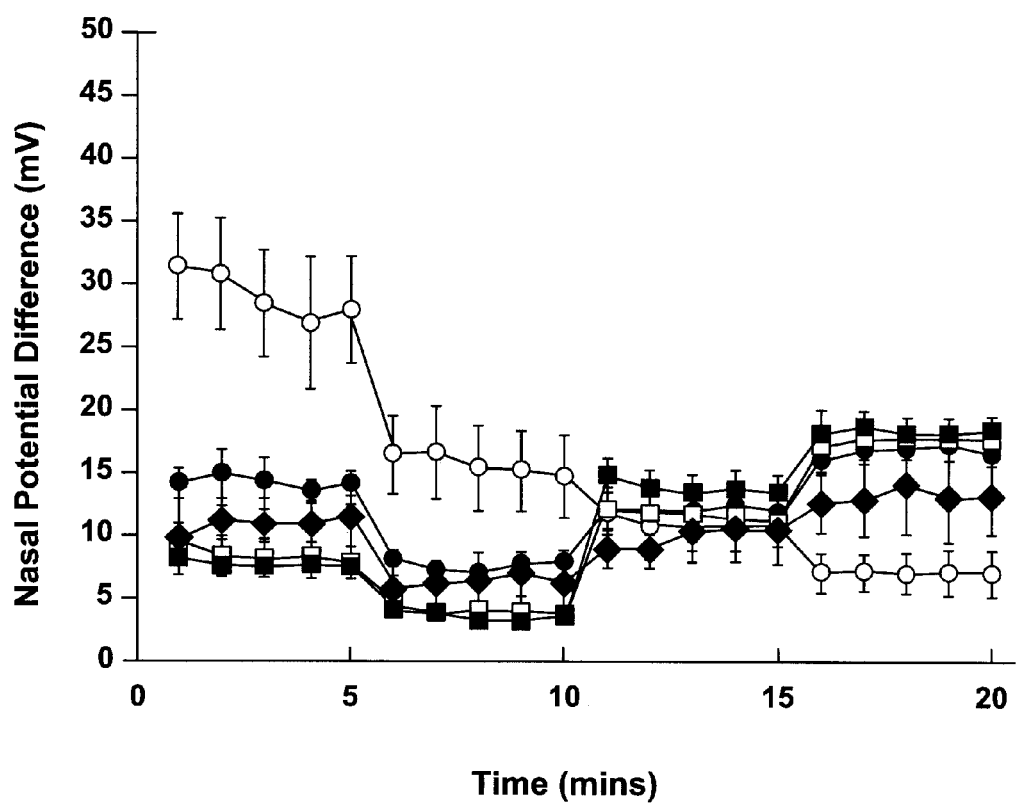

FIG. 10. Tracing of transnasal electrical potential (NPD) difference in normal and CF mutant mice homozygous for the ΔF508 mutation under various treatment conditions. The tracing represents the time course of the NPD protocol and the response of NPD readings to perfusion with control Ringer solution, Ringer solution with amiloride, low chloride with amiloride, and the addition of isoproterenol to the low chloride solution. Each data point represents an average of results obtained using groups of animals. Error bars represent standard error. Squares represent wild type mice that were either untreated (open squares) or thapsigargin treated (closed squares). Circles represent ΔF508 CFTR mice that were either untreated (open circles) or thapsigargin treated (closed circles). Diamonds represent ΔF508 CFTR mice treated with nebulized curcumin. N=7 for the wild type untreated and treated groups. N=10 for the ΔF508 CFTR untreated and thapsigargin treated groups. N=6 for the ΔF508 CFTR curcumin treated group.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, certain of the preferred methods and materials are described.

A. DEFINITIONS

Antisense. The term "antisense", as used herein, refers to nucleotide sequences that are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

Clinical Condition. Any symptom or disorder related to any disease.

Combinatorial Chemistry. "Combinatorial chemistry," as used herein, refers to the numerous technologies used to create hundreds or thousands of chemical compounds, wherein each of the chemical compounds differ for one or more features, such as their shape, charge, and/or hydrophobic characteristics.

Disease. A pathological condition of a cell, body part, an organ, a tissue, or a system resulting from various causes, wherein such causes include, but are not limited to, infections, genetic defects or environmental stresses.

Mis-assembled. As used herein, "mis-assembled" refers to hetero or homo-oligomeric proteins that have not or can not attain their appropriate or functionally mature quaternary structure and/or to hetero- or homo-oligomeric proteins that have a three-dimensional structure different to wild type that causes retention in the ER or in an ER-Golgi compartment.

Mis-folded. As used herein, "mis-folded" refers to proteins that have not or can not attain their appropriate or functionally mature tertiary structure and/or to hetero- or homo-oligomeric proteins that have a three-dimensional structure different to wild type that causes retention in the ER or in an ER-Golgi compartment.

Nebulized. As used herein, "nebulized" refers to converting a liquid to a fine spray. A medicated spray is one form of the nebulization of a liquid.

Nucleic Acid Sequence. "Nucleic acid sequence," as used herein, refers to an oligonucleotide, nucleotide, or polynucleotide, and fragments or portions thereof, and to DNA or RNA of genomic or synthetic origin which may be single- or double-stranded, and represents the sense or antisense strand. Similarly, "amino acid sequence" as used herein refers to an oligopeptide, peptide, polypeptide, or protein sequence, and fragments or portions thereof, and to naturally occurring or synthetic molecules.

siRNA. A short, interfering RNA (siRNA) comprises an RNA duplex that is approximately 19 basepairs long and optionally further comprises one or two single-stranded overhangs or loops. An inventive siRNA may comprise two RNA strands hybridized together, or may alternatively comprise a single RNA strand that includes a self-hybridizing portion. When siRNAs utilized in accordance with the present invention include one or more free strand ends, it is generally preferred that free 5' ends have phosphate groups, and free 3' ends have hydroxyl groups. Inventive siRNAs include a portion that hybridizes under stringent conditions with a target transcript. In certain preferred embodiments of the invention, one strand of the siRNA (or, the self-hybridizing portion of the siRNA) is precisely complementary with a region of the target transcript, meaning that the siRNA hybridizes to the target transcript without a single mismatch. In most embodiments of the invention in which perfect complementarity is not achieved, it is generally preferred that any mismatches be located at or near the siRNA termini.

Targeted. An siRNA is considered "targeted" for the purposes described herein if 1) the stability of the target gene transcript is reduced in the presence of the siRNA as compared with its absence; and/or 2) the siRNA shows at least about 90%, more preferably at least about 91%, 92%, 93%, 94%, 95%, 96%, 97%, 98%, 99%, or 100% precise sequence complementarity with the target transcript for a stretch of at least about 17, more preferably at least about 18 or 19 to about 21-23 nucleotides; and/or 3) the siRNA hybridizes to the target transcript under stringent conditions appropriately selected for RNA oligonucleotide hybridization to a target sequence.

Treating. As used herein, "treating" includes reversing, alleviating, inhibiting the progress of, preventing, or reducing the likelihood of the disease, disorder, or condition to which such term applies, or one or more symptoms or manifestations of such disease, disorder or condition.

UGGT. As used herein, "UGGT" refers to UDP-Glc:glycoprotein glycosyl transferase, also known as UDP glycoprotein glycosyl transferase and as UDP-glucose:glycoprotein glucosyl transferase. UGGT is an FR enzyme that attaches glucose to malformed/improperly folded glycoproteins, but not to wild type glycoproteins.

B. Elevation of Cyclic Amp Levels

As discussed above, CFTR is a cAMP-dependent chloride channel. Cyclic AMP is composed of adenosine monophosphate with the phosphate group bonded internally to form a cyclic molecule. Cyclic AMP (cAMP) is generated from adenosine triphosphate (ATP) by the enzyme adenylcyclase and is active in the regulation of gene expression of both prokaryotes and eukaryotes.

Administration of compositions that increase or supplement the cAMP levels of epithelial cells has been used in an attempt to activate Cl$^-$ conductance to near wild type levels (U.S. Pat. No. 5,434,086). A preferred compound for increasing cAMP levels is a phosphodiesterase inhibitor, such as methylxanthine phosphodiesterase inhibitor. Phosphodiesterase inhibitors increase cAMP levels by inhibiting cAMP breakdown. Other examples of phosphodiesterase inhibitors include nonspecific inhibitors such as alkylxanthines and cAMP-specific inhibitors such as Rolipram (Shearing AG). Preferred alkylxanithines include the methylxantlunes, such as 3-isobutyl-1-methylxanthine (IBMX) and 1,3-dimethylxanthine (theophylline) and other xanthines such as papaverine, pentoxifilline and caffeine. For a review of phosphodiesterase inhibitors, see Nicholson et al., *Trends Pharmacol. Sciences* 12:19 (1991) and Beavo et al., *Trends Pharmacol. Sciences* 11:150 (1990).

Treating $\Delta$F508-C127 cells and human $\Delta$F508 airway epithelial cells with a carboxylic acid or a carboxylate, such as butyrate (e.g., sodium butyrate), resulted in the generation of cAMP-dependent chloride channel activity (U.S. Pat. No. 5,674,898).

Supplemental cAMP and analogs thereof or beta andrenergic receptor agonists, such as isoproterenol and albuterol, can also be used to increase cAMP levels.

Guanosine monophosphate (GMP) becomes a cyclic molecule by a phosphodiester bond between the 3' and 5' atoms. Cyclic GMP (cGMP) acts at the cellular level as a regulator of various metabolic processes, possibly as an antagonist to cAMP.

Combination therapy that includes administration of an inhibitor specific for a cGMP-inhibited type III cAMP phosphodiesterase, an adenylate cyclase activator, and a cAMP or a cAMP analog has also been proposed for treating CF (U.S. Pat. No. 5,602,110). Inhibitors which are specific for a cGMP-inhibited type III cAMP phosphodiesterase include amrinone, milrinone, anagrelide, cilostamide and fenoxamine. Adenylate cyclase activators include forskolin, cholera toxin and beta-adrenergic receptor agonists.

C. Calcium-ATPase Inhibitors

Correct distribution of $Ca^{+2}$ ions within the cellular compartments is required for their well-established function as molecular signals in eukaryotic cells (Cheek, T. R., *Curr. Opin. Cell. Biol.* 3:199-205 (1991); Pietrobon et al., *Eur. J. Biochem.* 193:599-622 (1990)). ATP-dependent $Ca^{+2}$ uptake from the cytosol to ER lumen is a prerequisite for rapid cytostolic signaling through receptor-mediated $Ca^{+2}$ release (Berridge, M. J., *Nature* 361:315-325 (1993)).

The ATP-requiring $Ca^{+2}$ transport to the ER lumen is accomplished by a family of ER $Ca^{+2}$ ATPases termed SERCA ATPases. $Ca^{+2}$-ATPase inhibitors may be therapeutically useful in treating CF by improving Cl$^-$ secretion in epithelial cells. Proposed $Ca^{+2}$-ATPase inhibitors for use in the present invention, include, but are not limited to, thapsigargin, cyclopiazonic acid (CPA), 2,5-di-(tert-butyl)-1,4-hydroquinone (DBHQ) (A. C. Chao et al., *J. Clin. Invest.* 96(4): 1794-1801 (1995) and U.S. Pat. No. 5,384,128), and curcumin. Thapsigargin is described in more detail below. CPA is an indole derivative isolated from liquid cultures of *Penicillium cyclopium, Aspergillis flavus* and *Aspergillis versicolor* (Luk et al., *Applied and Environmental Microbiology* 211-212 (1977)). DBHQ is a commercially available nontoxic synthetic compound chemically unrelated to either thapsigargin or CPA. Curcumin is described in further detail below.

Using the CF-derived pancreatic epithelial line CFPAC-1, Chao et al., supra, found that DBHQ stimulated $^{125}$I efflux and mobilized intracellular free $Ca^{+2}$ in a dose-dependent manner. Pretreatment of monolayers of CFPAC-1 cells with DBHQ for 4-5 minutes significantly increased the $C^{+2}$-independent or autonomous activity of $Ca^{+2}$/calmodulin-dependent protein kinase (CaMKII) assayed in cell homogenates.

D. Opening the Er $Ca^{+2}$ Channels

Activators which lower ER $Ca^{+2}$ by a different mechanism than thapsigargin are also encompassed by this invention.

1D-myo-inositol 1,3,4-(or 1,4,5-) triphosphate ($IP_3$), a hydrophilic inositol phosphate, induces the intracellular release of $Ca^{+2}$ stores from the ER through its specific interactions with the $IP_3$ receptor (e.g., a calcium channel protein containing an $IP_3$ binding site). Thus, the present invention also encompasses agents that open ER $Ca^{+2}$ channels by acting as $IP_3$ receptor agonists. Adenophostin A is one example of an activator of $IP_3$ receptor activity (Adkins C E, Wissing F, Potter B V, Taylor C W, Rapid activation and partial inactivation of inositol trisphosphate receptors by adenophostin A, *Biochem J.,* 352 (3): 929-33, 2000).

A determination of $IP_3$ concentration in cell extracts can be carried out by means of a sensitive competitive binding test using an $IP_3$ binding protein, $H^3$-labeled $IP_3$ and unlabeled $IP_3$ (U.S. Pat. No. 5,942,493). An assay kit for this purpose is available from Amersham (TRK 1000) and the determination can be carried out as described in the assay protocol.

Another calcium channel found in the ER is known as the ryanodine receptor (RyR). Mammalian tissues express three different RyR isoforms comprising four 560 kD (RyR polypeptide) and four 12 kD (FK506 binding protein) subunits (reviewed in Shoshan-Barmatz, V. and Ashley, R. H., The structure, function, and cellular regulation of ryanodine-sensitive $Ca^{2+}$ release channels, *Int Rev Cytol,* 183: 185-270, 1998.) Ryanodine receptors have been detected in the lung (Wild, J. S., Giri, S. N., Moore, R., and Pessah, Characterization of [$^3$H]ryanodine binding sites in mammalian lung, *Arch. Biochem Biophys.,* 379(1):109-18, 2000). According to the present invention, treatments that activate or stimulate ryanodine receptors may be effective in reducing ER $Ca^{2+}$ concentration in airway epithelial cells. Thus, the present invention also encompasses agents that increase or stimulate ryanodine receptors, thereby increasing $Ca^{2+}$ exit from the ER. Such agents include, for example, ryanodine receptor agonists, compounds that increase expression of ryanodine receptors, etc. Approaches to modulation of ryanodine receptors are discussed in Xu, L., et al., Potential for pharmacology of ryanodine receptor/calcium release channels, *Ann NY Acad Sci,* 853:130-48, 1998. Examples of agents that have been shown to increase or stimulate ryanodine receptor activity include, but are not limited to, ryanodine (in particular concentrations known in the art) and related plant alkaloids, xanthines, 4-Chloro-m-cresol, suramin, and ditalis glycosides. Such agents, and derivatives thereof (e.g., pharmaceutically acceptable derivatives), may be used in the practice of the invention.

E. Temperature-Dependent Delivery of the Mutant CFTR to the Plasma Membrane

Experiments with 3T3 fibroblast cells and C127 cells grown at lower temperatures for a period of time have shown a shift in the glycosylation pattern of Δ508 CFTR towards a more mature CFTR protein. Normal CFTR protein appears to be unaffected by the lower temperature. It has been hypothesized that at reduced temperatures there is an increased flux of the mutant protein through the Golgi complex. Thus, it has been suggested that exposing a patient's lung epithelia to a temperature below normal body temperature for a period of time might mobilize mutant CFTR to the plasma membrane of the lung epithelial cells, where the mutant CFTR can mediate chloride transport (U.S. Pat. No. 5,674,898). One hypothetical method involves implanting in the patient's lung a non-toxic, non-immunogenic agent which lowers the temperature in the vicinity of the lung so that it is below normal body temperature.

F. Purinergic Receptors and Cl$^-$ Secretion

Purinergic receptors play an important role in regulating Cl$^-$ secretion in epithelial cells. Inoue et al. (*Am. J. Physiol. Cell Physiol.* 272(6):41-46 (1997)) assayed the human intestinal epithelial cell line, Caco-2, for Cl$^-$ secretion by measuring the short-circuit current. The researchers found that responses to purinergic receptor agonists were inhibited by pretreatment with 1,2-bis(2-aminophenoxy)ethane-N,N,N', N'-tetraacetic acid-acetoxymethyl ester, thapsigargin or quinine.

G. CF and UDP-Glucose-Glycoprotein Glycosyl Transferase

As discussed above, the primary lesion in cystic fibrosis is associated with mutations in the gene encoding the CFTR which prevent it from functioning as a chloride channel at the apical surfaces of airway epithelial cells. The most common mutation (ΔF508), which occurs in 67.2% of cystic fibrosis patients, results in the synthesis of a CFTR protein which is unable to fold correctly and assume its appropriate tertiary conformation. Consequently, the protein is retained in the ER by the ER's "quality control" machinery. Several other CFTR mutations also result in mis-folding and ER retention.

Both nascent α1-antitrypsin and nascent CFTR form transient associations with calnexin (also designated as p88 or IP90), a calcium-binding protein of the ER membrane. Since calnexin functions as a molecular chaperone for glycoproteins and interacts with monoglucosylated oligosaccharides, reglucosylation may function to initiate assembly between unfolded glycoproteins and the molecular chaperone (Hammond et al., *Proc. Natl. Acad. Sci. U.S.A.* 91:913-917 (1994)).

The UGGT Protein and Gene. UGGT was found to have an apparent monomeric $M_f$ of 150 kDa following isolation and purification from rat liver microsomes (Trombetta et al., *J. Biol. Chem.* 267:9236-9240 (1992)). The soluble, 170 kDa UGGT isolated from *Drosophila* has an amino acid sequence of 1548 amino acids beginning with a signal peptide and terminating in a potential ER retrieval signal, HGEL (C. G. Parker et al., *EMBO J.* 14(7):1294-1303 (1995)). The amino acid sequence was found to lack any putative transmembrane domains. The gene coding for UGGT, designated as gpt1, has also been identified in *Schizosaccharomyces pombe* (Fernandez et al., *EMBO J.* 15(4):705-13 (1996)). This gene codes for a polypeptide having a signal peptide of 18 amino acids followed by 1429 amino acids with no transmembrane domain and a C-terminal tetrapeptide designated PDEL.

Functional Role of UGGT. UGGT adds glucose from UDP-glucose to high mannose glycoproteins in the presence of $Ca^{2+}$ ions and the resulting glucosylated oligosaccharide has the same structure as the processed intermediate, $Glc_1Man_9GlcNAc_2$ (Trombetta et al., *Biochemistry* 28:8108-8116 (1989)). Unfolded, denatured glycoproteins are substantially better substrates for glycosylation by the enzyme than are the corresponding native proteins.

Proteins that fail to fold properly are retained in the ER (or in an ER-Golgi intermediate compartment), where they are proteolytically degraded. UGGT is proposed to be involved in the quality control of glycoprotein folding in the ER (Parker et al., supra; Fernandez et al., supra; M. C. Sousa and A. J. Parodi, The interaction of UDP-Glc:Glycoprotein Glucosyl transferase with the acceptor glycoprotein, *Cellular and Molecular Biology* 42: 609-616 (1996); Sousa M C and Parodi A J. The molecular basis for the recognition of mis-folded glycoproteins by the UDP-Glc: Glycoprotein Glucosyl transferase, *EMBO J* 14: 4196-4203 (1995)). UGGT participates together with lectin-like chaperones that recognize monoglucosylated oligosaccharides in the control mechanism by which cells only allow passage of properly folded glycoproteins to the Golgi apparatus (Labriola et al., *J. Cell Biol.* 130(4):771-9 (1995)).

Cycles of transient interaction with UGGT, each resulting in reglucosylation of attached oligosaccharides, is believed to facilitate interaction between unfolded glycoproteins and calnexin and ensure the intracellular retention of improperly folded glycoproteins in the ER. Calnexin binds to glucose residues which are exposed on the N-linked sugar chains of membrane proteins.

It has been shown that UGGT requires millimolar calcium concentrations for optimal activity (Trombetta and Parodi, 1992). In cells expressing wild type α1-antitrypsin, treatment with thapsigargin retards or prevents the secretion of the protein (Kuznetsov et al., 1993; Lodish and Kong, 1990). This is apparently due to stable association of the newly synthesized α1-antitrypsin with UGGT in the endoplasmic reticulum when calcium levels in the ER are reduced (Choudhury et al., 1997). It has also been shown that lowering ER calcium through application of thapsigargin or calcium ionophores retards the exit of numerous wild type proteins from the ER and increases their rate of degradation (Wilkstrom and Lodish, 1993; Sudbeck et al., 1997; van Weering et al. 1998; Clark et al., 1994; Wong et al., 1993; Wileman et al., 1991; Lodish et al., 1992; Lodish and Kong, 1990). While not wishing to be bound by any theory, it may be the case that if the UGGT enzyme is denied calcium, it binds tightly to its substrates (i.e. newly synthesized glycoproteins) but is unable to release them, perhaps because successful completion of the glucose transfer step is required to effect release. Of course retention of misfolded proteins may occur through any of a number of other mechanisms.

It is interesting to speculate why, in the case of α1-antitrypsin, thapsigargin retards protein exit from the ER, whereas in the case of ΔF508 CFTR exit from the ER is stimulated by this drug (see Examples 1-8). Without wishing to be bound by any theory, we propose that in cells expressing a mutant protein that is incapable of proper folding, mis-folded protein is present in the ER in quantities which constitute a large molar excess over the resident quantity of UGGT. Under normal circumstances, the mis-folded protein binds to UGGT, undergoes addition of a glucose residue and is rapidly released (Hammond and Helenius, 1995). The glucosylated protein is retained in the ER via interactions with calnexin, and a sufficient pool of UGGT is available to interact with mis-folded proteins that have lost their glucose tag. When ER calcium is depleted, each molecule of UGGT becomes stably complexed with a mis-folded protein, and thus unavailable to interact with the remaining mis-folded proteins in the ER. Since the mis-folded proteins are present in large molar excess over the UGGT, the excess mis-folded protein is free to escape the UGGT-mediated quality control system and to exit the ER. In contrast, in cells that do not express a mutant mis-folded protein, we hypothesize that UGGT exists in large molar excess over its potential substrates. Thus, when ER calcium is depleted, UGGT may act as a sink that can bind up newly synthesized proteins that have not completed their folding. Consequently, the bulk of newly synthesized proteins are retained in the ER.

H. Release of Mis-Folded ΔF508 CFTR Protein from the ER

We have developed a novel strategy that releases mis-folded ΔF508 CFTR protein from the ER and allows it to be functionally expressed at the cell surface. While not wishing to be bound by any theory, it is believed that retention of mis-folded membrane proteins in the ER is dependent upon interactions with ER resident chaperone proteins. Biochemical characterization of chaperone activity reveals that optimal functioning of several of these proteins requires calcium concentrations in the millimolar range (S. K. Nigam, A. L. Goldberg, S. Ho, M. F. Rohde, K. T. Bush, M. Y. Sherman, *J. Biol. Chem.* 269, 1744, 1994; S. E. Trombetta, A. J. Parodi, *J. Biol. Chem.* 267, 9236, 1992). Mobilization of sequestered ER $Ca^{2+}$ stores with agents such as the ER $Ca^{2+}$ pump inhibitor thapsigargin dramatically reduces the ER lumenal calcium concentration (M. Montero, J. Alvarez, W. J. J. Scheenen, R. Rizzuto, J. Meldolesi, T., Pozzan, *J. Cell Biol.* 139, 601, 1997). While not wishing to be bound by any theory, we postulate that exposing cells to thapsigargin might interfere with the capacity of chaperones to mediate the ER retention of mis-folded proteins and that depleting ER $Ca^{2+}$ stores with thapsigargin would allow the mis-folded ΔF508 CFTR protein to "escape" from the ER and potentially reach the cell surface, where it would be able to function as a chloride channel and correct the CF defect.

As described in the Examples, we have shown that treatment of CF airway epithelial cells with thapsigargin, which reduces the calcium concentration in the ER lumen, leads to functional expression of the ΔF508-CFTR protein at the cell surface as revealed by electrophysiologic and immunofluorescence analysis. In addition, we have shown that treatment with thapsigargin can induce reversal of a phenotypic defect in a mouse model for cystic fibrosis (CF mice). The dose of thapsigargin employed in these studies appears to be tolerable and induces an effect whose magnitude is probably sufficient to produce clinically significant improvements in airway epithelial function in cystic fibrosis patients.

Finally, it must be noted that the mechanism through which calcium pump inhibitors effect the release of ΔF508 CFTR from the ER may not be related directly to the calcium requirements of ER chaperone machinery. It is possible, for example, that depletion of calcium from the ER lumen is sufficient to facilitate the spontaneous folding of the ΔF508 CFTR protein, permitting it to acquire a stable conformation and bypass chaperone retention. In either case, it is clear that calcium pump inhibition is sufficient to release a cohort of ER-retained ΔF508 CFTR to the cell surface, where it can function appropriately (see Examples 1-8).

I. Rhinosinusitis and CFTR Mutations

Rhinosinusitis, or inflammation of the sinus epithelium, is an extremely common condition which can be divided into several subtypes including acute, recurrent acute, subacute, and chronic based typically on patient history and physical examination. The persistent form, chronic rhinosinusitis (CRS), affects approximately 14% of the U.S. population and is almost invariably present in patients with CF. A case-control study in which DNA of CRS patients (individuals with more than 8 weeks of nasal or sinus symptoms or with a history of at least 4 episodes of recurrent symptoms of greater than three weeks' duration in the prior 12 months) and controls was typed for 16 mutations that account for 85% of CF alleles in the general population and also tested for the presence of additional mutations and variants revealed that the proportion of CRS patients who were found to have a CF mutation in one of their copies of the CF gene (7%) was significantly higher than in the control group (2%) (Wang, X., et al. "Mutation in the Gene Responsible for Cystic Fibrosis and Predisposition to Chronic Rhinosinusitis in the General Population", *JAMA*, Vol. 284, No. 14, 2000). Approximately 90% of the patients with a CF mutation carried the ΔF508 allele. In addition, most of the CF carriers with CRS had variants in their other CFTR gene. In particular, the M470V variant was found in 9 of the 10 CRS patients with a CF mutation, and in 8 of these patients the M470V variant was in the gene that did not carry a CF-causing mutation. The variant with valine at amino acid position 470 has reduced chloride channel activity compared with that having methionine at position 470 although the reduction in activity is not generally sufficient to result in CF, the diagnosis of which is based in part on clinical criteria. Data from this study indicate that mutations in the CFTR gene may be associated with the development of CRS in the general population. The importance of CFTR in normal sinus epithelium function is evident from the fact that CRS occurs in almost all CF patients. Less severe decreases in CFTR activity, as may occur in individuals that are heterozygous for a CF mutation (particularly if they also have a variant CFTR allele at the other locus), may lead to CRS in the absence of CF. While not wishing to be bound by any theory, reduced CFTR activity may lead to abnormal viscosity and electrolyte composition of sinus secretions. Such abnormalities may increase the likelihood that rhinosinusitis will develop initially and/or that it will become chronic. These findings suggest that agents such as those described herein, which increase the functional activity of mutant CFTR, may be useful for prophylaxis and/or treatment of CRS.

It is noted that diagnosis of sinusitis is based at least in part on clinical criteria, and that various classification schemes may be applied (See, e.g., International Rhinosinusitis Advisory Board, "Infectious rhinosinusitis in adults: classification, etiology and management." *Ear, Nose, Throat J.* 76(12 suppl): 1-22). Determinations of whether a given patient suffers from a particular subtype may vary, and it is likely that certain individuals suffering from rhinosinusitis who carry a CF allele and/or CF variant will not be classified as having CRS but rather as having one of the other subtypes. Thus the agents described herein may also be useful for treatment or prophylaxis in individuals who suffer from rhinosinusitis that has not been classified as chronic rhinosinusitis. Such agents would be particularly appropriate for patients with rhinosinusitis who are CF carriers, patients who are CF carriers and have a CFTR variant at the second locus, and patients who are homozygous for a CFTR variant. As is well known in the art, patients who are CF carriers and/or have a CFTR variant may be identified by DNA analysis as described, for example, in Wang, X., et al. Thus the present invention provides a method for treating rhinosinusitis comprising administering an agent that permits the release of proteins from the endoplasmic reticulum. In certain embodiments of the invention the method further comprises providing an individual suffering from rhinosinusitis, e.g., from chronic rhinosinusitis. In certain embodiments of the invention such individual carries a CF mutation, e.g., ΔF508. In certain embodiments of the invention the individual carries a CF variant, e.g., M470V.

In certain embodiments of the invention the method comprises administering an agent that permits the release of proteins from the endoplasmic reticulum, an agent that decreases or inhibits the activity of UDP glucose:glycoprotein glycosyl transferase, an agent that decreases or inhibits activity of the endoplasmic reticulum $Ca^{++}$ ATPase, an agent that lowers the concentration of $Ca^{++}$ in the endoplasmic reticulum, an agent that causes release of $Ca^{++}$ from the ER, an agent that stimulates or increases $IP_3$ receptor activity, an agent that decreases or inhibits calnexin functional activity, or an agent that increases or activates ryanodine receptor activity. Particular agents that may be used in the practice of the invention include thapsigargin or a derivative thereof, cyclopiazonic acid or a derivative thereof, DBHQ or a derivative thereof and halothane or a derivative thereof.

In certain embodiments of the invention the agent is delivered intranasally according to methods well known in the art and widely used for treatment of allergies, etc. Of course the agent can be delivered by various other means as well.

Applications for Release of Normally Assembled or Folded Proteins from the ER

As described above, the present invention contemplates enhancing release of misassembled and/or misfolded proteins from the ER. According to certain embodiments of the invention release is enhanced by lowering the $Ca^{2+}$ concentration within the ER lumen. While not wishing to be bound by any theory, it is possible that lowering the ER $Ca^{2+}$ concentration may alter or interfere with the activity of chaperone proteins that would otherwise bind to a misassembled or misfolded protein and prevent its release from the ER.

The interaction of normal and mutant proteins with various ER chaperones is a subject of ongoing investigation. For example, in the case of CFTR it appears that the protein interacts with at least two ER chaperones, heat shock protein 90 (hsp90) and heat shock cognate 70 (hsc70) (refs). In a manner that is not yet fully understood and which depends at least in part on the primary sequence of the newly synthesized CFTR protein (e.g., whether it is wild type or mutant), these interactions ultimately lead to release of the protein from the ER, retention of the protein in the ER, and/or ubiquitination of the protein and ultimately ubiquitin-dependent degradation by the proteasome (refs). Only approximately 25% of the wild type CFTR protein attains a stable conformation (stable B) that allows it to exit the ER, while the remainder is ubiquitinated in the ER and thereby targeted for degradation. In the case of folding mutants an even smaller fraction of the protein reaches the stable B form. Very little if any ΔF508 CFTR protein reaches stable B, and thus essentially all the protein is ubiquitinated and degraded. While not wishing to be bound by any theory, it is possible that association with chaperones is involved both in proper folding of CFTR protein and in allowing ubiquitination of both normal and mutant CFTR. Thus it is possible that an agent that alters or interferes with chaperone activity may lead to decreased ubiquitination of wild type CFTR and thereby allow a greater amount of wild type CFTR to exit the ER. In the case of an individual who carries one wild type allele of the CFTR gene and one allele that encodes a misfolded CFTR protein, it is possible that treatment with such an agent would lead to increased cell surface expression of wild type CFTR, thus compensating for any decrease in cell surface expression resulting from the mutation.

It is therefore contemplated that the compositions and methods of the present invention may be useful not only to increase release of misassembled and/or misfolded proteins from the ER but also to increase release of wild type proteins from the ER, particularly in cases where a large fraction of the wild type protein is not released (as is the case for the normal CFTR protein). The compositions and methods may similarly be useful to increase release of mutant proteins from the ER even in cases in which the mutant proteins are not necessarily misassembled and/or misfolded.

Thus the compositions and methods of the invention may be used to treat individuals suffering from a condition associated with misassembly or misfolding of a protein, in whom one copy of a particular gene associated with the condition encodes a misassembled or misfolded protein while the other copy encodes a wild type protein or a mutant protein where the mutation does not result in misassembly or misfolding but instead results in a protein that functions at less than wild type levels for some other reason. As described above, such individuals may include individuals with rhinosinusitis, where the individuals have a mutation in at least one copy of the CFTR gene, regardless of whether the mutation results in synthesis of a misfolded protein. Such individuals also include individuals suffering from CF, where the individuals have different mutations in their two copies of the CFTR gene, only one of which results in production of a misfolded protein.

J. Applications for Non-CF Protein Release

In addition to CF, a large and growing list of disease states is associated with protein retention in the ER (Amara J, Cheng S and Smith A., *Trends in Cell Biol* 2:145-149 (1992); Bychkova V and Ptitsyn O, Folding intermediates are involved in genetic diseases?, *FEBS Lett* 359:6-8 (1995)), Several are listed and briefly discussed below.

α1-antitrypsin Deficiency. The α1-antitrypsin protein is synthesized in the liver and secreted into the circulation. It serves to prevent damage to the lungs induced by inflammatory processes. Absence of this protein leads to pulmonary scarring and emphysema. In the most common forms of human α1-antitrypsin deficiency, a mutation leads to the synthesis of an α1-antitrypsin molecule which can not fold properly and is consequently not secreted but rather is retained in the liver cell ER (Yu M, Lee K and Kim J, The Z type variation of human alpha 1-antitrypsin causes a protein folding defect, *Nature Structural Biology* 2:363-367 (1995)).

Paroxysmal Nocturnal Hemoglobinuria. In red blood cells, the inventory of glycosylphosphatidylinositol (GPI) linked proteins includes a pair of polypeptides, Decay Accelerating Factor (DAY) and CD59, which help to protect the erythrocytes from being accidentally injured by complement-mediated cell lysis. One of the proteins which participates in the synthesis of the GPI anchor is a sugar transferase encoded by the PIG-A gene (phospatidylinositol glycan-class A). This gene is located on the X chromosome. In Paroxysmal Nocturnal Hemoglobinuria, a spontaneous mutation occurs in the PIG-A gene in just one of the many precursor cells which give rise to erythrocytes. All of the erythrocytes which arise from this particular precursor, therefore, are deficient in GPI-linked protein synthesis. The transmembrane precursors of the GPI-linked proteins are retained in the ER and degraded. Consequently, these cells lack DAF and CD59 expression and are susceptible to complement attack and lysis. Patients with Paroxysmal Nocturnal Hemoglobinuria are likely to become anemic and can suffer life threatening disorders of clotting and bone marrow function. A treatment which liberated the transmembrane precursors of CPI-linked proteins from the ER and allowed them to travel to the cell surface might prevent or ameliorate the symptoms of this disease.

Familial Hypercholesterolemia. The disease known as Familial Hypercholesterolemia (FHC) is caused by a defect in the gene encoding the low density lipoprotein (LDL) receptor which results in the synthesis of receptors that can not internalize LDL from the cell surface (Goldstein et al., Receptor-Mediated Endocytosis: Concepts Emerging from the LDL Receptor System, *Ann. Rev. Cell Biol.* 1, 1-39 (1985)). In the absence of functional LDL receptors, cells are unable to import exogenous cholesterol. Even though serum cholesterol levels rise to extraordinarily high levels, cells are unaware of its presence since they lack the machinery that allows them to endocytose LDL. The excess cholesterol synthesis results in the build up of cholesterol-filled lipid droplets in cells throughout the body. Accumulation of these cholesterol inclusions in the smooth muscle cells that populate arterial walls produces atherosclerotic plaques, which can go on to occupy and occlude the lumens of the blood vessels themselves. A subset of the mutations in the gene encoding the LDL receptor which lead to FHC in humans (the class II mutations) lead to the synthesis of LDL receptors which can not fold properly and which are retained in the ER (Yamamoto et al., Deletion in cysteine-rich region of LDL receptor impedes transport to cell surface in WHHL rabbit, *Science* 232; 1230-1237, 1986). Consequently, they can not participate in the internalization of plasma LDL-bound cholesterol. Pharmacologic treatments which liberate these mis-folded LDL receptors from the ER and allowed them to proceed to the cell surface might allow them to function properly in cholesterol metabolism and prevent the formation of atherosclerotic plaques.

Tay-Sachs Disease. A number of human diseases have been traced to genetic deficiencies in specific lysosomal hydrolases (Griffiths et al., The Mannose-6-Phosphate Receptor and the Biogenesis of Lysosomes, *Cell* 52:329-341 (1988)). Children who suffer from Tay-Sachs disease, for example, carry a homozygous mutation in the gene encoding the lysosomal enzyme hexosaminidase A. Consequently, their lysosomes are unable to degrade substances containing certain specific sugar linkages. Since they can not be broken down, these substances accumulate in lysosomes. Over time they come to fill the lysosomes, which swell and crowd the cytoplasm. The resulting derangements of cellular function are toxic to a number of cell types and ultimately underlie this disease's uniform fatality within the first few years of life. At least one mutation which has been shown to induce Tay-Sachs disease leads to deletion of the last 22 amino acids of the protein, preventing its proper folding (Lau M M H and Neufeld E F, A frameshift mutation in a patient with Tay-Sachs disease causes premature termination and defective intracellular transport of the alpha-subunit of beta-hexosaminidase, *J Biol Chem* 264:21376-21380 (1989)). The mutant protein is retained in the ER and does not travel to its site of functional residence in the lysosome. Releasing this protein from the ER might prevent the Tay-Sachs pathology in patients who carry this allele.

Immune surveillance of tumors and virally infected cells. In order for the immune system to detect and destroy tumor cells and virally infected cells, these target cells must present peptide fragments derived from tumor or viral antigens at their cell surfaces in association with MHC class I molecules. These peptide fragments are derived from proteasome-mediated digestion of the foreign antigens followed by TAP-mediated transport of these fragments into the lumen of the ER, where they can assemble with MHC class I and β2-microglobulin to form the mature MHC complex. Only the mature, peptide-containing MHC complex can depart the ER and be transported to the cell surface. In the absence of peptides in the lumen of the ER, the incompletely assembled MHC I-β2-microglobulin complex is retained in the ER through interactions with calnexin.

Several viruses and tumors avoid immune detection by blocking the surface expression of the mature MHC class I complex. The herpes simplex virus induces host cells to synthesize the ICP47 protein, which directly inhibits the TAP transporter (Hughes E, Hammond C and Cresswell P, Misfolded major histocompatibility complex class I heavy chains are translocated into the cytoplasm and degraded by the proteasome, *PNAS* 94:1896-1901 (1997)). In a number of tumors, expression of the genes encoding the two polypeptides which constitute the TAP transporter is lost (Pogador et al., Natural killer cell lines kill autologous β2-microglobulin-deficient melanoma cells: Implications for cancer immunotherapy, *PNAS* 94:13140-13145 (1997)). Consequently, the immune system is unable to respond adequately to the pathologic condition. To assist the immune system in recognizing and destroying virally infected or transformed cells, it might be desirable to release the peptide-free MHC class I-β2-microglobulin complex from calnexin-mediated ER retention. This complex would then travel to the cell surface, where it could associate with a specific peptide, administered to the patient by infusion and chosen to maximize the immunogenicity of the resulting peptide-MHC-class I-β2-microglobulin complex. Thus, drugs which release mis-assembled proteins from the ER might prove efficacious in the treatment of a variety of viral and neoplastic diseases.

Hereditary Myeloperoxidase Deficiency. Phagocytes, in particular neutrophils, respond to stimulation with a burst of oxygen consumption. The oxygen consumed is converted to hydrogen peroxide by myeloperoxidase (MPO), which is released from the neutrophil granules, and a complex is formed that is capable of oxidizing a large variety of substances, and that has, as a result, important anti-microbial properties (Klebanoff, Myeloperoxidase, *Proc. Assoc. Am. Physicians*, 111(5):383-389, 1999).

In the endoplasmic reticulum, MPO precursors interact transiently with calrecticulin and calnexin, presumably as molecular chaperones. MPO deficiency is a relatively common disorder, and several missense mutations have been identified where the mutant precursor is retained in the endoplasmic reticulum due to prolonged binding to calnexin. The mis-folded protein is eventually degraded (Nauseef, *Quality Control in the Endoplasmic Reticulum: Lessons from Hereditary Myeloperoxidase Deficiency*, J. Lab. Clin. Med., 134(3): 215-221 (1999)). Here as well, a treatment that would allow the protein to exit the FR might restore anti-bacterial phagocytic function to individuals suffering from MPO deficiency.

Congenital Insulin Resistance. The hormone binding site of the insulin receptor is contained in the extracellular region of the protein. In this form of type A insulin resistance, substitution mutations of residues located in the beta-sheet and at the hormone-binding region completely disrupt intracellular folding and movement of the protein, resulting in aberrant retention at an incorrect cellular location.

Misfolded receptors remain bound to calnexin molecules in the endoplasmic reticulum until they are degraded. As previously discussed in connection with other diseases, a treatment providing release and cellular export of the mutant receptor could have wide-spread therapeutic use.

Nephrogenic Diabetes Insipidus. Nephrogenic diabetes insipidus is characterized by an inability to concentrate urine in spite of normal or increased plasma concentrations of the antidiuretic hormone arginine vasopression (AVP), which normally stimulates water reabsorbtion in the distal tubules and/or collecting ducts of the kidney by regulating the expression of "water channels" known as aquaporins. In the collecting duct, binding of AVP to the vasopressin 2-receptor triggers a cascade—activation of the receptor-linked G protein $G_s$, activation of adenylate cyclase, and stimulation of protein kinase A, eventually leading to exocytic insertion of specific water channels, aquaporin 2, into the luminal membrane of collecting duct cells. Presence of these channels increases permeability of the luminal membrane. Thus short term regulation of AQP2 by AVP entails movement of AQP2 from intracellular vesicles to the plasma membrane. Longer term regulation occurs through increased abundance of APQ2, which is thought to result from increased transcription of the AQP2gene. AVP also increases renal water reabsorption through a variety of additional mechanisms. Nephrogenic diabetes insipidus is comprehensively reviewed in Morello, J. and Bichet, D., Nephrogenic diabetes insipidus, *Annu. Rev. Physiol.*, 63:607-30, 2001.

Nephrogenic diabetes insipidus can be inherited or acquired Polyuria and polydipsia are the major symptoms. Approximately 90% of patients with congenital nephrogenic diabetes insipidus have an X-linked form of the disorder caused by mutations in the arginine vasopressin receptor 2 gene (AVPR2). In less than 10% of families studied the disorder has an autosomal recessive or autosomal dominant pattern of inheritance. Mutations in the aquaporin-2 gene (AQP2) have been identified in some of these kindreds. Based on studies of glycosylation patterns, it is apparent that most AVPR2 mutations lead to receptors that are trapped in a pre-Golgi compartment, presumably the ER, and are thus unable to reach the cell surface (See Morello and Bicbet, 2001 and papers referenced therein). AQP-2 mutations that cause autosomal recessive nephrogenic diabetes insipidus are also characterized by misfolded mutant proteins that are trapped in the ER (Kamsteeg, E. J., et al., An impaired routing of wild-type aquaporin-2 after tetramerization with an aquaporin-2 mutant explains dominant nephrogenic diabetes insipidus; reviewed in van Os, C. H. and Deen, P. M., Aquaporin-2 water channel mutations causing nephrogenic diabetes insipidus, *Proc. Assoc. Am. Physicians*, 110(5): 395-400, 1998). Thus agents and methods such as those described herein, that allow release of misfolded proteins from the ER, are likely to be useful in the treatment of congenital nephrogenic diabetes.

Hereditary Hemochromatosis. Hemochromatosis is a common autosomal recessive disorder characterized by excessive accumulation of iron in many organs and tissues including the liver, pancreas, heart, joints, and endocrine organs due to increased absorption of iron in the gastrointestinal tract. Clinical consequences includes cirrhosis of the liver, hepatocellular carcinoma, diabetes, heart failure, arthritis, and hypogonadism. A large number of studies have indicated that hereditary hemochromatosis (HH) is caused by mutations in a gene that encodes a novel member of the major histocompatibility complex class I family initially called HLA-H but now designated as HFE (See, e.g., Feder, J. N., et al., *Nature Genetics*, 13: 339-408, 1996; Beutler, E., et al., *Blood Cells Mol. Dis.*, 22: 187-194, 1996). Most patients with HH are homozygous for the same missense mutation (C282Y in the gene that encodes HFE. A recent study demonstrated that the C282Y mutant protein is retained in the ER and middle Golgi compartment and is subject to accelerated degradation (Waheed, A., et al., Hereditary hemochromatosis: Effects of C282Y and H63D mutations on association with β2-microglobulin, intracellular processing, and cell surface expression of the HFE protein in COS-7 cells, *Proc. Natl. Acad. Sci.*, 94; 12384-12389, 1997). Much of the newly synthesized C282Y mutant HFE protein occurs in a high molecular weight aggregate as is characteristic of misfolded proteins that are retained in the ER or Golgi. The C282Y mutation reduces or prevents association of PIE with β2-microglobulin, which is necessary for normal intracellular transport of HFE and delivery to the cell surface. Thus agents, such as those described herein, that increase or stimulate the release of misfolded proteins from the ER may be useful in the prevention or treatment of HH by allowing mutant HFE to exit the ER and reach the cell surface.

Gitelman's Syndrome. Gitelman's syndrome is an autosomal recessive disorder characterized by salt wasting and hypokalemia and is caused by mutations in the thiazide sensitive Na—Cl cotransporter (NCC), which is normally expressed in the mammalian kidney at the apical membrane of distal convoluted tubule cells (See, e.g., Simon, D. B., et al., Gitelman's variant of Bartter's syndrome, inherited hypokalemic alkalosis, is caused by mutations in the thiazide-sensitive Na—Cl cotransporter, *Nat. Genet*, 12: 24-30, 1996). In a recent study designed to elucidate the pathogenesis of Gitelman's syndrome, eight mutations corresponding to eight disease-causing mutations found in Gitelman's syndrome patients were introduced into the mouse NCC and studied by functional expression in *Xenopus oocytes* (Kunchaparty, S., et al., Defective processing and expression of thiazide-sensitive Na—Cl cotransporter as a cause of Gitelman's syndrome, *Am J Physiol.*, October, 277 (4 Pt 2):F643-9, 1999). Results indicated that a number of the mutations interfere with proper processing and insertion into the plasma membrane. The nearly complete absence of glycosylation argues that the mutant proteins do not exit the ER. The results suggest that at least a subset of Gitelman's mutations, including the most common mutation (G738R), lead to production of proteins that are not glycosylated normally because of misfolding during synthesis. Thus agents, such as those described herein, that increase or stimulate the release of misfolded proteins from the ER may be useful in the prevention or treatment of Gitelman's syndrome by allowing mutant NCC to exit the ER and reach the cell surface.

Cystinuria. Cystinuria is a common inherited disorder characterized by defective transport of cystine and dibasic amino acids through the epithelial cells of the renal tubule and gastrointestinal tract, commonly resulting in the development of cystine calculi (stones) in the kidney. Three types of cystinuria have been described. Mutations in SLC3A1, a gene encoding a subunit of the rBAT protein (an amino acid transporter), have been shown to cause Type I cystinuria. In a recent study designed to investigate the pathogenesis of Type I cystinuria, the most common point mutation, M467T and the related mutation M467K were introduced into rBAT and studied by functional expression in *Xenopus oocytes* (Chillarón, J., et al., An Intracellular Trafficking Defect in Type I rBAT Mutants M476T and M467K, *J. Biol Chem.*, 272(14), 9543-9549, 1997). The study indicated that the mutations interfered with proper intracellular processing and transport to the plasma membrane. Unlike wild type rBAT, the mutant proteins were primarily located in an intracellular compartment, most likely the ER. Evidence also suggested that, if able to reach the cell surface, as is the case if the experimental system is saturated with cDNA encoding the mutant, the mutant proteins are functional. As for the other mutant proteins described herein, it is likely that mutations in rBAT lead to misfolding and retention in the ER. Thus agents, such as those described herein, that increase or stimulate the release of misfolded proteins from the ER may be useful in the prevention or treatment of Type I cystinuria (and possibly other forms of cystinuria that may involve rBAT) by allowing mutant rBAT to exit the ER and reach the cell surface.

With respect to the disorders and conditions discussed above, in certain embodiments of the invention the method for treatment and/or prevention or prophylaxis comprises administering an agent that permits the release of proteins from the endoplasmic reticulum, an agent that decreases or inhibits the activity of UDP glucose:glycoprotein glycosyl transferase, an agent that decreases or inhibits activity of the endoplasmic reticulum $Ca^{++}$ ATPase, an agent that lowers the concentration of $Ca^{++}$ in the endoplasmic reticulum, an agent that causes release of Ca++ from the ER, an agent that decreases or inhibits $IP_3$ receptor activity, an agent that decreases or inhibits calnexin functional activity, or an agent that increases or activates ryanodine receptor activity. Particular agents that may be used in the practice of the invention include thapsigargin or a derivative thereof, cyclopiazonic acid or a derivative thereof, DBHQ or a derivative thereof, and halothane or a derivative thereof.

K. Thapsisargin

General Description. Thapsigargin and related sesquiterpene lactones are naturally-occurring compounds known to selectively inhibit all of the SERCA ATPases, a family of $Ca^{+2}$-pumping ATPases present in the ER of all mammalian cells, with subnanomolar potency. These inhibitors have no effect on the $Ca^{+2}$-ATPase of the plasma membrane or on other P-type ATPases. Members of this class of inhibitors include thapsigargin and thapsigargicin, both isolated from *Thapsia garganica*, thapsivillosin A (TvA), isolated from *Thapsia villosa*, and trilobolide, extracted from *Laser trilobum* (Wictome et al., *Biochem. J.* 310:859-868 (1995)).

Functional Role. Thapsigargin appears to induce a conformational state of the pump in which several of the partial reactions (e.g., $Ca^{+2}$ binding, $Ca^{+2}$-independent phosphorylation by P, nucleotide binding) are blocked (Inesi et al., *Arch. Biochem. Biophys.* 298:313-317 (1992)). Studies utilizing a series of thapsigargin analogues indicated that the compound fits into a sterically discriminating cleft involving the hydrophobic transmembrane region of the ATPases (Christensen et al., *Federation of European Biochemical Societies* 335(3): 345-348 (1993)).

Clark et al (*J. Orthop. Res.* 12(5):601-611 (1994)) reported that "the calcium-mobilizing agents thapsigargin and 2,5-di-(tert-butyl)-1,4-benzohydroquinone were shown to markedly elevate the intracellular calcium concentration of chick embryo chondrocytes in a dose-dependent manner." The observed effects of the two compounds on secretion of chondrocyte proteins, including collagen and proteoglycan, was speculated as being due to the specific depletion of the calcium sequestered in the ER.

Addition of 2 mmol/liter $Ca^{+2}$ to thapsigargin-treated CFPAC-1 cells produced a sustained increase of $Cl^-$ and $K^+$ currents, which was reversed by $Ca^{+2}$ removal (Galietta et al., *Pflugers Arch.* 426(6):534-541 (1994)). The researchers concluded "that CFPAC-1 cells respond to nucleotide receptor activation with a transient increase in intracellular $Ca^{+2}$ concentration that stimulates $Ca^{+2}$-dependent $Cl^-$ and $K^+$ currents."

It should be noted that it would not be obvious that long term exposure to thapsigargin will increase functional expression of CFTR. For example, down-regulation of CFTR gene expression was observed by others after exposure of HT-29 human colon carcinoma cells to; (1) agents which increase intracellular divalent cation concentrations (e.g., agents such as the divalent cation ionophores A23187 and ionomycin); (2) thapsigargin; and, (3) growth media containing increased extracellular concentrations of $Ca^{+2}$ or $Mg^{+2}$ (argon et al., *Mol. Cell. Biol.* 192(4):1872-1878 (1992)). These researchers stated that thapsigargin was "an agent that releases $Ca^{+2}$ from intracellular stores" resulting in a higher intracellular level of divalent cation concentration. The authors concluded that "despite the independence of $Ca^{+2}$-dependent $Cl^-$ channels and cyclic AMP-dependent CFTR-related $Cl^-$ channels in epithelial cells, increases in intracellular divalent cation concentrations down-regulate the expression of the CFTR gene at the transcriptional level, with consequent decreases in CFTR mRNA and protein."

Exposure of tumor sections from BALB/Urd mice to ionomycin or thapsigargin resulted in a concomitant efflux of $^{125}I$, $^{36}Cl$ and $^{86}Rb$ (Basavappa et al., *Gastroenterology* 104(6): 1796-1805 (1993)).

L. Curcumin

General Description. Curcumin (diferuoylmethane or 1,7-bis(4-hydroxy-e-methoxyphenol)-1,6-heptadiene-3,5-dione) is a naturally occurring compound found in the Asian spice turmeric and is responsible for its characteristic yellow color. Curcumin has been shown to have anticancer activity, perhaps as a consequence of its antioxidant and/or anti-angiogenic properties (Kelloff, G., et al., *J. Cell. Biochem.,* 26:1-28, 1996; Xu, Y., et al., *Exp. Hematol.,* 25:413-422, 1997). Studies suggest that curcumin and/or certain curcumin derivatives can affect a variety of cellular processes including: activation of apoptosis (Piwocka, K., et al., *Exp. Cell Res.,* 249: 299-307, 1999), inhibition of platelet aggregation (Shah, B., et al., *Biochem. Pharmacol.,* 58: 1167-1172, 1999), and inhibition of cytokine production (Abe, Y., et al., *Pharmacol. Res.,* 39: 41-47, 1999). It has been shown that curcumin can affect the activity of a number of cellular enzymes including cyclooxygenase (Zhang, F., et al., *Carcinogenesis,* 20: 445-451, 1999), protein kinase C (Liu, J., et al., *Carcinogenesis,* 14, 857-861, 1998), protein tyrosine kinases (Chen, H., et al., *J. Pharmacol.,* 124: 1029-1040, 1998), phosphorylase kinase (WO0070949), NFκB (U.S. Pat. No. 5,891,924), and an endonuclease (Chen, Y., et al., *Mol. Carcinog.,* 17: 224-234). Curcumin is thought to possess anti-inflammatory properties, possibly as a result of NFκB and/or cyclooxygenase inhibition.

Functional Activity. Curcumin and related 1,7-diaryl-1,6-heptadiene-3,5-diones are known to inhibit members of the SERCA family of $Ca^{2+}$-pumping ATPases, which are present in the ER of all mammalian cells, with micromolar potency (Bilmen, J., et al., *Eur. J. Biochem.* 268: 6318-6327, 2001; Logan-Smith, M., et al, *J. Biol. Chem.* 276(50): 46905-46911, 2001). These inhibitors appear to have little or no effect on the $Ca^{+2}$-ATPase of the plasma membrane or on other P-type ATPases.

While not wishing to be bound by any theory, it appears that curcumin induces a conformational state of the SERCA pump in which ATP is prevented from binding, thus inhibiting overall ATPase activity and Ca(2+) transport by interfering with phosphoenzyme formation with ATP or P(i). These effects may be particularly evident at higher curcumin concentrations (e.g., 5-30 μM or greater). While not wishing to be bound by any theory, inventors suggest that inhibition of SERCA results in a lower concentration of $Ca^{2+}$ within the ER. Reduction in $Ca^{2+}$ concentration may reduce the activity of $Ca^{2+}$-dependent chaperones, thereby allowing the release of misfolded or misassembled proteins such as mutant CFTR that would otherwise be retained within the ER.

Production of Curcumin and Curcumin Derivatives. Curcumin and certain homologs (demethoxy curcumin, and bis demethoxy curcumin) can be isolated from plants such as *Curcuma longa* (See, e.g., U.S. Pat. No. 5,861,415). However, such processes are relatively time-consuming and typically result in isolation of a mixture of curcumin related compounds. For purposes of the present invention the term "curcumin related compound" includes 1,7-diaryl-1,6-heptadiene-3,5-iones. According to certain embodiments of the invention the term includes homologs and analogs of such compounds. A variety of methods for synthesis of curcumin and a wide range of related compounds and derivatives are known in the art. For example, U.S. Pat. No. 5,679,864 discloses a process for the synthesis of curcumin and curcumin-related compounds including demethoxycurcumin and ethyl curcumin by reacting the enol form of a 2,4-diketone with a monocarbocyclic aldehyde in the presence of an organic amine catalyst. US publication 20020019382 and WO0140188 disclose synthesis and biological activity of a group of curcumin analogs. Anto, R, et al., *Mutat. Res.* 370 (2):127-31, 1998 discloses biological activity of various synthetic cutcuminoids. WO0070949 discloses structures of a wide variety of curcuminoids and curcumin derivatives including compounds designated as furfural curcuminoids, salicyl curcuminoids, veratryl curcuminoids, p-anisyl curcuminoids, piperonal curcuminoids, tetrahydrocurcuminoids, etc. Each of the foregoing constitutes a family of curcumin analogs, wherein the family members may contain various different substituents.

Thus the present invention contemplates the use of both the naturally occurring curcuminoids, curcumin I (diferuloylmethane), curcumin II (feruloyl-p-hydroxycinnamoyl-methane) and curcumin III (bis-(p-hydroxycinnamoyl)methane) and also curcumin related compounds and derivatives for the treatment of cystic fibrosis. As described above, inventors hypothesize that curcumin's ability to inhibit SERCA may be important in terms of its ability to cause release of misfolded proteins from the ER. Therefore, preferred curcumin related compounds, analogs, or derivatives for use in certain embodiments of the invention are compounds that inhibit SERCA. The ability of any particular compound to inhibit SERCA can readily be tested using methods known in the art, such as those described in Blimen, et al, referenced above. For example, $Ca^{2+}$ ATPase activity can be measured using purified protein, membranes, membrane vesicles, microsomes, etc. $Ca^{2+}$ uptake can be conveniently measured in microsomes. In performing such measurements it is important to test a range of concentrations of the candidate compound since at low concentrations (e.g., below approximately 0.8 uM) curcumin has been shown to cause an increase in SERCA activity in certain experimental settings (Logan-Smith, et al., referenced above). According to certain embodiments of the invention preferred curcumin related compounds include those having an —OH group at the 4-position of the phenyl rings.

The efficacy of any particular curcumin related compound, curcumin analog or derivative, etc., for treatment of cystic fibrosis may readily be tested using the assays described herein, e.g., ability of the compound to cause translocation of mutant CFTR to the plasma membrane of cells expressing mutant CFTR, ability of the compound to restore a phenotypic characteristic such as the nasal potential difference of a CF knockout mouse to a more normal value, etc. Similar assays may be employed to identify particular curcumin related compounds, derivatives, or analogs for use in treatment of other diseases characterized by retention of misfolded or misassembled proteins within the ER and/or failure of such proteins to reach their normal subcellular location. In performing such assays it is important to test a range of concentrations of the candidate compound. In addition to the use of in vitro studies and studies in animal models, the efficacy of curcumin or any particular curcumin related compound, curcumin analog or derivative, etc., can be tested in individuals suffering from the condition to be treated. The level or severity of any symptom or manifestation of the condition in individuals who have been treated can be compared with the severity of such symptom or manifestation in untreated individuals or in individuals treated with a different agent. In individuals suffering from cystic fibrosis, for example, nasal potential difference, mucociliary clearance, sweat chloride levels, or sputum cohesiveness may be evaluated in human subjects. (See, e.g., Robinson, M. et al., Pediatric Pulmonology. 30(1):16-24, 2001; Robinson, M., et al, American Journal of Respiratory & Critical Care Medicine. 153(5):1503-9; Robinson, M., et al, Pediatric Pulmonology. 32(2):122-8, 2001; Rubenstein, R. and Zeitlin, P, American Journal of Respiratory & Critical Care Medicine. 157(2):484-90, 1998; American Journal of Respiratory & Critical Care Medicine. 157(3 Pt 1):710-4, 1998; McCarty, N., et al., Pediatr Pulmonol. 2002 February; 33(2):90-8 for descriptions of such studies). Of course any of a variety of other clinical endpoints may be used as appropriate to the particular condition.

M. Recombinant DNA

In accordance with the present invention, as described above or as discussed in the Examples below, there may be employed conventional molecular biology, microbiology and recombinant DNA techniques. Such techniques are explained fully in the literature. See for example, Sambrook et al., *Molecular Cloning: A Laboratory Manual* (Second Ed., Cold Spring Harbor Press, Cold Spring Harbor N.Y., 1989); *DNA Cloning: A Practical Approach*, vol. 1 and 2 (D. N. Glover ed., 1985), *Oligonucleotide Synthesis* (M. J. Gait ed., 1984); *Nucleic Acid Hybridization* (B. D. Hames et al., 1985); *Transcription and Translation* (B. D. Hames et al., eds, 1984); E. Harlow et al., *Antibodies: A Laboratory Manual* (Cold Spring Harbor Press, Cold Spring Harbor N.Y., 1988); Roe et al., *DNA Isolation and Sequencing: Essential Techniques* (John Wiley & Sons, NY, 1996) and Ausubel et. al., *Current Protocols in Molecular Biology* (Greene Publishing Co. NY, 1995) to name a few.

For recombinant procedures related to treating cystic fibrosis see, for example, U.S. Pat. Nos. 5,602,110, 5,674,898 and 5,707,855.

N. Antisense and Short Interfering RNA

Antisense molecules are RNA or single-stranded DNA molecules with nucleotide sequences complementary to a specified mRNA. When a laboratory-prepared antisense molecule is injected into cells containing the normal mRNA transcribed by a gene under study, the antisense molecule can base-pair with the mRNA, preventing translation of the mRNA into protein. The resulting double-stranded RNA or RNA/DNA is digested by enzymes that specifically attach to such molecules. Therefore, a depletion of the mRNA occurs, blocking the translation of the gene product so that antisense molecules find uses in medicine to block the production of deleterious proteins. Methods of producing and utilizing antisense RNA are well known to those of ordinary skill in the art (see, for example, C. Lichtenstein and W. Nellen (Editors), *Antisense Technology: A Practical Approach*, Oxford University Press (December, 1997); S. Agrawal and S. T. Crooke, *Antisense Research and Application* (Handbook of Experimental Pharmacology, Volume 131), Springer Verlag (April, 1998); I. Gibson, *Antisense and Ribozyme Methodology: Laboratory Companion*, Chapman & Hall (June, 1997); J. N. M. Mol and A. R. Van Der Krol, *Antisense Nucleic Acids and Proteins*, Marcel Dekker; B. Weiss, *Antisense Oligonodeoxynucleotides and Antisense RNA Novel Pharmacological and Therapeutic Agents*, CRC Press (June, 1997); Stanley et al., *Antisense Research and Applications*, CRC Press (June, 1993); C. A. Stein and A. M. Krieg, *Applied Antisense Oligonucleotide Technology* (April, 1998)).

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding UGGT. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept can be extended by the inclusion of nontraditional bases such as inosine, queosine, and wybutosine, as well as acetyl-, methyl-, thio-, similarly modified forms of adenine, cytidine, guanine, thymine, and uridine which are not as easily recognized by endogenous endonucleases.

RNA interference (RNAi) is a mechanism of post-transcriptional gene silencing mediated by double-stranded RNA (dsRNA), which is distinct from the antisense and ribozyme-based approaches described above. dsRNA molecules are believed to direct sequence-specific degradation of mRNA in cells of various yes after first undergoing processing by an RNase III-like enzyme called DICER (Bernstein et al., Nature 409:363, 2001) into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

siRNA has been shown to downregulate gene expression when transferred into mammalian cells by such methods as transfection, electroporation, or microinjection, or when expressed in cells via any of a variety of plasmid-based approaches. RNA interference using siRNA is reviewed in, e.g., Tuschl, T., *Nat. Biotechnol.*, 20:446-448, May 2002. See also Yu, J., et al., *Proc. Natl. Acad. Sci.*, 99(9), 6047-6052 (2002); Sui, G., et al., *Proc. Nail. Acad. Sci.*, 99(8), 5515-5520 (2002); Paddison, P., et al., *Genes and Dev.*, 16, 948-958 (2002); Brummelkamp, T. et al., *Science*, 296, 550-553 (2002); Miyagashi, M. and Taira, K., *Nat. Biotech.*, 20, 497-500 (2002); Paul, C., et al., *Nat. Biotech.*, 20, 505-508 (2002). As described in these and other references, the siRNA may consist of two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is thought that intracellular processing (e.g., by DICER) of a variety of different precursors results in production of siRNA capable of effectively mediating gene silencing. Generally it is preferred to target exons rather than introns, and it may also be preferable to select sequences complementary to regions within the 3' portion of the target transcript. Generally it is preferred to select sequences that contain approximately equimolar ratio of the different nucleotides and to avoid stretches in which a single residue is repeated multiple times.

siRNAi may thus comprise RNA molecules having a double-stranded region approximately 19 nucleotides in length with 1-2 nucleotide 3' overhangs on each strand, resulting in a total length of between approximately 21 and 23 nucleotides. As used herein, siRNA also includes various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain embodiments of the invention the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may but need not comprise a plurality of U residues, e.g., between 1 and 5 U residues.

Accordingly, the invention provides siRNA compositions targeted to UDP glucose:glycoprotein glycosyl transferase, calnexin, endoplasmic reticulum $Ca^{++}$ ATPase, or any chaperone involved in retention of a misfolded or misassembled protein in the ER, which retention is associated with a disease or clinical condition. The siRNAs of the invention may be prepared by any method known in the art for the synthesis of nucleic acid molecules. These include techniques for chemical synthesis such as solid phase phosphoramidite chemical synthesis. Inventive siRNAs may be comprised entirely of natural RNA nucleotides, or may instead include one or more nucleotide analogs and/or modifications as mentioned above for antisense molecules. The siRNA structure may be stabilized, for example by including nucleotide analogs at one or more free strand ends in order to reduce digestion, e.g., by exonucleases. This may also be accomplished by the inclusion. Alternatively, siRNA molecules may be generated by in vitro transcription of DNA sequences encoding the relevant molecule. Such DNA sequences may be incorporated into a wide variety of vectors with suitable RNA polymerase promoters such as T7, T3, or SP6.

siRNA may be generated by intracellular transcription of small RNA molecules, which may be followed by intracellular processing events. For example, intracellular transcription is achieved by cloning siRNA templates into RNA polymerase III transcription units, e.g., under control of a U6 or H1 promoter. In one approach, sense and antisense strands are transcribed from individual promoters, which may be on the same construct. The promoters may be in opposite orientation so that they drive transcription from a single template, or they may direct synthesis from different templates. In a second approach siRNAs are expressed as stem-loop structures. The siRNAs of the invention may be introduced into cells by any of a variety of methods. For instance, siRNAs or vectors encoding them can be introduced into cells via conventional transformation or transfection techniques. As used herein, the terms "transformation" and "transfection" are intended to refer to a variety of aft-recognized techniques for introducing foreign nucleic acid (e.g., DNA or RNA) into a host cell, including calcium phosphate or calcium chloride co-precipitation, DEAE-dextran-mediated transfection, lipofection, injection, or electroporation.

Vectors that direct in vivo synthesis of siRNA constitutively or inducibly can be introduced into cell lines, cells, or tissues. In certain preferred embodiments of the invention, inventive vectors are gene therapy vectors (e.g., adenoviral vectors, adeno-associated viral vectors, retroviral or lentiviral vectors, or various nonviral gene therapy vectors) appropriate for the delivery of an siRNA-expressing construct to mammalian cells, most preferably human cells. Thus the present invention includes gene therapy approaches to the treatment of diseases or clinical conditions associated with retention of misassembled or misfolded proteins in the ER.

The invention includes methods of treating a disease or clinical condition associated with retention of misfolded or misassembled proteins in the ER comprising administering siRNA compositions comprising siRNA that targets UDP glucose:glycoprotein glycosyl transferase, calnexin, endoplasmic reticulum $Ca^{++}$ ATPase, or a chaperone involved in retention of a misfolded or misassembled protein in the ER, which retention is associated with the disease or clinical condition, to a subject in need of treatment for the disease or clinical condition. In certain embodiments of the invention the condition is CF and the protein is mutant CFTR. The compositions may be administered parenterally, orally, inhalationally, etc. The invention also includes methods of treating a disease or clinical condition associated with retention of a misfolded or misassembled protein in the ER comprising administering vectors or constructs capable of directing transcription of siRNA that targets UDP glucose:glycoprotein glycosyl transferase, calnexin, endoplasmic reticulum $Ca^{++}$ ATPase, or a chaperone involved in retention of a misfolded or misassembled protein in the ER, which retention is associated with the disease or clinical condition, to a subject in need of such treatment. According to certain embodiments of the invention the condition is CF, and the protein is mutant CFTR.

Preferred siRNA compositions reduce the level of the target transcript and its encoded protein by at least 2-fold, preferably at least 4-fold, more preferably at least 10-fold or more. The ability of a candidate siRNA to reduce expression of the target transcript and/or its encoded protein may readily be tested using methods well known in the art including, but not limited to, Northern blots, RT-PCR, microarray analysis in the case of the transcript, and various immunological methods such as Western blot, ELISA, immunofluorescence, etc., in the case of the encoded protein. In addition, the potential of any siRNA composition for treatment of a particular condition or disease associated with retention of a misfolded or misassembled protein in the ER may be assessed by examining the ability of the siRNA composition to enhance transport of the misassembled or misfolded protein to its correct cellular location. Efficacy may also be tested in appropriate animal models or in human subjects.

The foregoing methods are applicable generally to a wide range of diseases or clinical conditions associated with retention of misfolded or misassembled proteins in the ER including, but not limited to, chronic obstructive pulmonary disease, paroxysmal nocturnal hemoglobinuria, familial hypercholesterolemia, Tay-Sachs disease, viral diseases, neoplastic diseases, hereditary myeloperoxidase deficiency, congenital insulin resistance, nephrogenic diabetes insipidus, rhinosinusitis, hemochromatosis, Gitelman's Syndrome, and cystinuria.

O. High-Throughput Screening

The power of high throughput screening is utilized in the search for new compounds (in addition to thapsigargin, curcumin, etc.) which are capable of mobilizing mis-folded or incompletely assembled proteins from the ER, thus enabling their surface delivery. The following protocol is designed to permit rapid automated screening of large numbers of compounds useful for practicing the claimed invention. The demonstration that thapsigargin and/or curcumin produces a positive result when tested in the high-throughput screening assays will act as a positive control. For general information on high-throughput screening, see, for example, *Cost-Effective Strategies for Automated and Accelerated High-Throughput Screening*, IBCS Biomedical Library Series, IBC United States Conferences (February, 1996); John P. Devlin (Editor), *High Throughput Screening*, Marcel Kedder(1998); U.S. Pat. No. 5,763,263;

CTL-Mediated Cell Lysis. Cytotoxic T cells recognize their targets through interactions with Major Histocompatibility Complex (MHC) class I proteins expressed on the target cell surfaces. MHC class I is a complex composed of the MHC class I heavy chain (a transmembrane protein) and 2-microglobulin ($\beta$2m). MHC class I heavy chains assemble with $\beta$2m during their post-synthetic residence in the ER. Each MHC class I heavy chain also binds to a peptide produced by cytosolic proteolysis catalyzed by the proteasome and transported into the lumen of the ER by the ATP-dependent transporter associated with antigen processing (TAP). The complete MHC class I heavy chain-$\beta$2m-peptide complex must be fully assembled before it can depart the ER and be delivered to the cell surface. In the absence of $\beta$2m or of peptide, MHC class I is retained in the ER and is unavailable for recognition by T cells.

For general information on the Major Histocompatibility Complex, see, for example, Srivastava et al., *Immunogenetics of the Major Histocompatibility Complex*, Vch Pub. (March, 1991); B. Pernis and H. J. Vogel, *Cell Biology of the Major Histocompatibility Complex*, Academic Press (October, 1995); T. W. Mak and J. Simard, *Handbook of Immune Response Genes*, Plenum Pub. Corp. (February, 1998); R. E. Humphreys and S. K. Pierce, *Antigen Processing and Presentation*, Academic Press (August, 1994); J. Klein and D. Klein, *Molecular Evolution of the Major Histocompatibility Complex*, NATO Asi Series, Series H, Cell Biology, Vol. 59, Springer Verlag (January, 1992); L. B. Schook and S. J. Lamont, *The Major Histocompatibility Complex Region of Domestic Animal Species*, CRC Series in Comparative Immunology, CRC Press (September, 1996); U.S. Pat. Nos. 5,364,762, 5,639,458 and 5,734,023.

The 0.174 line of lymphoblastoid cells (hereinafter, 'the 0.174 cells') carries a mutation that eliminates the function of the TAP transporter (DeMars et al., Mutations that impair a posttranscriptional step in expression of HLA-A and -B antigens, *PNAS* 82:8183-8187 (1985); Hughes A, Hammond C and Cresswell P, Mis-folded major histocompatibility complex class I heavy chains are translocated into the cytoplasm and degraded by the proteasome, *PNAS* 94:1896-1901 (1997)). Consequently, proteasome-processed peptides are not available for assembly with MHC class I molecules in these cells. As a result, most MHC class I molecules (with the exception of those which can assemble with signal sequence peptides) are retained in the ER.

An assay based on cytotoxic T lymphocyte (CTL)-mediated cell lysis is used to identify compounds which permit MHC class I molecules to be released from the ER and expressed at the surface of 0.174 cells. A line of 0.174 cells expressing a specific MHC class I allele will be prepared by standard cDNA transfection techniques. CTL's which recognize a specific antigenic peptide in association with this class I allele will also be prepared by standard techniques (Yap K and Ada G, Cytotoxic T cells specific for influenza virus-infected target cells. *Immunology* 32: 151-159 (1977)). The 0.174 cells will be aliquoted into the wells of a 96 well cell culture plate. Each well will receive a quantity of a compound to be tested, after which they will be incubated for 90 minutes at 37° C. The 96 well plates will be centrifuged to pellet the 0.174 cells, after which the cells will be resuspended in normal media without any added test compound. The media will contain the specific antigenic peptide. After a further two hour incubation at 37° C., CTLs will be added to each well. Cell lysis will be measured using a standard automated fluorometric assay for T cell toxicity (Brenan M and Parish C. Automated fluorometric assay for T cell toxicity. *J. Immuno*. Methods 112:121-131, 1988). Any well which has received a compound that permits the incompletely assembled MHC class I-$\beta$2M complex to depart the ER, reach the cell surface and bind the antigenic peptide present in the medium will be susceptible to CTL-mediated lysis. A duplicate 96 well assay plate will receive the same chemical compounds but will not receive CTL cells. Detection of cell lysis on this duplicate plate will identify compounds which lyse cells directly, rather than through the MHC-mediated pathway. This assay will permit rapid and reliable identification of compounds which permit the release of incompletely assembled or misfolded proteins from the ER. Furthermore, the assay is designed to be employed in the high throughput screening of libraries consisting of natural products or of combinatorially synthesized chemicals.

Immunodiagnostics/Immunoassays. This group of techniques is used for the measurement of specific biochemical substances, commonly at low concentrations in complex mixtures such as biological fluids, that depend upon the specificity and high affinity shown by suitably prepared and selected antibodies for their complementary antigens. A substance to be measured must, of necessity, be antigenic—either an immunogenic macromolecule or a haptenic small molecule. To each sample a known, limited amount of specific antibody is added and the fraction of the antigen combining with it, often expressed as the bound free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including: enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

Common assay formats include the sand which assay, competitive or competition assay, latex agglutination assay, homogeneous assay, microtitre plate format and the microparticle-based assay.

Enzyme-linked immunosorbent assay (ELISA). ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to 'capture' the relevant antigen (or antibody) in the test solution. The antigen-antibody complex is then detected by measuring the activity of an appropriate enzyme that had previously been covalently attached to the antigen (or antibody).

For information on ELISA techniques, see, for example, J. R. Crowther, *Elisa: Theory and Practice* (*Methods in Molecular Biology*, Vol. 42), Human Pr. (1995); Challacombe and Kemeny, *ELISA and Other Solid Phase Immunoassays: Theoretical and Practical Aspects*, John Wiley & Son Ltd. (1998); D. M. Kemeny, *A Practical Guide to Elisa*, Pergamon Pr. (1991); and E. Ishikawa, *Ultrasensitive and Rapid Enzyme Immunoassay* (*Laboratory Techniques in Biochemistry and Molecular Biology*, V. 27), Elsevier Advanced Technology (1991).

Colorimetric Assays for Enzymes. Colorimetry is any method of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically.

Standard colorimetric assays of beta-galactosidase enzymatic activity are well known to those skilled in the art (see, for example, Norton et al., Molecular & Cellular Biology 5:281-290 (1985)). A calorimetric assay can be performed on whole cell lysates using O-nitrophenyl-beta-D-galactopyranoside (ONPG, Sigma, St. Louis, Mo.) as the substrate in a standard colorimetric beta-galactosidase assay (Maniatis et al., Cold Spring Harbor, N.Y., Cold Spring Harbor Lab. (1990)). Automated colorimetric assays are also available for the detection of beta-galactosidase activity, as described in U.S. Pat. No. 5,733,720.

Immunofluorescence Assays. Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

For general information on immunofluorescent techniques, see, for example, Knapp et al., Immunofluorescence and Related Staining Techniques, Elsevier/North-Holland Biomedical Press (1978); V. J. Allan, *Protein Localization by Fluorescent Microscopy: A Practical Approach* (The Practical Approach Series, 218), Oxford Univ. Press (1999); E. H. Beutner, *Defined Immunofluorescence and Related Cytochemical Methods*, New York Academy of Sciences (1983); and E. O. Caul, *Immunofluorescence Antigen Detection Techniques in Diagnostic Microbiology*, Cambridge Univ. Press (1993). For detailed explanations of immunofluorescent techniques applicable to the present invention, see, U.S. Pat. Nos. 5,912,176; 5,869,264; 5,866,319; and 5,861,259.

P. Combinatorial Chemistry

Combinatorial chemistry can be utilized to generate compounds which are chemical variations of compounds useful in the present invention. Such compounds can be evaluated using the high-throughput screening methods of the present invention. Basic combinatorial chemistry concepts are well known to one of ordinary skill in the chemical arts and can also be found in Nicholas K. Terrett, *Combinatorial Chemistry* (*Oxford Chemistry, Masters*), Oxford Univ. Press (1998); Anthony W. Czarnik and Sheila Hobbs Dewitt (Editors), *A Practical Guide to Combinatorial Chemistry*, Amer. Chemical Society (1997), Stephen R. Wilson (Editor) and Anthony W. Czarnik (Contributor), *Combinatorial Chemistry: Synthesis and Application*, John Wiley & Sons (1997); Eric M. Gordon and James F. Kerwin (Editors), *Combinatorial Chemistry and Molecular Diversity in Drug Discovery*, Wiley-Liss (1998); Shmuel Cabilly (Editor), *Combinatorial Peptide Library Protocols* (*Methods in Molecular Biology*), Human Press (1997); John P. Devlin, *High Throughput Screening*, Marcel Dekker (1998); Larry Gold and Joseph Alper, Keeping pace with genomics through combinatorial chemistry, *Nature Biotechnology* 15, 297 (1997); Aris Persidis, Combinatorial chemistry, *Nature Biotechnology* 16, 691-693 (1998).

Q. Modifying Thapsigargin, Cyclopiazonic Acid, DBHQ, and Curcumin to increase therapeutic efficacy Thapsigargin, cyclopiazonic acid, 2,5-di-(tert-butyl)-1,4-hydroquinone (DBHQ), and curcumin inhibit the ER Ca-ATPase, resulting in the transient elevation of cytosolic calcium levels and the depletion of ER calcium stores. While this activity underlies the proposed therapeutic benefit of these compounds in CF, it is possible that it may also produce toxic side effects by activating calcium-dependent processes in a wide variety of cells. Since the primary affected organ in CF is the lung, correction of the CF defect in airway epithelial cells would dramatically reduce the morbidity associated with this disease. It would be desirable, therefore, to construct derivatives of these compounds which could be applied locally to the airway by aerosol inhalation and which would not diffuse out of the airway epithelial cells to enter the systemic circulation. Such derivatives would be much less likely to exhibit systemic toxic side effects.

A non-specific esterase activity is present in the cytoplasm of most eukaryotic cell types. This activity has been exploited in the design of numerous compounds whose purpose is to enter the cytoplasm of target cells and subsequently remain trapped there. These compounds, which include several indicator dyes used to measure intracellular ionic concentrations, are synthesized as acetoxymethylesters (Grynkiewicz G, Poenie M and Tsien R Y, A new generation of Ca indicators with greatly improved fluorescence properties, *J. Biol. Chem.* 260:3440-3450 (1985)). In this form they are membrane permeant and can diffuse across the cell membrane to enter the cytoplasm. The action of the cytoplasmic esterase removes methanol groups, leaving behind negatively charged carboxylic acid residues on the compound of interest. In this charged state, the compound is no longer membrane permeant and it is thus trapped in the cytosol.

Thapsigargin, cyclopiazonic acid, DBHQ, and curcumin may be modified to incorporate acetoxymethylester groups. These modified compounds would then be administered by aerosol inhalation. Presumably, they would enter the surface airway epithelial cells by diffusing across their apical plasma membranes. Once inside the airway epithelial cells, they would become substrates for the action of the cytoplasmic esterase. Esterase action on the derivatized compounds would leave these compounds with negatively charged carboxylic acid residues, thus preventing their departure from the airway epithelial cells. Consequently, the compounds would only gain access to and exert effects upon airway epithelial cells, which are their intended target. The potential for systemic side effects would thus be greatly reduced.

This strategy will succeed only if the addition of one or more carboxylic acid groups to thapsigargin, cyclopiazonic acid, DBHQ, or curcumin does not markedly reduce their inhibitory effects on the ER Ca-ATPase. No modifications may be necessary to reduce the toxicity of at least some of these compounds. Animal toxicity has not been associated with DBHQ (Chao et al., Calcium- and CaMKII-dependent chloride secretion induced by the microsomal Ca-ATPase inhibitor 2,5-di-(tert-butyl)-1,4-hydroquinone in cystic fibrosis pancreatic epithelial cells, *J. Clin. Invest.* 96:1794-1801 (1995)) or with curcumin.

R. PHARMACEUTICAL PREPARATIONS

General. The therapeutics compositions of this invention can be used in the form of a medicinal preparation, for example, in solid, semi-solid or liquid form which contains the composition of the present invention, as an active ingredient, in admixture with an organic or inorganic carrier or excipient suitable for external, enteral or parenteral applications. The active ingredient may be compounded, for example, with the usual non-toxic pharmaceutically acceptable carriers for tablets, pellets, capsules, inhalants, suppositories, solutions, emulsions, suspensions, and any other form suitable for use. Formulations of the present invention encompass those which include carriers such as water, talc, glucose, lactose, gum acacia, gelatin, mannitol, starch paste, magnesium trisilicate, corn starch, keratin, colloidal silica, potato starch, urea and other carriers suitable for use in manufacturing preparations, in solid, semisolid or liquid form and in addition auxiliary, stabilizing, thickening and coloring agents and perfumes may be used.

Solid Compositions. For preparing solid compositions such as tablets or capsules, the principal active ingredients are mixed with a pharmaceutical carrier (e.g. conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of a composition of the present invention, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as tablets, pills and capsules. This solid preformulation composition is then subdivided into unit dosage forms of appropriate amounts.

The tablets or pills of the novel composition can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate. The active compounds may also be formulated in rectal compositions such as suppositories or retention enemas, e.g., containing conventional suppository bases such as cocoa butter or other glycerides.

Inhalants. For intranasal administration or administration by inhalation, the active compounds are conveniently delivered in the form of a solution or suspension from a pump spray container that is squeezed or pumped by the patient, or as an aerosol spray presentation from a pressurized container or nebulizer, with the use of a suitable propellant (e.g., dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of an active compound and a suitable powder base such as lactose or starch.

Thapsigargin treatment leads to acute elevations of cytosolic calcium concentrations in a wide variety of cell types (Hofer and Machen, *Proc. Nat. Acad. Sci.* 90:2598-2602 (1993)). Since release of calcium from intracellular stores acts as a second messenger controlling an enormous list of critical cellular processes, including muscle contraction, hormone secretion and neuronal communication (Berridge, *Mol. Cell. Endocrin.* 98:119-24 (1994)) it is perhaps surprising that thapsigargin is so well tolerated when administered in nebulized form. The chemical structure of thapsigargin includes 3 ester groups (Christensen et. al, *FEBS Lett.* 335: 345-348 (1993)). The cytoplasm of most eukaryotic cells is richly endowed with non-specific esterase activity, which has been shown to rapidly de-esterify xenobiotic compounds that enter the cells by diffusion (Tsien et al., *J. Cell Biol.* 94:325-334 (1982)). It is likely, therefore, that after entering airway epithelial cells by diffusion across their apical membranes, thapsigargin is modified by the esterase activity. Loss of the ester groups reduces thapsigargin's efficacy as a calcium pump inhibitor by at least 40-fold (Christensen et. al., supra). Thus thapsigargin may possess the desirable pharmacologic characteristic of being converted at its target organ into an inactive metabolite.

If this is indeed the case, thapsigargin can be applied locally to the airway by aerosol inhalation and does not diffuse out of the airway epithelial cells to enter the systemic circulation in a bioactive form. Future derivatives that exploit this feature might be even less likely to exhibit systemic toxic side effects. It is also interesting to note that no toxicity may be associated with at least some compounds that should mimic the desired thapsigargin effect. No animal toxicity has been attributed to DBHQ or curcumin, compounds that share thapsigargin's ability to inhibit ER Ca-ATPase activity. (Chao et al., *J. Clin. Invest.* 96:1794-1801 (1995)).

Finally, other classes of compounds in addition to calcium pump inhibitors are also likely to be of potential therapeutic utility in treating clinical conditions associated with ER retention of mis-folded proteins. Any compound which directly inhibits the function of the ER retention chaperone machinery or which alters the environment of the ER lumen so that these proteins can not function properly may possess potential clinical value.

Liquid Forms. The liquid forms, in which the novel composition of the present invention may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

Buccal Administration. For buccal administration, the composition may take the form of tablets or lozenges formulated in conventional manners.

The active compounds may be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

Formulations. Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Without further description, it is believed that one of ordinary skill in the art, using the preceding description and the following illustrative examples, can make and utilize the compounds of the present invention and practice the claimed methods.

EXAMPLES

The following working examples which disclose effects of thapsigargin or curcumin treatment in vitro and in vivo in cell lines and/or in a mouse model of cystic fibrosis specifically point out certain embodiments of the present invention. These examples are not to be construed as limiting in any way the scope of the invention. Other examples involving ER chaperone and UGGT regulation as well as other proteins that regulate intracellular targeting of mis-folded proteins will be apparent to the skilled artisan. Assays analogous to those described below can be utilized in examining other agents that regulate UGGT or other proteins that regulate mis-folded proteins.

Tissue Culture/Cell Lines

IB3-1 (Zeitlin et al., 1991) and CFBE29O$^-$ (Kunzelman et al., *Am. J. Resp. Cell. Mol. Biol.* 8:522-529. (1993)) cells are CF-affected airway epithelial cell lines. Both IB3-1 and CFBE29O$^-$ are immortalized, well-characterized human bronchial epithelial cell lines derived from CF-patients. The cell lines retain the diagnostic feature of CF-affected epithelial cells: a lack of cAMP-stimulated, PKA-activated Cl$^-$ channel activity. Genotypically, IB3-1 is a compound heterozygote containing the $\Delta$F508 mutation and W1282X, a nonsense mutation with a premature termination signal. The W1282X mutation does not result in a stable mRNA and yields no protein (Hamosh et al., *Hum. Mol. Gen.* 1:542-544. (1992)). Therefore, the only stable CFTR protein produced in the IB3-1 cells is the $\Delta$FF508 product.

The CFBE29O$^-$ cell line is derived from a patient homozygous for the $\Delta$F508 mutation. Both cell lines were grown at 37° in 5% $CO_2$. The IB3-1 cells were maintained in LHC-8 media (Biofluids) supplemented with 5% fetal calf serum, tobramycin (20 ug/ml), penicillin (100 U/ml), streptomycin (100 ug/ml). The CFBE29O$^-$ cells were maintained in Dulbucco's Modified Eagles medium (DMEM) supplemented with 10% fetal calf serum, tobramycin (20 ug/ml), penicillin (100 U/ml), and streptomycin (100 ug/ml).

The CFPAC-1 cell line is a ductal pancreatic adenocarcinoma cell line derived by differential trypsinization of explant cultures from a metastatic lesion in the liver of a 26 year old male with CF (Schoumacher et al., *Proc. Natl. Acad. Sci.* 87:4012-4016 (1990)). The cell line is homozygous for expression of $\Delta$F508 CFTR and has the ion transport properties of CF-affected epithelia. CFPAC-1 cells show epithelial morphology and polarization with apical microvilli.

CFPAC cells were grown at 370 in 5% $CO_2$ and maintained in Isocove's modified Dulbucco's medium supplemented with 10% fetal calf serum. Both for measurements of short circuit current and for immunofluorescence experiments, these cells were grown on collagen coated permeable supports (Transwell Snapwell filter cups, Corning Costar, Cambridge, Mass.). The well characterized T84 intestinal epithelial cell line was grown according to standard methods (Cohn et al., *Proc. Nat. Acad. Sci.* 89:2340-2344 (1992); Bell and Quinton, *Am. J. Physiol.* 262:C555-C562 (1992)) and were also plated on permeable supports for short circuit current assays.

Experiment 1. Patch Clamp Analysis.

Materials and Methods. Single channel patch clamp studies were performed using conventional procedures on the CF-affected bronchial epithelial cell lines, IB3-1 and CFBE29O$^-$ (Egan et al., *Am. J. Physiol.* 268:C243-C251 (1995)). Cells were grown in culture flasks on glass chips coated with collagen (150 ug/ml), fibronectin (10 ug/ml), and bovine serum albumin (10 ug/ml).

When cells were at 75% confluence they were incubated with 1 uM thapsigargin (or vehicle alone) for 1.5 hours at 37° C. using the following protocol. First, the LHC-8 media or DMEM was removed from the tissue culture dish and the cells were rinsed with phosphate buffered saline. Fresh LHC-8 media containing 1 uM thapsigargin was added to the cell culture dish. After the 1.5 hour thapsigargin exposure, cells were rinsed with fresh media and allowed to incubate for 2 hours at 37° C. prior to patch clamping. The patch clamp bath solution contained (in mM) 150 NaCl, 2 $MgCl_2$, 1 EGTA, 5 HEPES, and 0.5 CaCl$_2$, pH=7.3. The pipette solution contained (in mM) 150 NaCl, 2 MgCl$_2$, 5 HEPES, and 2 CaCl$_2$, pH=7.3.

Patch clamp studies were performed at 22-25 C. Data were amplified on an Axopatch 200A patch clamp amplifier and recorded on videotape for later analysis. Data were low pass filtered and digitized at 1 kHz. Data were analyzed using Pclamp6.

Results. The surface expression of ΔF508 CFTR was initially examined by patch clamp analysis performed on two different treated and untreated CF-affected respiratory epithelial cell lines, IB3-1 (Zeitlin et al., *Am. J. Resp. Cell. Mol. Biol.* 4:313-319 (1991)) and CFBE290⁻ (Kunzelman et al., *Am. J. Resp. Cell. Mol. Biol.* 8:522-529 (1993)).

In the untreated CF-affected cells, no low conductance chloride channels could be activated with a cAMP-stimulation cocktail containing IBMX and forskolin (FIG. 1A). These findings are consistent with the primary CF defect. In contrast, treatment with thapsigargin dramatically enhanced the IB33-1 and CFBE290⁻ cells' chloride conductance.

Figure 1B:
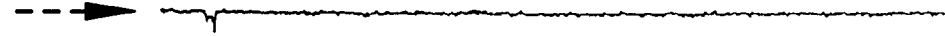
Figure 1B:
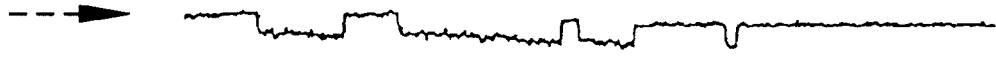
Figure 1B:
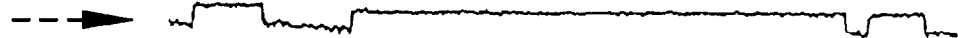
Figure 2A:
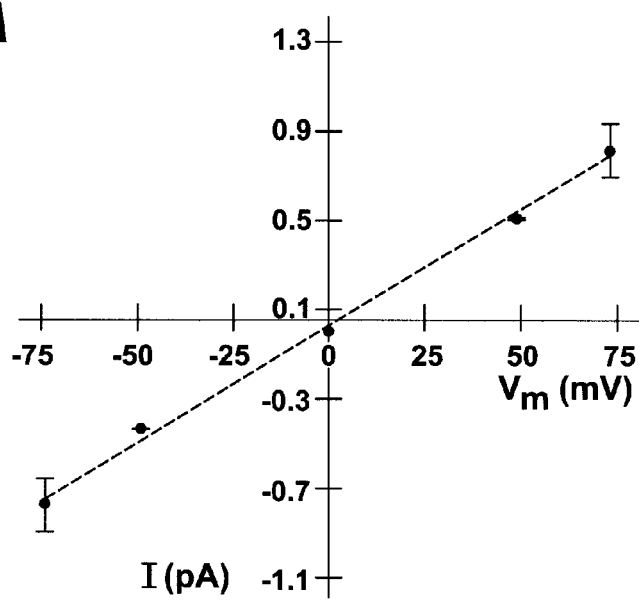
Figure 2B:
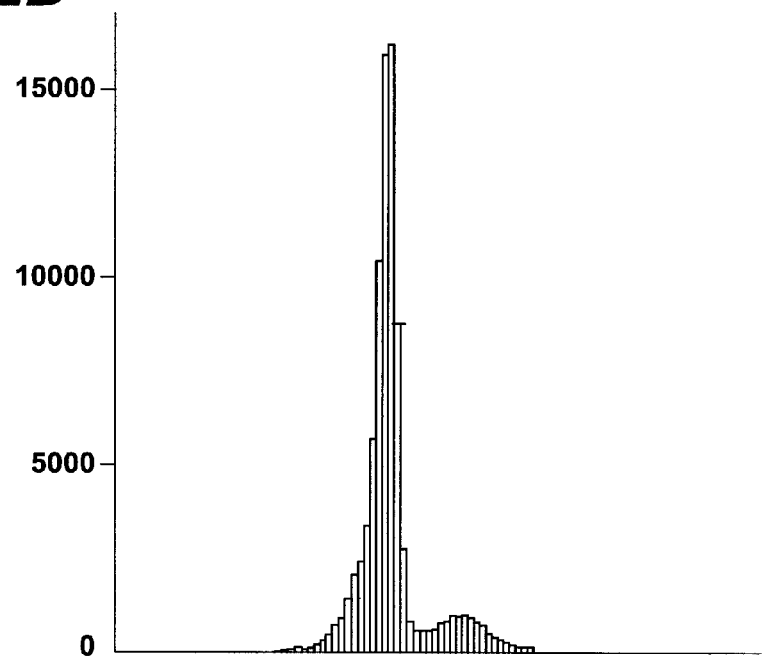

Cells were incubated in 1 µM thapsigargin for 90 minutes, after which they were incubated for 2 hours in the absence of the drug. Patch clamp analysis of the treated cells revealed that their plasma membranes now contained abundant low conductance chloride channel activity (FIG. 1B and Table 1). The biophysical characteristics of the channel activity were consistent with those of the channel formed by the ΔF508 CFTR protein (Dalemans et al., *Nature* 354:526-528 (1991); Egan et al., *Am. J. Physiol.* 268:C243-C251 (1995); Rubenstein et al., *J. Clin. Invest.* 100:2457-2465 (1997); Haws et al., *Am. J. Physiol.* 270:C1544-C11555. (1996); Hwang et al., *Am J Physiol.* 273:C988-998 (1997)). Thus, the current versus voltage relationship is linear (FIG. 2A), revealing an average single channel conductance of 11.8 pS. Furthermore, analysis of an open state histogram (FIG. 2B) produces a calculated $P_c$ of 0.12. Channel activity could be inhibited by glibenclamide (data not shown). The levels of functional expression achieved through the manipulation (Table 1) are in line with the level of expression that has been suggested to be required to reverse the cystic fibrosis defect (Johnson et al., Nature Gen. 2:21-25 (1992)).

Patch clamp experiments were also carried out on thapsigargin-treated cells after they were allowed to incubate for 8 hours or 24 hours following a single thapsigargin exposure to determine how long the effect of this treatment on the expression of the CFTR-like channel could persist. After an 8 hour recovery period CFTR-like channel activity was observed in 7 of 20 excised patches (35%). However after a 24 hour recovery period 0 of 10 patches (0%) demonstrated any CFTR-like channel activity.

Treatment with calcium pump inhibitors leads to a transient rise in intracellular calcium concentrations, which has been shown to acutely stimulate chloride currents in CF epithelial cells (Chao et al. *J. Clin. Invest.* 96:1794-1801 (1995)). To ascertain if the change in CFTR channel activity was due to this short term effect of thapsigargin, cells were treated with a short exposure to thapsigargin (15 minutes) and then allowed to recover for 2 hours prior to patch clamping. No CFTR-like channel activity was stimulated in 10 patches following this protocol (data not shown), suggesting that short-term elevations of intracellular calcium concentrations that follow treatment with thapsigargin do not result in detectable long term increases in CFTR-like channel activity.

TABLE 1

| Cell Type | Incubation Condition | Patches with CFTR channel activity |
|---|---|---|
| IB3-1 | control, no treatment | 0/10 (0%) |
|  |  | (in previous studies 0/35) |
| CFBE290⁻ | control, no treatment | 0/8 (0%) |
| IB3-1 | thapsigargin treated | 25/76 (32.8%) |
| CFBE290⁻ | thapsigargin treated | 8/24 (33.3%) |
| Combined | control, no treatment | 0/28 (0%) |
| Combined | thapsigargin treated | 33/100 (33%) |

[1]Note: Normally in unaffected airway epithelial cells CFTR channel activity can be detected via patch clamp techniques in 70% of patches.

Experiment 2. Short Circuit Current Measurements.

Materials and Methods. CFPAC-1 or T84 cells were grown on collagen coated permeable supports (Transwell Snapwell filter cups, Corning Costar, Cambridge, Mass.). Cells were fed every one to two days from the basolateral surface of the monolayer while the apical surface was exposed to the humidified 5% CO$_2$ environment. Filters were cultured until a tight monolayer was achieved.

Prior to electrical studies some of the monolayers were treated with 1 uM thapsigargin using the following protocol. Culture media containing 1 uM thapsigargin was added to the apical surface of the monolayer and incubated for 1.5 hours at 37° C. Cells were then rinsed with fresh thapsigargin-free media and allowed to incubate for 2 hours at 37° C., after which they were used for Ussing chamber studies. The Ussing chamber bath solution was a nominally bicarbonate-free Ringer's solution that was composed of (in mM) 140 NaCl, 1.2 MgCl$_2$, 5 K$_2$HPO$_4$, 0.5 KH$_2$PO$_4$, 5 HEPES, 1.2 CaCl$_2$, and 5 glucose pH=7.4. Bath solutions were warmed to 37° C.

Ag—AgCl wires were embedded in 3M KCl agar bridges were used as voltage and current electrodes on each side of the monolayer contained in an Ussing chamber system (World Precision Instruments, WPI). Voltage was clamped using an EC-825 voltage clamp amplifier (Warner Instruments) with a digital current and voltage readout. The transepithelial potential difference ($V_{tc}$) is continuously recorded. At 5-minute intervals the $V_{tc}$ is clamped to 0 and the short circuit current ($I_{sc}$) was determined. Under $I_{sc}$ conditions a voltage pulse between 20 and 40 mV was applied and the change in current was used to calculate the transepithelial resistance ($R_{tc}$).

After cells were mounted in the Ussing chamber electrical parameters were assessed for 20 to 30 minutes (control period). Following the control period a cAMP-stimulating cocktail (10 uM forskolin and 100 uM IBMX) was added to the apical chamber. Electrical parameters were monitored for 20-30 minutes following this treatment to assess for changes in $I_{se}$, $V_{te}$, and $R_{te}$. Furosemide (10 M), an inhibitor of chloride secretion, was then added to the basolateral bath for 20 minutes to assess its affect on chloride secretion. In the continued presence of furosemide, $10^{-4}$M amiloride, an inhibitor of sodium absorption, was added to the apical bath for 10 minutes. During these maneuvers, electrical parameters were continuously monitored.

Figure 3:
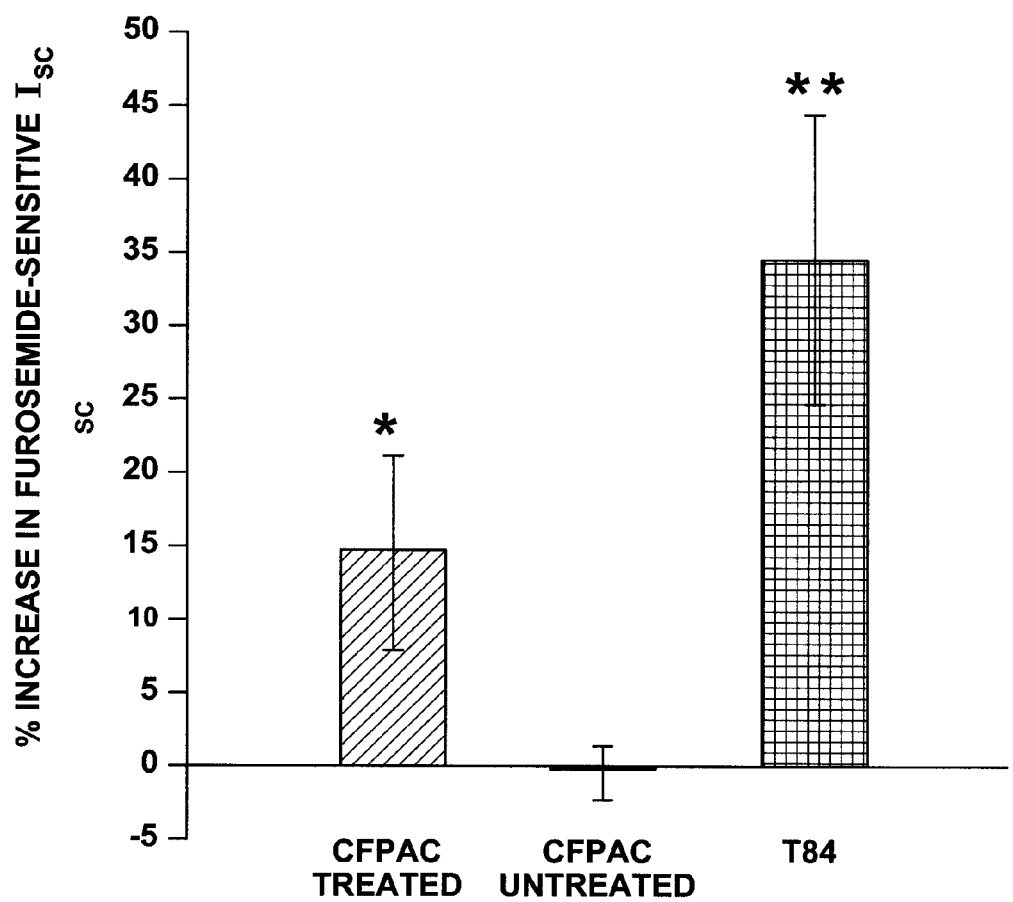
Figure 4A:
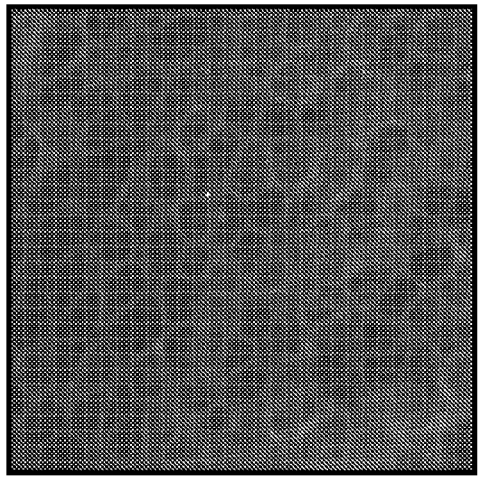
Figure 4B:
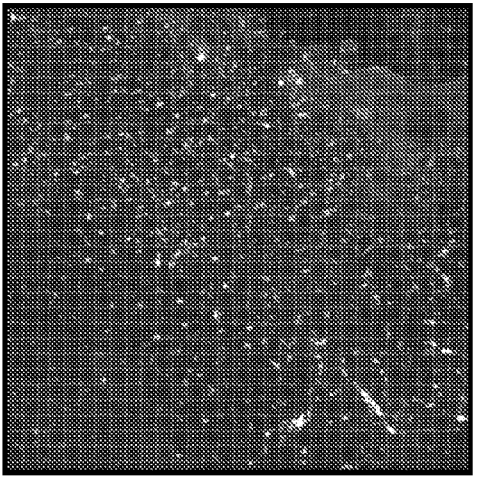
Figure 4C:
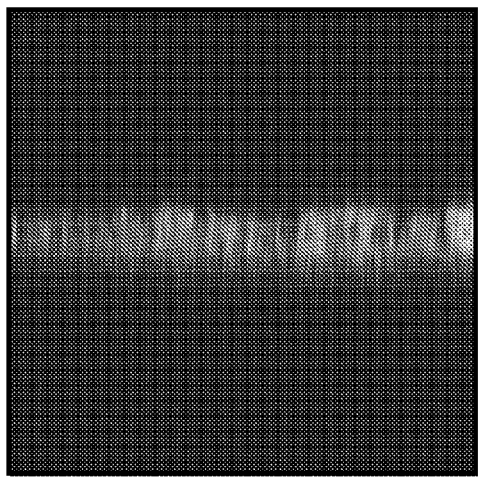
Figure 4D:
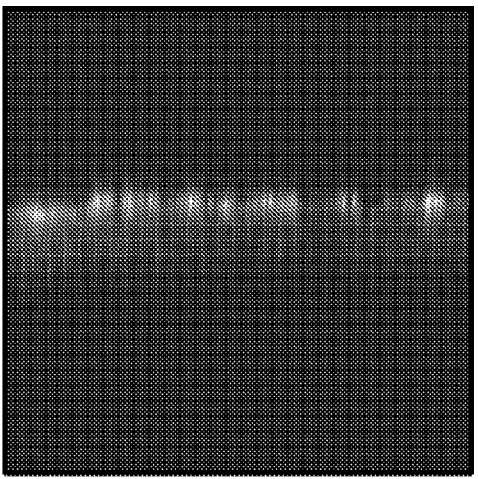
Figure 5A:
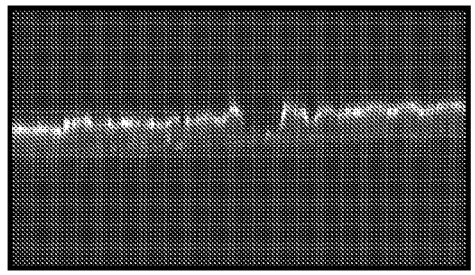
Figure 5B:
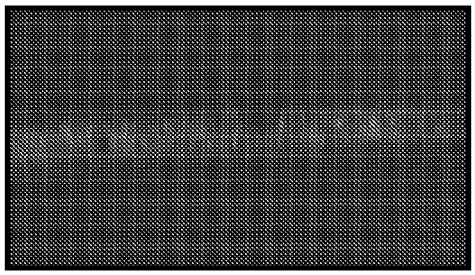
Figure 5C:
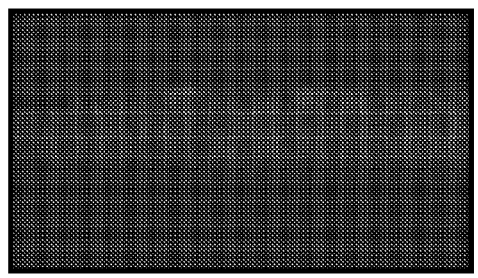
Figure 5D:
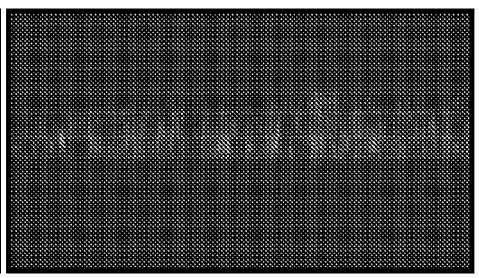
Figure 5E:
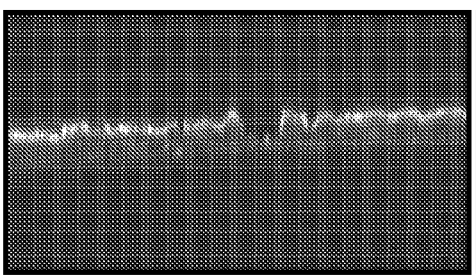
Figure 5F:
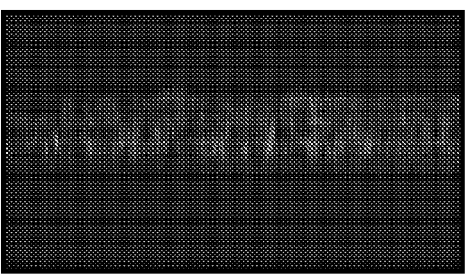

Results. To determine whether the thapsigargin effect on CFTR channel activity is of sufficient magnitude to increase epithelial short circuit current, CFPAC-1 cells (Schoumacher et at., *Proc. Natl. Acad. Sci.* 87:4012-4016 (1990)) were grown on collagen-coated permeable supports and examined in Ussing chambers. When monolayers of untreated CFPAC-1 cells were exposed to a cAMP-stimulation there was no increase in the short circuit current (−0.38±1.8%, n=12) (FIG. 3). The lack of response to the elevation of cytosolic cAMP concentrations is consistent with the CF phenotype (Grubb et al. *Am. J. Resp. Cell. Mol. Bio.* 8:454-460 (1993)).

In contrast, when thapsigargin treated CFPAC-1 monolayers were exposed to the cAMP-stimulation cocktail, there was a 14.6±6.6% increase in short circuit current (n=12, p=0.02) which was inhibited by furosemide, suggesting it was due to an increase in net chloride secretion. The presence of the cAMP-stimulated chloride secretion in the thapsigargin-treated CFPAC cells is consistent with a partial correction of the CF ion transport defect and it is similar in magnitude to that seen with T84 cell monolayers (FIG. 3). T84 cells are a human colonic epithelial cell line that expresses high levels of wild-type CFTR (Cohn et al., *Proc. Nat. Acad. Sci.* 89:2340-2344. (1992); Bell and Quinton, *Am. J. Physiol.* 262:C555-C562. (1992)).

Experiment 3. Immunofluorescence Analysis.

CFPAC and CFBE290⁻ epithelial cells were grown to confluence on 0.45 micron Transwell filter inserts (Corning Costar, Cambridge, Mass.) under the same conditions described for the short circuit current measurements. Prior to immunofluorescence analysis, filter grown cell monolayers were treated for 90 min with 1 µM thapsigargin at 37° C., present in both the apical and basolateral media compartments. The media was then changed to standard Iscove's growth medium or DMEM without thapsigargin, and cells were incubated for 2 or 4 hours at 37° C. Control cells underwent the same media changes but were not subjected to thapsigargin treatment.

Following the second incubation, the filter grown monolayers were washed once with phosphate buffered saline supplemented with calcium and magnesium (150 mM NaCl, 10 mM $NaP_i$, pH 7.4, 1 mM $MgCl_2$, 0.1 mM $CaCl_2$), after which they were fixed for 10 minutes in −20° C. 100% methanol. Immunofluorescence labeling was performed using the well characterized 169 and 181 antibodies (gift of W. Guggino, Johns Hopkins University) directed against the R domain and the prenucleotide binding fold of the CFTR protein, respectively (Crawford et al., *Proc. Nat. Acad. Sci.* 88:9262-9266 (1991)) and a monoclonal antibody directed against the α-subunit of the Na,K-ATPase (Gottardi and Caplan, *J. Cell Biol.* 121:283-293 (1993)).

Incubations with primary and rhodamine-conjugated secondary antibodies were performed as previously described (Gottardi and Caplan, Id.). Labeled cells were examined using a Zeiss LSM 410 laser scanning confocal microscope. All images are the product of 8-fold line averaging. Contrast and brightness settings were chosen so that all pixels were in the linear range. YZ cross sections were generated using a 0.2 µmotor step.

Results. To examine further the effects of thapsigargin on the subcellular distribution of the ΔF508 protein, we performed immunofluorescent localization of the CFTR protein in treated and untreated CFPAC cells. In untreated cells, CFTR staining is barely detectable in a diffuse cytoplasmic pattern surrounding the nucleus (FIG. 4). This pattern is consistent with the localization of the ΔF508-CFTR protein to the ER in the untreated cells. In treated cells, viewed both en face and in XZ cross section, bright labeling of apical microvilli could be detected in most of the cells. Cells that were incubated for 2 hours following the thapsigargin treatment exhibited only apical staining. No intracellular ER labeling could be detected in these cells. Cells that were incubated for 4 hours following the thapsigargin treatment exhibiting CFTR staining both at the apical membrane and in the ER (data not shown). Thus, treatment with thapsigargin leads to redistribution of the mutant ΔF508-CFTR protein from the ER to the apical membrane.

As evidenced by the pattern observed in cells incubated for 4 hours after the removal of thapsigargin, ΔF508-CFTR protein synthesized following the removal of the drug is retained in the ER. These observations are consistent with the interpretation that thapsigargin treatment permits mis-folded ΔF508-CFTR protein to be released from the ER and travel to its appropriate site of functional residence at the apical plasma membrane.

It is likely that the mechanism through which thapsigargin effects the redistribution of the ΔF508 CFTR protein from the ER to the cell surface is related to this compound's capacity to reduce the ER's intralumenal $Ca^{++}$ concentration. It is also possible, however, that thapsigargin might interact directly with the ΔF508 CFTR protein to alter its tertiary structure. CFTR is related to the MDR family of ABC transport proteins. Members of the MDR family are capable of interacting with and transporting a wide variety of chemical compounds (Higgins, *Ann. Rev. Cell Biol.* 8:67-113 (1992)). It has been demonstrated that MDR proteins that carry mutations resulting in mis-folding and ER retention can be functionally rescued through exposure to compounds that are substrates for the particular MDR protein's transport activity (Loo and Clarke, *J. Biol. Chem.* 272:709-712 (1997); Loo and Clarke, *J. Biol. Chem.* 273:14671-14674 (1998)). Presumably, binding substrate compounds stabilizes the protein's conformation sufficiently to permit it to elude the ER's quality control machinery.

In light of the homology relating CFTR to the MDR proteins, it is possible that thapsigargin exerts its effect on ΔF508-CFTR through a similar mechanism. If CFTR manifests an MDR-like activity, thapsigargin could conceivably be a substrate analogue whose interaction with a binding site on CFTR could stabilize and modify this protein's structure. According to this model, thapsigargin's effect on calcium pumps and ER lumenal calcium concentrations would not be relevant to its mode of action in rescuing ΔF508-CFTR.

To test this possibility, we exposed CFBE290⁻ cells to the calcium pump inhibitors DBHQ and cyclopiazonic acid, which are structurally unrelated to thapsigargin (Khan et al., *Biochem.* 34:14385-14393 (1995); Whitcome et al., *Biochem. J.* 310:859-868 (1995)). As assayed by immunofluorescence microscopy (data not shown), both compounds were able to recapitulate thapsigargin's capacity to induce ΔF508-CFTR surface delivery. Since DBHQ and cyclopiazonic acid are chemically quite distinct from thapsigargin and from each other, it is likely that their effects on ΔF508-CFTR arise from their shared capacity to release calcium from the ER lumen rather than from any direct interaction with the CFTR protein itself.

To ensure that thapsigargin-induced appearance of immunoreactive ΔF508-CFTR at the plasma membrane is due to the release of an ER retained cohort rather than to stimulation of new ΔF508-CFTR synthesis, protein synthesis was blocked during thapsigargin treatment and post-treatment chase periods through the addition of 10 mm cycloheximide. Inhibition of protein synthesis did not abrogate the thapsigargin effect (data not shown), demonstrating that thapsigargin releases a pre-synthesized pool of ΔF508-CFTR to the cell surface.

While not wishing to be bound by any theory, we speculate that thapsigargin exerts its effect by reducing the ER's intralumenal $Ca^{2+}$ concentration, thus interfering with the functioning of calcium-dependent chaperone mechanisms. To establish whether the thapsigargin effect is indeed due to a reduction in intraorganellar $Ca^{2+}$ rather than the consequent rise in cytosolic $Ca^{2+}$, we repeated the experiment in cells preloaded with BAPTA, which should chelate $Ca^{2+}$ released into the cytosol by thapsigargin treatment (Tsien, R. Y., *Biochem.* 19, 2396 (1980)). The presence of BAPTA did not inhibit the thapsigargin-induced delivery of ΔF508-CFTR to the cell surface (data not shown), demonstrating that this effect is not due to increases in cytoplasmic $Ca^{2+}$ concentration.

Experiment 4. Nebulized Thapsigargin.

A nebulization chamber was constructed using an 8 quart plastic container with a lid that creates an air tight seal. A 'T piece nebulizer device' (Hudson RCI T-up Draft Nebumist Nebulizer) was inserted into the container via an opening located on the side of the chamber. The nebulization device was filled with 5 mls of 1 µM thapsigargin dissolved in physiologic saline solution. The gas source (high pressure air) was attached to the set up to create a flow rate of $\geq 12$ liters per minute. Flow was adjusted to maintain a fine visible mist throughout the chamber. Numerous small ventilation holes were placed at the top of the chamber to ensure the escape of carbon dioxide. The nebulization chamber was kept in a fume hood during the experiments to allow for dispersion of any escaped mist.

Mice or cells were placed into the chamber prior to the onset of nebulization. Mice were observed continuously during the nebulization treatments and observations were documented every 15-30 minutes. Lungs were prepared for histologic analysis according to methods described previously (Courtois-Coutry et al., *Cell* 90:501-510 (1997)).

Results. Thapsigargin treatment results in the transient elevation of cytosolic calcium levels and the depletion of ER calcium stores (Hofer and Machen, *Proc. Nat. Acad. Sci.* 90:2598-2602 (1993), Montero et al., *J. Cell Biol.* 139:601-611 (1997)). While this activity underlies the proposed therapeutic benefit of these compounds in CF, it is possible that it may also produce toxic side effects by activating calcium-dependent processes in a wide variety of cells (Berridge, *Mol. Cell. Endocrin.* 98:119-24 (1994)). Since the primary affected organ in CF is the lung (Davis et al., *Am. J. Respir. Crit. Care Med.* 154:1229-1256 (1996); Pilewski and Frizell, *Physiol. Rev.* 79:Suppl: S215-S255 (1999); Rosenstein and Zeitlin, *Lancet* 351:277-282 (1998); Johnson et al. *Nature Gen.* 2:21-25 (1992)), correction of the CF defect in airway epithelial cells would dramatically reduce the morbidity associated with this disease. It is important, therefore, to determine whether therapeutically efficacious doses of thapsigargin applied directly to the lung by inhalation are clinically tolerable.

To examine this issue, six mice were exposed for 3 to 4 hours per day for 14 days to a nebulized solution of 1 µM thapsigargin in normal saline. The animals exhibited no obvious ill effects either during or between treatments. At the end of the 2 week trial, the animals were sacrificed and 4 were processed for histopathologic examination of the lungs. In all cases, the cellular architecture of the lungs (i.e., alveolar and bronchiolar architecture) was completely normal (See FIG. 8). One of the specimens exhibited a moderate peribronchiolar lymphocytic infiltration, while in the other 3 the density of peribronchiolar lymphocytes was within normal limits (data not shown).

To ensure that the dose of thapsigargin received by the mice was sufficient to rescue ΔF508-CFTR in airway epithelial cells, we examined the effect of nebulized thapsigargin on CFBE290⁻ cells. These airway epithelial cells were cultured on permeable filter supports and grown with an air-liquid interface. Thus, their apical membranes are separated from the atmosphere by only a thin film of fluid, as are the apical membranes of airway epithelial cells in situ (Davis et al., *Am. J. Respir. Crit. Care Med.* 154:1229-1256 (1996); Pilewski and Frizell, *Physiol. Rev.* 79:Suppl: S215-S255 (1999)). Filter-grown CFBE290⁻ cells were exposed to 1 µM nebulized thapsigargin for 3 hours and the distribution of ΔF508-CFTR was evaluated by immunofluorescence.

As can be seen in FIG. 5, treatment of cells with nebulized thapsigargin was sufficient to produce a dramatic redistribution of ΔF508-CFTR to the apical plasmalemma. Since the upper airway epithelial cells in the mice must have experienced a dose of thapsigargin similar to that received by the cultured cells, it would appear that mice tolerate long-term doses of thapsigargin sufficient to produce a clinical effect without experiencing any readily detectable or significant physiologic morbidity.

Experiment 5. Secretion of α1-Antitrypsin from Secretion Incompetent Null Variant Affected-Hepatocytes After Thapsigargin Treatment.

Experiment 2 is repeated using a cell line that expresses a retention mutation for cc1-antitrypsin, such as the secretion-incompetent variant, null (Hong Kong), retained in stably transfected mouse hepatoma cells (*J. Biol. Chem.* 269:7514-7519 (1994)). Changes in the cell phenotype are assessed by assaying cells for secretion of a 1-antitrypsin (detailed description in *J. Biol. Chem.* 268:2001-2008 (1993)).

Briefly, cell monolayers are pulse labeled with [³⁵S] methionine for 30 minutes, after which the radiolabeled media is removed and replaced with media containing an excess of unlabeled methionine. During the chase period, one set of monolayers is treated with 1 µM thapsigargin for 3 hours, while another set is incubated for 3 hours in drug free media. Secretion of α1-antitrypsin into the media is assessed by immunoprecipitation followed by electrophoresis and autoradiography.

Results. Cells expressing the secretion-incompetent variant of α1-antitrypsin, null (Hong Kong), are pulse labeled for 30 minutes with [³⁵S] methionine, after which they were incubated in non-radioactive media for 3 hours in the presence or absence of 1 µM thapsigargin. After this chase incubation, the media is collected and subjected to immunoprecipitation with anti-α1-antitrypsin antibodies. Immunoprecipitates are analyzed by SDS-PAGE followed by autoradiography.

Radiolabeled α1-antitrypsin protein is present in the media ftom thapsigargin treated cells and is absent from media collected from untreated cells. These results demonstrate that thapsigargin treatment releases the mis-folded α1-antitrypsin protein from the endoplasmic reticulum and allows it to be secreted from the cell.

Experiment 6. Toxicity Tests for Thapsigargin.

Genetically uniform lab mice were given either normal drinking water (control) or drinking water which contained thapsigargin (1 µM final concentration). The non-control group of mice were given the thapsigargin-treated water over a 3 to 7 day time period. There were no deaths, illnesses or side effects noted in the mice that were given the thapsigargin water (same as control group).

Experiment 7. Western Blot Analysis Establishes Maturation of the ΔF508-CFTR Protein in Thapsigargin-Treated Cells.

Materials and Methods. CFPAC cells were grown to confluence in 10 cm² plates (Corning Costar, Cambridge, Mass.). Following thapsigargin treatment performed as described in Example 3, cells were harvested by scraping in PBS, lysed by sonication, and a crude membrane pellet was recovered by centrifugation at 50,000×g for 2 hrs. Electrophoresis and Western blotting were performed as described (Gottardi, C. J. and Caplan, M. J., *J. Cell. Biol.* 121, 283 (1993)). CFTR protein was detected using an antibody directed against the CFTR nucleotide binding domain 1 (Catalog number 05585, clone L12B4) from Upstate Biotechnology (Lake Placid N.Y.).

Results. FIG. 6 presents a Western blot comparing the level of mature CFTR in thapsigargin treated and untreated CFPAC cells. Lane 3 is a positive control showing the ~170 kDa mature form of the ΔF508-CFTR protein in T84 cells. In untreated CPFAC cells no mature CFTR could be detected in whole lysates, consistent with the retention and degradation of the ΔF508-CFTR protein in the ER (lane 1). Lysates of thapsigargin-treated cells contained the ~170 kDa mature form of the ΔF508CFTR protein, indicating that the protein had been released from the ER and allowed to proceed along the biosynthetic pathway through the Golgi complex (lane 2).

Experiment 8. Thapsigargin Treatment can Induce Reversal of a Phenotypic Defect in CF Mice.

Materials and Methods. CF mice, which were the kind gift of Mitch Drumm, have had the ΔF508 mutation introduced into their endogenous copies of the CFTR gene by homologous recombination and are homozygous for the ΔF508 mutation. Construction of these mice is described in Zeiher, G. B., et al., A mouse model for the delta F508 allele of cystic fibrosis. *J. Clin. Invest.* 96: 2051-2064, 1995, and additional studies of these mice are described in Steagall W K and Drumm M L, Stimulation of cystic fibrosis transmembrane conductance regulator-dependent short-circuit currents across Delta F508 murine intestines. *Gastroenterology*, 116 (6):1379-88, 1999.

Nasal potential difference was measured essentially as described in Grubb, B. R., Vick, R. N., and Boucher, R. C., Hyperabsorption of $Na^+$ and raised $Ca^{2+}$-mediated $Cl^-$ secretion in nasal epithelia of CF mice, *Am. J. Physiol.*, 266: C1478-1483, 1994 and Ramjeesingh, M., et al., Assessment of the efficacy of in vivo CFTR protein replacement therapy in CF mice, *Hum Gene Ther.*, 9(4):521-8, 1998.

CF mutant and wild type mice were maintained under standard conditions except that Colyte was substituted for drinking water. Substitution of drinking water with Colyte (an electrolyte solution containing 6% polyethylene glycol) has been shown to allow certain CF mutant mice to consume mouse food, which assists in prolonging their life span and has certain advantages over a liquid diet (Grubb, B. R., *Am. A Physiol.* 268: G505-G513, 199S.)

Wild type and CF mice were exposed to a humidified atmosphere (produced as described in Example 4) containing 1 µM thapsigargin for 3 hours/day for 7-14 days. For histologic examination of lung tissue, wild type animals exposed to this treatment for 21 days revealed no gross pathologic changes (FIG. 8). The night before the NPD procedure was performed, mice were taken off Colyte and given water or alimentum (liquid formula). Wet food was also withheld. These steps were taken to decrease the risk of dehydration and/or intestinal obstruction that occur with sedation and dehydration.

The NPD protocol was performed as follows:

A 10 ml syringe was filled with each test solution, making sure that there were no bubbles in the microperfusion pump system. The 4 solutions used were: i) control—Ringers, ii) Ringers with amiloride $10^{-5}$ M, iii) Ringers with 0 mM chloride and amiloride $10^{-5}$ M, iv) Ringers with 0 mM chloride, amiloride $10^{-5}$ M, and isoproterenol $10^{-5}$ M. The electrodes were then attached to a voltmeter. One electrode was used as a subcutaneous reference electrode (27 gauge butterfly needle placed either in the belly or the tail) and the other was included in the system leading to the nose. Before attaching the electrodes to the system, agar bridges were placed in control Ringer solution, and the electrodes were zeroed. The syringe pump was set to recognize 10 ml syringes, and the flow rate was set to 0.15 mls/hr.

Mice were anaesthetized with Ketamine 100 mg/kg (range 75-100 mg/kg) and Xilazine 10 mg/kg (range 5-10 mg/kg) (ketamine and xilazine were either prediluted with saline and then mixed in a 1 ml syringe or were mixed in a microfuge tube with micropipetters and then diluted with saline). A total volume of 0.5 mls was used for intraperitoneal injection into the right side of the lower abdomen. If second dosages of anaesthesia were needed intraperitoneal injection of 50 mg/kg ketamine and 5 mg/kg xilazine (0.5 ml total volume) was performed.

A heat pad was warmed in a microwave oven for 1 min and then for a further 30 secs to achieve an appropriate temperature for maintaining mice during the NPD procedure. Each mouse was placed on a heat pad and PE10 tubing inserted into the nose. The end of the tubing was previously pulled to a very small diameter under the microscope to minimize trauma to mouse nasal mucosa. Saline eye drops were applied intermittently to decrease risk of corneal abrasions during the procedure.

After obtaining a stable baseline reading, infusion of Ringers solution was begun, and recording was initiated. After 5 mins of stable reading, the solution was changed successively to: (i) Ringer solution containing amiloride $10^{-5}$ M; (ii) Ringer solution containing 0 mM chloride and $10^{-5}$ M amiloride; (iii) Ringer solution containing 0 mM chloride, $10^{-5}$ M amiloride, and $10^{-5}$ M isoproterenol. NPD was recorded for each solution for 5 minutes of stable values. Following the procedure 1 cc of warm saline was injected IP to aid with rehydration. After recovery mice were maintained on a liquid diet overnight.

Each data point in FIG. 7 represents an average of results obtained using groups of 4-6 animals. Error bars represent standard error. Statistical analysis was performed using Jandel's Sigmastat and Excel.

Results. In human CF patients, both upper and lower airways exhibit reduced or absent cAMP-mediated $Cl^-$ secretion and hyperabsorption of $Na^+$. It is believed that the hyperabsorption of $Na^+$ and osmotically linked water absorption contribute substantially to the thick, viscous, mucus that characterizes the disease. In humans with CF, measurement of the electrical potential across the nasal mucosa in vivo has been used to demonstrate hyperabsorption of $Na^+$ across the airway epithelium (Knowles, M., Gatzy, J., and Boucher, J., "Increased bioelectric potential difference across respiratory epithelia in cystic fibrosis", *N. Engl. J. Med.* 305: 1489-1495, 1981). The same technique has been applied to the mouse. CF patients and various CF mouse models in which the murine CFTR gene has been mutated, deleted, or replaced by a mutant CFTR gene containing a mutation corresponding to a CF-causing mutation in humans (referred to herein as CF mice) exhibit a raised (i.e., more negative) baseline transnasal potential difference (NPD) as compared to that in normal subjects (Grubb, B. R., et al., Inefficient gene transfer by adenovirus vector to cystic fibrosis airway epithelia of mice and humans, *Nature*, 371: 802-806, 1994; Grubb, B. R., Vick, R. N., and Boucher, R. C., *Am. J. Physiol.*, 266: C1478-1483, 1994; reviewed in Grubb, B. and Boucher, R. C., Pathophysiology of gene-targeted mouse models for cystic fibrosis, *Physiological Reviews*, 79 (Suppl 1), 1999). Furthermore, various CF mice display a significantly greater decrease in NPD in response to amiloride, a drug that blocks electrogenic $Na^+$ absorption, than do control mice. In normal mice and humans perfusion of the nasal mucosa with a solution containing a low $Cl^-$ concentration leads to a hyperpolarization of the NPD. In contrast, in CF individuals either no change or a slight depolarization of the basal PD is observed under such conditions. Thus the alterations in NPD that characterize CF mice appear to accurately reflect those seen in human CF subjects. These results suggest that treatments tending to restore the behavior of the NPD in CF mice towards that observed in normal mice will have similar effects in human CF patients and are likely to be effective treatments for CF.

To determine the effect of thapsigargin treatment in vivo, we measured nasal potential difference (NPD) in thapsigargin treated or untreated wild type and genotypically CF mice. The transnasal potential difference (NPD) reports the electrical potential difference across the nasal epithelial cells, and thus permits the assessment of these cells' capacity to participate in absorption and secretion of $Na^+$ and $Cl^-$.

As can be seen in FIG. 7, treated (open squares) and untreated (filled squares) wild type animals manifest a small lumen negative transepithelial potential that is further reduced by the addition of the sodium channel blocker amiloride. Replacement of the fluid in the lumen with a solution containing 0 mM $Cl^-$ results in increases in the magnitude of the lumen negative potential. This effect is further enhanced through the addition of isoproterenol, which stimulates CFTR by raising intracellular cAP levels.

These results are consistent with the interpretation that, in normal mice (and humans), the nasal epithelium carries out electrogenic $Na^+$ absorption, mediated by an amiloride-sensitive Nat channel. The presence of the CFTR chloride channel on the apical surfaces of these cells allows $Cl^-$ to follow $Na^+$ and thus reduces the magnitude of the transepithelial potential. In the presence of amiloride and in the absence of lumenal $Cl^-$ CFTR permits net $Cl^-$ secretion, which is further stimulated by activation of CFTR through isoproterenol treatment. Mice homozygous for a CF-causing mutation (open circles) exhibit a markedly increased amiloride-sensitive lumen negative potential, consistent with the absence of a conductive pathway for $Cl^-$. Similarly, removal of lumen $Cl^-$ and isoproterenol treatment do not enhance net $Cl^-$ secretion in CF mice. In thapsigargin-treated CF mice (filled circles), the NPD is markedly reduced relative to that in untreated CF mice ($p<0.05$), approximating that seen in wild type mice. Normal levels of net $Cl^-$ secretion are detected in CF mice that have been treated with thapsigargin when lumen $Cl^-$ is removed in the presence of amiloride and isoproterenol, whereas untreated CF mice exhibit a markedly reduced (i.e., less negative) NPD ($p<0.05$).

All of the animals tolerated thapsigargin treatment without exhibiting any obvious morbidity. FIG. 8 shows the histologic appearance of lung tissue from control mice and mice treated with thapsigargin for 21 days. Panel A shows sections of lung tissue from untreated mice, and Panels B and C show lung tissue sections from thapsigargin-treated mice, Alveolar and bronchiolar architecture was normal in all sections examined. Moderate accumulation of peribronchiolar lymphocytes was detected in sections from one of the treated mice (C), whereas the density of peribronchiolar lymphocytes in the other treated mice was within normal limits (compare A and B) The scale bar in panel C=280 μm.

These results demonstrate that thapsigargin treatment can be clinically tolerated in doses sufficient to induce a significant reversal of a phenotypic defect in CF mice.

Experiment 9. Immuno Fluorescence Analysis of ΔF508 CFTR in Cells Treated with Curcumin.

Materials and Methods. Delta F508-expressing CHO cells (Pind S. Riordan J R. Williams D B. *Journal of Biological Chemistry*, 269(17):12784-8, 1994) were grown to confluence on glass coverslips and exposed to media containing curcumin (50 microM) for 90 min, followed by a 90 min incubation in the absence of the drug. Immunofluorescence labeling was performed using a monoclonal antibody directed against the CFTR C-terminus (MAB25031, R&D Systems). Images were acquired on a Zeiss LSM 410 laser scanning confocal microscope. Contrast and brightness settings were chosen so that all pixel values were within the linear range. Images are the product of 8-fold line averaging.

Figure 9A:
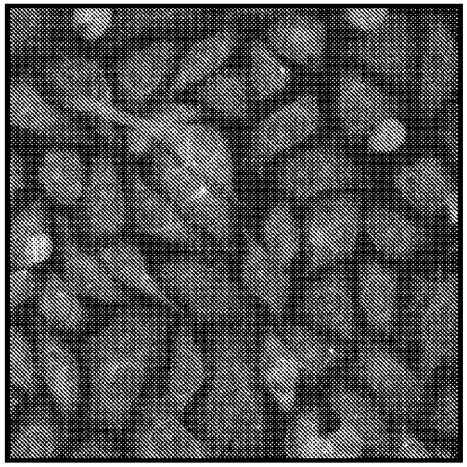
Figure 9B:
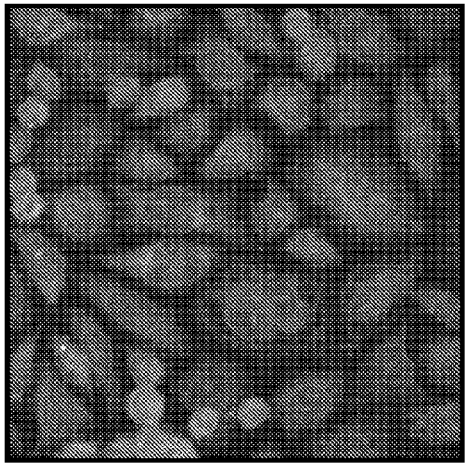
Figure 9C:
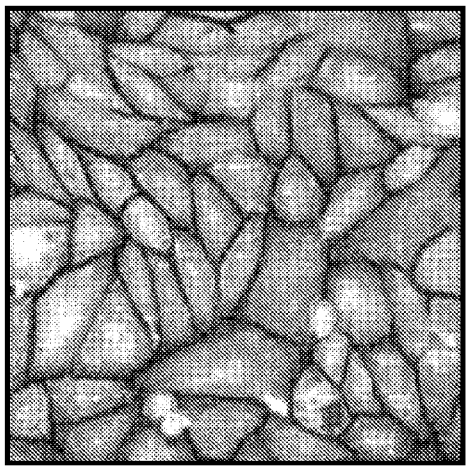
Figure 9D:
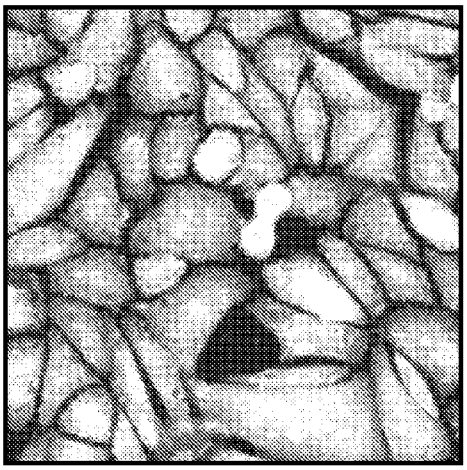

Results. To determine whether the effects of curcumin on Delta F508 CFTR function are associated with alterations in the subcellular distribution of the Delta F508 protein, immunofluorescent localization of the CFTR protein was performed in treated and untreated CHO cells that express Delta F508 CFTR by transfection. In untreated cells, CFTR staining was detectable in a diffuse cytoplasmic pattern surrounding the nucleus (FIGS. 9A and 9B). This pattern is consistent with the localization of the Delta F508-CFTR protein to the ER in the untreated cells. In treated cells, bright labeling of the cell surface was detected in all of the cells (FIGS. 9C and 9D). Images in FIG. 9 are en face views. Treated and untreated cells were imaged at the same contrast and brightness and settings. Thus the differences in brightness between panels depicting untreated cells (A, B) and treated cells (C, D) is likely to reflect the accumulation of more CFTR protein in the treated cells. The misfolded protein trapped in the ER has a very short half life and is rapidly degraded. The cohort of protein that gets to the cell surface appears to have a longer half-life. Consequently, the treated cells possess more CFTR protein, as well as having it localized at the cell surface. No staining was seen in samples exposed only to the secondary antibodies (not shown).

Experiment 10. Curcumin Treatment can Induce Reversal of a Phenotypic Defect in CF Mice.

Materials and Methods. CF mice were as described in Experiment 8. CF mutant and wild type mice were maintained as described in Experiment 8. Treatment with curcumin, thapsigargin, DBHQ, or control (saline) and determination of the nasal potential difference (NPD) were performed essentially as described in Experiment 8 except that the nebulization device was filled with 5 ml of 1 microM thapsigargin dissolved in physiologic saline solution or 50 microM curcumin dissolved in normal saline. Each data point in FIG. 10 represents an average of results obtained using groups of animals. N=7 for the wild type treated and untreated groups. N=10 for the ΔF508 CFTR untreated and thapsigargin treated groups N=6 for the ΔF508 CFTR curcumin treated group. Error bars represent standard error. Statistical analysis was performed using Jandel's Sigmastat and Excel. Thapsigargin and curcumin were obtained from Sigma.

Results: Gene targeted mice homozygous for the ΔF508 mutation were exposed to a humidified atmosphere containing 1 microM aerosolized thapsigargin, 12 microM aerosolized DBHQ or 50 microM aerosolized curcumin for 3 hours/day for 7-14 days. At the end of this treatment period, the membrane potential difference across their nasal epithelia (NPD) was measured. FIG. 10 shows plots of nasal potential difference (NPD) measurements in treated and untreated wild-type and ΔF508 CFTR mice. The tracing represents the time course of NPD measurement. The response of NPD readings when perfusion in control Ringer's solution was switched to perfusion with Ringer's solution containing amiloride, low chloride with amiloride, and isoproterenol in low chloride with amiloride is indicated by the arrows. Circles represent ΔF508 CFTR mice, squares represent wild-type mice. Open circles and squares correspond to untreated animals. Closed circles and squares correspond to thapsigargin-treated animals. Closed diamonds represent ΔF508 mice that have been treated with nebulized curcumin. Curcumin and thapsigargin treatments dramatically reduce the basal NPD in ΔF508 CFTR mice and result in responses to 0 Cl− and isoproterenol that are nearly indistinguishable from those of wild-type mice. CF and wild-type mice exposed to nebulized normal saline as a control exhibit no changes in NPD (data not shown).

In untreated CF-affected animals the nasal epithelium exhibited a large, lumen-negative potential that was sensitive to amiloride, reflecting electrogenic Na+ absorption (see FIG. 10). Removal of luminal Cl− and exposure to isoproterenol did not substantially alter the potential in untreated ΔF508 animals. In marked contrast, curcumin and thapsigargin-treated ΔF508 animals manifested a significantly smaller baseline NPD, approaching the small lumen-negative potentials seen at rest in wild-type animals. Removal of luminal Cl− increased the magnitude of this potential in both treated and wild-type animals. This effect was further enhanced by isoproterenol, presumably as a result of the cAMP-mediated activation of apical Cl− secretion through functional CFTR channels.

All of the animals tolerated curcumin treatment without exhibiting any obvious morbidity. These results demonstrate that curcumin treatment can be clinically tolerated in doses sufficient to induce a significant reversal of a phenotypic defect in CF mice.

The foregoing detailed description has been given for clearness of understanding only and no unnecessary limitations should be understood therefrom as modifications will be obvious to those skilled in the art.

While the invention has been described in connection with specific embodiments thereof it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method of reducing the basal nasal potential difference (NPD) in an individual suffering from or at risk of cystic fibrosis (CF), the method comprising the step of:
   administering to an individual who carries a genetic mutation that generates an active but misfolded or misassembled cystic fibrosis transmembrane conductance regulator (CFTR) protein, which active but misfolded or misassembled CFTR protein is retained in the endoplasmic reticulum (ER) to a greater degree than is correctly folded and assembled CFTR protein such that the individual suffers from or is susceptible to CF a composition comprising a compound selected from the group consisting of curcumin I, curcumin II, curcumin III, or a combination of the foregoing, to the individual to achieve a statistically significant reduction in basal NPD; and
   detecting the statistically significant reduction in basal NPD.

2. The method of claim 1, wherein the compound is curcumin I.

3. The method of claim 2, wherein the composition is administered as an aerosol.

4. The method of claim 2, wherein the composition is administered intranasally.

5. The method of claim 2, wherein the composition is administered orally.

6. The method of claim 2, wherein the mutation is a deletion of the phenylalanine at amino acid position 508 of CFTR.

7. The method of claim 1, wherein the step of detecting comprises determining that one or more symptoms of the cystic fibrosis has been alleviated.

8. The method of claim 7, wherein the one or more symptoms include sweat chloride levels.

9. The method of claim 7, wherein the one or more symptoms include chronic respiratory infections.

10. The method of claim 7, wherein the one or more symptoms include impaired pancreatic and digestive function.

* * * * *